US010556844B2

(12) United States Patent
Nave et al.

(10) Patent No.: US 10,556,844 B2
(45) Date of Patent: Feb. 11, 2020

(54) PYRAZOLE COMPOUNDS AS NITRIFICATION INHIBITORS

(71) Applicant: BASF SE, Ludwigshafen (DE)

(72) Inventors: Barbara Nave, Ruppertsberg (DE); Joachim Dickhaut, Heidelberg (DE); Peter Nesvadba, Marly (CH); Mihiret Tekeste Sisay, Mannheim (DE); Alexander Wissemeier, Speyer (DE); Wolfram Zerulla, St Martin (DE); Gregor Pasda, Neustadt (DE); Olof Wallquist, Basel (CH); Allan F Cunningham, Magden (CH)

(73) Assignee: BASF SE, Ludwigshafen am Rhein (DE)

(*) Notice: Subject to any disclaimer, the term of this patent is extended or adjusted under 35 U.S.C. 154(b) by 150 days.

(21) Appl. No.: 15/548,561

(22) PCT Filed: Feb. 5, 2016

(86) PCT No.: PCT/EP2016/052557
§ 371 (c)(1),
(2) Date: Aug. 3, 2017

(87) PCT Pub. No.: WO2016/124769
PCT Pub. Date: Aug. 11, 2016

(65) Prior Publication Data
US 2018/0016199 A1 Jan. 18, 2018

(30) Foreign Application Priority Data

Feb. 6, 2015 (EP) .................................... 15154162

(51) Int. Cl.
| C05G 3/08 | (2006.01) |
| C07D 231/12 | (2006.01) |
| C07D 231/54 | (2006.01) |
| C05C 3/00 | (2006.01) |
| C07D 401/04 | (2006.01) |
| C07D 403/04 | (2006.01) |
| C07D 403/12 | (2006.01) |
| C07D 471/04 | (2006.01) |

(52) U.S. Cl.
CPC .................. *C05G 3/08* (2013.01); *C05C 3/00* (2013.01); *C07D 231/12* (2013.01); *C07D 231/54* (2013.01); *C07D 401/04* (2013.01); *C07D 403/04* (2013.01); *C07D 403/12* (2013.01); *C07D 471/04* (2013.01)

(58) Field of Classification Search
CPC ...... C05G 3/08; C07D 401/04; C07D 403/12; C07D 403/04; C07D 471/04; C07D 231/56; C07D 231/18; C07D 231/54; C07D 231/12; C07D 231/20; C07D 231/14; C05C 3/00; A01N 43/56; A01N 43/58; Y02P 60/218
See application file for complete search history.

(56) References Cited

U.S. PATENT DOCUMENTS

| 3,060,084 A | 6/1961 | Littler et al. |
| 3,296,272 A | 1/1967 | Johnston et al. |
| 3,299,566 A | 1/1967 | Macmullen et al. |
| 3,325,503 A | 6/1967 | Bimber et al. |
| 3,635,690 A | 1/1972 | Griffith |
| 3,920,442 A | 11/1975 | Albert et al. |
| 4,144,050 A | 3/1979 | Frensch et al. |
| 4,172,714 A | 10/1979 | Albert et al. |
| 4,552,581 A | 11/1985 | Bremner et al. |
| 5,074,904 A | 12/1991 | Ditrich et al. |
| 5,180,587 A | 1/1993 | Moore et al. |
| 5,208,030 A | 5/1993 | Hoy et al. |
| 5,232,701 A | 8/1993 | Ogawa et al. |
| 6,124,117 A | 9/2000 | Kilburn et al. |
| 6,180,141 B1 | 1/2001 | Lemercier et al. |
| 6,489,438 B1 | 12/2002 | Erhardt et al. |
| 8,075,659 B2 | 12/2011 | Wissemeier et al. |
| 2007/0280981 A1 | 12/2007 | Birthisel et al. |
| 2010/0137582 A1 | 6/2010 | Endo et al. |
| 2011/0046186 A1 | 2/2011 | Li et al. |
| 2011/0237588 A1 | 9/2011 | Es-Sayed et al. |
| 2013/0316904 A1 | 11/2013 | Dietrich et al. |
| 2017/0036969 A1 | 2/2017 | Nave et al. |
| 2017/0181435 A1 | 6/2017 | Nave et al. |
| 2017/0223964 A1 | 8/2017 | Nave et al. |

FOREIGN PATENT DOCUMENTS

| CN | 101715777 A | 6/2010 |
| CN | 102126994 A | 7/2011 |
| CN | 102613183 A | 8/2012 |
| DE | 19650197 A1 | 6/1988 |
| DE | 10021412 A1 | 6/2001 |
| DE | 102005009458 A1 | 9/2006 |

(Continued)

OTHER PUBLICATIONS

Adamo et al. "Practical routes to diacetylenic ketones and their application for the preparation of alkynyl substituted pyridines, pyrimidines and pyrazoles", Tetrahedron 59 (2003) 2197-2205 (Year: 2003).*
Extended European Search Report for EP Patent Application No. 15154162.0, dated May 22, 2015, 10 pages.
International Search Report and Written Opinion for International Application No. PCT/EP2016/052557, dated Mar. 14, 2016, 11 pages.
Subbarao et al., 2012, Advances in Agronomy, 114, 249-302.
Nelson and Huber; Nitrification inhibitors for corn production (2001), National Corn Handbook, Iowa State University.

(Continued)

Primary Examiner — Amber R Orlando
Assistant Examiner — Syed T Iqbal
(74) Attorney, Agent, or Firm — Armstrong Teasdale LLP

(57) ABSTRACT

Pyrazole derivatives as nitrification inhibitors are described herein.

30 Claims, No Drawings

(56) References Cited

FOREIGN PATENT DOCUMENTS

| | | |
|---|---|---|
| DE | 102011120098 A1 | 6/2013 |
| DE | 102013022031 B3 | 9/2014 |
| EP | 141317 A2 | 5/1985 |
| EP | 152031 A2 | 8/1985 |
| EP | 226917 A1 | 7/1987 |
| EP | 243970 A1 | 11/1987 |
| EP | 256503 A2 | 2/1988 |
| EP | 374753 A2 | 6/1990 |
| EP | 392225 A2 | 10/1990 |
| EP | 427529 A1 | 5/1991 |
| EP | 428941 A1 | 5/1991 |
| EP | 451878 A | 10/1991 |
| EP | 532022 A1 | 3/1993 |
| EP | 707445 A1 | 4/1996 |
| EP | 1028125 A1 | 8/2000 |
| EP | 1035122 A1 | 9/2000 |
| EP | 1122244 A1 | 8/2001 |
| EP | 1124414 A1 | 8/2001 |
| EP | 1201648 A1 | 5/2002 |
| EP | 954213 B1 | 5/2003 |
| EP | 1700634 A1 | 9/2006 |
| EP | 2700634 A1 | 2/2014 |
| GB | 2095558 A | 10/1982 |
| JP | 2001-039954 A | 2/2001 |
| JP | 2002316902 A | 10/2002 |
| JP | 2007039954 A | 2/2007 |
| WO | 9113546 A1 | 9/1991 |
| WO | 93007278 A1 | 4/1993 |
| WO | 9534656 A1 | 12/1995 |
| WO | 9846608 A1 | 10/1998 |
| WO | 9914187 A1 | 3/1999 |
| WO | 9924413 A2 | 5/1999 |
| WO | 9927783 A1 | 6/1999 |
| WO | 0029404 A1 | 5/2000 |
| WO | 0046148 A1 | 8/2000 |
| WO | 0065913 A1 | 11/2000 |
| WO | 0154501 A2 | 8/2001 |
| WO | 0156358 A2 | 8/2001 |
| WO | 02015701 A2 | 2/2002 |
| WO | 0222583 A2 | 3/2002 |
| WO | 0240431 A2 | 5/2002 |
| WO | 0314103 A1 | 2/2003 |
| WO | 0316286 A1 | 2/2003 |
| WO | 0316303 A1 | 2/2003 |
| WO | 0318810 A2 | 3/2003 |
| WO | 03031477 A1 | 4/2003 |
| WO | 0310149 A1 | 6/2003 |
| WO | 0352073 A2 | 6/2003 |
| WO | 0353145 A1 | 7/2003 |
| WO | 0361388 A1 | 7/2003 |
| WO | 0366609 A1 | 8/2003 |
| WO | 0374491 A1 | 9/2003 |
| WO | 0449804 A2 | 6/2004 |
| WO | 0483193 A1 | 9/2004 |
| WO | 2005102045 A1 | 3/2005 |
| WO | 0563721 A1 | 7/2005 |
| WO | 2005077934 A1 | 8/2005 |
| WO | 0587772 A2 | 9/2005 |
| WO | 0587773 A1 | 9/2005 |
| WO | 05120234 A2 | 12/2005 |
| WO | 05123689 A1 | 12/2005 |
| WO | 05123690 A1 | 12/2005 |
| WO | 2005120226 A1 | 12/2005 |
| WO | 0615866 A1 | 2/2006 |
| WO | 0687325 A1 | 8/2006 |
| WO | 0687343 A1 | 8/2006 |
| WO | 2006089633 A2 | 8/2006 |
| WO | 06112700 A1 | 10/2006 |
| WO | 2007006670 A1 | 1/2007 |
| WO | 2007043677 A1 | 4/2007 |
| WO | 0767042 A1 | 6/2007 |
| WO | 0767044 A2 | 6/2007 |
| WO | 0782098 A2 | 7/2007 |
| WO | 0790624 A2 | 8/2007 |
| WO | 2007101369 A1 | 9/2007 |
| WO | 2007101540 A1 | 9/2007 |
| WO | 2006043635 A1 | 4/2008 |
| WO | 2008067911 A1 | 6/2008 |
| WO | 2008134969 A1 | 11/2008 |
| WO | 0990181 A2 | 7/2009 |
| WO | 2009124707 A2 | 10/2009 |
| WO | 2010006713 A2 | 1/2010 |
| WO | 2010018714 A1 | 2/2010 |
| WO | 2010034737 A1 | 4/2010 |
| WO | 10069882 A1 | 6/2010 |
| WO | 2010060379 A1 | 6/2010 |
| WO | 2010069266 A1 | 6/2010 |
| WO | 2010127926 A1 | 11/2010 |
| WO | 2010129497 A1 | 11/2010 |
| WO | 2011009572 A1 | 1/2011 |
| WO | 2011015305 A2 | 2/2011 |
| WO | 11028657 A1 | 3/2011 |
| WO | 201177514 A1 | 6/2011 |
| WO | 2011069456 A1 | 6/2011 |
| WO | 2011085575 A1 | 7/2011 |
| WO | 11135833 A1 | 11/2011 |
| WO | 2012000896 A2 | 1/2012 |
| WO | 2012034403 A1 | 3/2012 |
| WO | 2012084670 A1 | 6/2012 |
| WO | 2012029672 A1 | 8/2012 |
| WO | 2012143317 A1 | 10/2012 |
| WO | 2012168188 A1 | 12/2012 |
| WO | 13007767 A1 | 1/2013 |
| WO | 13010862 A1 | 1/2013 |
| WO | 2013003977 A1 | 1/2013 |
| WO | 2013050317 A1 | 1/2013 |
| WO | 0311853 A1 | 2/2013 |
| WO | 13024009 A1 | 2/2013 |
| WO | 13024010 A1 | 2/2013 |
| WO | 2013024009 A1 | 2/2013 |
| WO | 2013024010 A1 | 2/2013 |
| WO | 13047441 A1 | 4/2013 |
| WO | 13047749 A1 | 4/2013 |
| WO | 2013055584 A1 | 4/2013 |
| WO | 13092224 A1 | 6/2013 |
| WO | 13127704 A1 | 9/2013 |
| WO | 2013129688 A1 | 9/2013 |
| WO | 13162072 A1 | 10/2013 |
| WO | 2014051165 A1 | 4/2014 |
| WO | 2014126208 A1 | 8/2014 |
| WO | 13047441 A1 | 4/2015 |
| WO | 2015104699 A2 | 7/2015 |
| WO | 2015104700 A2 | 7/2015 |
| WO | 2016075289 A1 | 5/2016 |
| WO | 2016097318 A1 | 6/2016 |
| WO | 2016103168 A1 | 6/2016 |

OTHER PUBLICATIONS

Baikalova, et al., "Reactions of 1-Allenylpyrazole and 1-Allenyl-1,2,4-triazole with Hydrogen Chloride and Metal Chlorides", Russian Journal of General Chemistry, vol. 73, Issue 10, Oct. 2003, pp. 1634-1640.

Rodriguez-Franco, et al., "Synthesis of new 1-(but-2-ynyl)pyrazoles: containing a pyrrolidine or diethylamine moiety and their muscarinic properties", Arch Pharm chemistry in Life Sciences, vol. 335, Issue 7, 2002, pp. 339-346.

\* cited by examiner

PYRAZOLE COMPOUNDS AS NITRIFICATION INHIBITORS

CROSS-REFERENCE TO RELATED APPLICATIONS

This application is a U.S. National Phase Application of PCT/EP2016/052557, filed Feb. 5, 2016, which claims the benefit of priority to EP Patent Application No. 15154162.0, filed Feb. 6, 2015, the entire contents of which are hereby incorporated by reference herein.

BACKGROUND

The present invention relates to novel nitrification inhibitors of formula I. Moreover, the invention relates to the use of compounds of formula I as nitrification inhibitors, i.e. for reducing nitrification, as well as agrochemical mixtures and compositions comprising the nitrification inhibitors. Further encompassed by the present invention are methods for reducing nitrification, said methods comprising the treatment of plants, soil and/or loci where the plant is growing or is intended to grow with said nitrification inhibitors and methods for treating a fertilizer or a composition by applying said nitrification inhibitor.

Nitrogen is an essential element for plant growth and reproduction. About 25% of the plant available nitrogen in soils (ammonium and nitrate) originates from decomposition processes (mineralization) of organic nitrogen compounds such as humus, plant and animal residues and organic fertilizers. Approximately 5% derive from rainfall. On a global basis, the biggest part (70%), however, is supplied to the plant by inorganic nitrogen fertilizers. The mainly used nitrogen fertilizers comprise ammonium compounds or derivatives thereof, i.e. nearly 90% of the nitrogen fertilizers applied worldwide is in the $NH_4^+$ form (Subbarao et al., 2012, Advances in Agronomy, 114, 249-302). This is, inter alia, due to the fact that $NH_4^+$ assimilation is energetically more efficient than assimilation of other nitrogen sources such as $NO_3^-$.

Moreover, being a cation, $NH_4^+$ is held electrostatically by the negatively charged clay surfaces and functional groups of soil organic matter. This binding is strong enough to limit $NH_4^+$-loss by leaching to groundwater. By contrast, $NO_3^-$, being negatively charged, does not bind to the soil and is liable to be leached out of the plants' root zone. In addition, nitrate may be lost by denitrification which is the microbiological conversion of nitrate and nitrite ($NO_2^-$) to gaseous forms of nitrogen such as nitrous oxide ($N_2O$) and molecular nitrogen ($N_2$).

However, ammonium ($NH_4^+$) compounds are converted by soil microorganisms to nitrates ($NO_3^-$) in a relatively short time in a process known as nitrification. The nitrification is carried out primarily by two groups of chemolithotrophic bacteria, ammonia-oxidizing bacteria (AOB) of the genus *Nitrosomonas* and *Nitrobacter*, which are ubiquitous component of soil bacteria populations. The enzyme, which is essentially responsible for nitrification is ammonia monooxygenase (AMO), which was also found in ammonia-oxidizing archaea (Subbarao et al., 2012, Advances in Agronomy, 114, 249-302).

The nitrification process typically leads to nitrogen leakage and environmental pollution. As a result of the various losses, approximately 50% of the applied nitrogen fertilizers are lost during the year following fertilizer addition (see Nelson and Huber; Nitrification inhibitors for corn production (2001), National Corn Handbook, Iowa State University).

As countermeasures the use of nitrification inhibitors, mostly together with fertilizers, was suggested. Suitable nitrification inhibitors include biological nitrification inhibitors (BNIs) such as linoleic acid, alpha-linolenic acid, methyl p-coumarate, methyl ferulate, MHPP, Karanjin, brachialacton or the p-benzoquinone sorgoleone (Subbarao et al., 2012, Advances in Agronomy, 114, 249-302). Further suitable nitrification inhibitors are synthetic chemical inhibitors such as Nitrapyrin, dicyandiamide (DCD), 3,4-dimethyl pyrazole phosphate (DMPP), 4-amino-1,2,4-triazole hydrochloride (ATC), 1-amido-2-thiourea (ASU), 2-amino-4-chloro-6-methylpyrimidine (AM), 5-ethoxy-3-trichloromethyl-1,2,4-thiodiazole (terrazole), or 2-sulfanilamidothiazole (ST) (Slangen and Kerkhoff, 1984, Fertilizer research, 5(1), 1-76).

Furthermore, pyrazole-based nitrification inhibitors have been described, e.g., in U.S. Pat. No. 3,635,690, WO 2011/009572, WO 2011/015305, DE 10 2011 120 098, and DE 10 2013 022 031 B3. U.S. Pat. No. 3,635,690 describes 1-propynyl pyrazole, i.e. 1-prop-1-ynyl pyrazole with an internal triple bond, as nitrification inhibitor. Phenylacetylene, wherein the triple bond is a terminal triple bond, is described as nitrification inhibitor in U.S. Pat. No. 4,552,581.

However, many of these inhibitors only work sub-optimal. In addition, the world population is expected to grow significantly in the next 20-30 years, and, therefore, food production in sufficient quantities and quality is necessary. In order to achieve this, the use of nitrogen fertilizers would have to double by 2050. For environmental reasons, this is not possible, since nitrate levels in drinking water, eutrophication of surface water and gas emissions into the air have already reached critical levels in many places, causing water contamination and air pollution. However, fertilizer efficiency increases significantly and less fertilizer may therefore be applied, if nitrification inhibitors are used. Therefore, there is a clear need for novel nitrification inhibitors, as well as for methods using them.

In particular, there is a need for nitrification inhibitors with a high activity.

Furthermore, there is a need for nitrification inhibitors which are effective at low amounts, as low application rates typically result in economical and environmental advantages.

It was therefore the object of the present invention to provide improved nitrification inhibitors in view of the prior art.

DETAILED DESCRIPTION

The present invention addresses this need and relates to a nitrification inhibitor of formula I

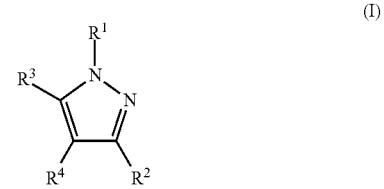

or a stereoisomer, salt, tautomer or N-oxide thereof, wherein

R$^1$ is C$_3$-C$_6$-alkynyl, with the proviso that if R$^1$ is C$_3$-alkynyl, it is propargyl, or C$_3$-C$_6$-allenyl, wherein the C-atoms of these groups may in each case be unsubstituted or may carry 1, 2, or 3 identical or different substituents selected from halogen, CN, OR$^a$, NO$_2$, NR$^c$R$^d$, NR$^b$(C=O)R$^a$, C(=O)R$^a$, C(=O)OR$^a$, C(=O)NR$^c$R$^d$, S(O)$_m$R$^a$, and S(O)$_m$NR$^c$R$^d$;

and wherein

R$^2$, R$^3$ and R$^4$ are independently of each other selected from
- H, halogen, CN, OR$^a$, NO$_2$, NR$^c$R$^d$, NR$^b$(C=O)R$^a$, C(=O)R$^a$, C(=O)OR$^a$, C(=O)NR$^c$R$^d$, S(O)$_m$R$^a$, S(O)$_m$NR$^c$R$^d$;
- C$_1$-C$_8$-alkyl, C$_3$-C$_8$-cycloalkyl, C$_2$-C$_8$-alkenyl, C$_2$-C$_8$-alkynyl, wherein the C-atoms of these groups may in each case be unsubstituted or may carry 1, 2, or 3 identical or different substituents selected from halogen, CN, OR$^a$, NO$_2$, NR$^c$R$^d$, NR$^b$(C=O)R$^a$, C(=O)R$^a$, C(=O)OR$^a$, C(=O)NR$^c$R$^d$, S(O)$_m$R$^a$, and S(O)$_m$NR$^c$R$^d$;
- C$_6$-C$_{10}$-aryl, and C$_5$-C$_{10}$-hetaryl, wherein the aromatic moieties may in each case be unsubstituted or may carry 1, 2, 3, 4, or 5 identical or different substituents selected from halogen, CN, OR$^a$, C$_1$-C$_4$-alkyl, C$_1$-C$_4$-haloalkyl, C$_2$-C$_4$-alkenyl, and C$_2$-C$_4$-alkynyl;

or R$^3$ and R$^4$ together form a bridge, which forms together with the atoms to which R$^3$ and R$^4$ are bonded an annulated partly or fully unsaturated, or aromatic 5 to 10-membered carbocyclic or heterocyclic ring, wherein the heterocyclic ring may carry 1, 2, or 3 heteroatoms being selected from O, S, and N, of which S and/or N may optionally be oxidized, and wherein the carbocyclic or heterocyclic ring may be unsubstituted or may carry 1, 2, 3, 4, or 5 identical or different substituents selected from =O, halogen, CN, OR$^a$, NO$_2$, NR$^c$R$^d$, NR$^b$(C=O)R$^a$, C(=O)R$^a$, C(=O)OR$^a$, C(=O)NR$^c$R$^d$, O(C=O)NR$^c$R$^d$, C$_1$-C$_4$-alkyl, C$_1$-C$_4$-haloalkyl, C$_6$-C$_{10}$-aryl, C$_5$-C$_{10}$-hetaryl, C$_5$-C$_{10}$-carbocyclyl, and C$_5$-C$_{10}$-heterocyclyl, wherein the C$_6$-C$_{10}$-aryl, C$_5$-C$_{10}$-hetaryl, C$_5$-C$_{10}$-carbocyclyl, and C$_5$-C$_{10}$-heterocyclyl moieties may be unsubstituted or may carry 1, 2, 3, 4, or 5 identical or different substituents selected from =O, halogen, CN, C$_1$-C$_4$-alkyl, and C$_1$-C$_4$-haloalkyl;

or R$^2$ and R$^4$ together form a bridge, which forms together with the atoms to which R$^2$ and R$^4$ are bonded an annulated partly or fully unsaturated, or aromatic 5 to 10-membered carbocyclic or heterocyclic ring, wherein the heterocyclic ring may carry 1, 2, or 3 heteroatoms being selected from O, S, and N, of which S and/or N may optionally be oxidized, and wherein the carbocyclic or heterocyclic ring may be unsubstituted or may carry 1, 2, 3, 4, or 5 identical or different substituents selected from =O, halogen, CN, OR$^a$, NO$_2$, NR$^c$R$^d$, NR$^b$(C=O)R$^a$, C(=O)R$^a$, C(=O)OR$^a$, C(=O)NR$^c$R$^d$, O(C=O)NR$^c$R$^d$, C$_1$-C$_4$-alkyl, C$_1$-C$_4$-haloalkyl, C$_6$-C$_{10}$-aryl, C$_5$-C$_{10}$-hetaryl, C$_5$-C$_{10}$-carbocyclyl, and C$_5$-C$_{10}$-heterocyclyl, wherein the C$_6$-C$_{10}$-aryl, C$_5$-C$_{10}$-hetaryl, C$_5$-C$_{10}$-carbocyclyl, and C$_5$-C$_{10}$-heterocyclyl moieties may be unsubstituted or may carry 1, 2, 3, 4, or 5 identical or different substituents selected from =O, halogen, CN, C$_1$-C$_4$-alkyl, and C$_1$-C$_4$-haloalkyl;

and wherein

R$^a$ is H, C$_1$-C$_8$-alkyl, C$_1$-C$_8$-haloalkyl, C$_2$-C$_8$-alkenyl, C$_2$-C$_8$-alkynyl;

C$_5$-C$_{10}$-hetaryl or C$_6$-C$_{10}$-aryl, wherein the C$_5$-C$_{10}$-hetaryl or C$_6$-C$_{10}$-aryl moieties may in each case be unsubstituted or may carry 1, 2, 3, 4, or 5 identical or different substituents selected from halogen, CN, OH, C$_1$-C$_4$-alkyl, C$_1$-C$_4$-alkoxy, C$_1$-C$_4$-haloalkyl, C$_2$-C$_4$-alkenyl, C$_2$-C$_4$-alkynyl, C$_5$-C$_6$-hetaryl and C$_6$-aryl, wherein said C$_5$-C$_6$-hetaryl and C$_6$-aryl moieties may be unsubstituted or may carry 1, 2, 3, 4, or 5 substituents selected from halogen, CN, OH, C$_1$-C$_4$-alkyl, C$_1$-C$_4$-alkoxy, C$_1$-C$_4$-haloalkyl, C$_2$-C$_4$-alkenyl, and C$_2$-C$_4$-alkynyl;

R$^b$ is H, C$_1$-C$_4$-alkyl, C$_3$-C$_8$-cycloalkyl, C$_2$-C$_4$-alkenyl, C$_2$-C$_8$-alkynyl, or C$_6$-C$_{10}$-aryl; and R$^c$ and R$^d$ are independently of each other selected from the group consisting of H, C$_1$-C$_4$-alkyl, C$_1$-C$_4$-haloalkyl, C$_3$-C$_8$-cycloalkyl, C$_6$-C$_{10}$-aryl, and C$_5$-C$_{10}$-hetaryl; or R$^c$ and R$^d$ together with the N-atom to which they are bonded form a 5- to 6-membered, saturated or unsaturated heterocycle, which may carry a further heteroatom being selected from O, S, and N as a ring member atom, of which S and/or N may optionally be oxidized, and wherein the heterocyclic ring may be unsubstituted or may carry 1, 2, 3, 4, or 5 substituents, which are independently selected from halogen, CN, OH, NO$_2$, C$_1$-C$_4$-alkyl, C$_1$-C$_4$-haloalkyl, C$_1$-C$_4$-alkoxy, and C$_1$-C$_4$-haloalkoxy;

and wherein m is 0, 1, or 2.

The inventors surprisingly found that by applying the compound of formula I as defined herein the nitrification of ammonium to nitrate can significantly be reduced.

Thus, in one aspect the present invention relates to the use of the compound of formula I as defined herein as a nitrification inhibitor.

In one preferred embodiment of said use, in said compound of formula I, R$^1$ is a terminal C$_3$-C$_4$-alkynyl group, preferably propargyl.

In another preferred embodiment of said use, in said compound of formula I, R$^1$ is a terminal C$_3$-C$_4$-allenyl group, preferably C$_3$-allenyl.

In a further preferred embodiment of said use, in said compound of formula I,

R$^2$, R$^3$ and R$^4$ are independently of each other selected from
- H, halogen, CN, OR$^a$, C(=O)R$^a$, C(=O)OR$^a$, C(=O)NR$^c$R$^d$;
- C$_1$-C$_8$-alkyl, wherein the C-atoms may be unsubstituted or may carry 1, 2, or 3 identical or different substituents selected from halogen, CN, and OR$^a$;
- C$_6$-C$_{10}$-aryl, and C$_5$-C$_{10}$-hetaryl, wherein the aromatic moieties may in each case be unsubstituted or may carry 1, 2, 3, 4, or 5 identical or different substituents selected from halogen, CN, OR$^a$, C$_1$-C$_4$-alkyl, C$_1$-C$_4$-haloalkyl, and C$_2$-C$_4$-alkynyl;

or R$^3$ and R$^4$ together form a bridge, which forms together with the atoms to which R$^3$ and R$^4$ are bonded an annulated partly or fully unsaturated, or aromatic 5 to 10-membered carbocyclic ring, wherein the carbocyclic ring may be unsubstituted or may carry 1, 2, 3, 4, or 5 identical or different substituents selected from =O, halogen, CN, OR$^a$, O(C=O)NR$^c$R$^d$, C$_5$-C$_{10}$-hetaryl, and C$_5$-C$_{10}$-heterocyclyl, wherein the C$_5$-C$_{10}$-hetaryl, and C$_5$-C$_{10}$-heterocyclyl moieties may be unsubstituted or may carry 1, 2, 3, 4, or 5 identical or different substituents selected from =O, halogen, CN, and C$_1$-C$_4$-haloalkyl;

or R$^2$ and R$^4$ together form a bridge, which forms together with the atoms to which R$^2$ and R$^4$ are bonded an annulated partly or fully unsaturated, or aromatic 5 to 10-membered carbocyclic ring, wherein the carbocyclic ring may be unsubstituted or may carry 1, 2, 3, 4, or 5 identical or different substituents selected from =O, halogen, CN, OR$^a$, O(C=O)NR$^c$R$^d$, C$_5$-C$_{10}$-hetaryl, and C$_5$-C$_{10}$-heterocyclyl, wherein the C$_5$-C$_{10}$-hetaryl, and C$_5$-C$_{10}$-heterocyclyl moieties may be unsubstituted or may carry 1, 2, 3, 4, or 5 identical or different substituents selected from =O, halogen, CN, and C$_1$-C$_4$-haloalkyl;

wherein

R$^a$ is H, C$_1$-C$_8$-alkyl, C$_1$-C$_8$-haloalkyl, C$_2$-C$_8$-alkynyl;

C$_5$-C$_{10}$-hetaryl or C$_6$-C$_{10}$-aryl, wherein the C$_5$-C$_{10}$-hetaryl or C$_6$-C$_{10}$-aryl moieties may in each case be unsubstituted or may carry 1, 2, 3, 4, or 5 identical or different substituents selected from halogen, CN, C$_1$-C$_4$-alkyl, C$_1$-C$_4$-haloalkyl, C$_2$-C$_4$-alkynyl, C$_5$-C$_6$-hetaryl and C$_6$-aryl, wherein said C$_5$-C$_6$-hetaryl and C$_6$-aryl moieties may be unsubstituted or may carry 1, 2, 3, 4, or 5 substituents selected from halogen, CN, C$_1$-C$_4$-alkyl, C$_1$-C$_4$-haloalkyl, and C$_2$-C$_4$-alkynyl; and R$^c$ and R$^d$ are independently of each other selected from the group consisting of H, C$_1$-C$_4$-alkyl, C$_3$-C$_8$-cycloalkyl, and C$_5$-C$_{10}$-hetaryl; or R$^c$ and R$^d$ together with the N-atom to which they are bonded form a 5- to 6-membered, saturated or unsaturated heterocycle.

In a more preferred embodiment of said use, in said compound of formula I,

R$^2$, R$^3$ and R$^4$ are independently of each other selected from H, halogen, OR$^a$, C(=O)OR$^a$, and C$_1$-C$_4$-alkyl;

or R$^3$ and R$^4$ together form a bridge, which forms together with the atoms to which R$^3$ and R$^4$ are bonded an annulated partly or fully unsaturated, or aromatic 5 to 10-membered carbocyclic ring, wherein the carbocyclic ring may be unsubstituted or may carry 1, 2, or 3 identical or different substituents selected from =O, halogen, CN, and OR$^a$, and wherein R$^a$ is H, C$_1$-C$_8$-alkyl, or C$_1$-C$_8$-haloalkyl.

In a further aspect, the present invention relates to a composition for use in reducing nitrification, comprising at least one compound of formula I as defined above and at least one carrier.

In a further aspect, the present invention relates to an agrochemical composition for use in reducing nitrification, comprising at least one compound of formula I as defined above and at least one carrier.

In a further aspect, the present invention relates to an agrochemical mixture comprising at least one fertilizer and at least one compound of formula I as defined above; or at least one fertilizer and a composition as mentioned above for use in reducing nitrification.

In a preferred embodiment, said compound of formula I as defined above is used for reducing nitrification in combination with a fertilizer. In a further specific embodiment, said compound of formula I as defined above is used for reducing nitrification in combination with a fertilizer in the form of an agrochemical mixture as mentioned above. In a further preferred embodiment, said reduction of nitrification as mentioned above occurs in or on a plant, in the root zone of a plant, in or on soil or soil substituents and/or at the locus where a plant is growing or is intended to grow.

In another aspect, the present invention relates to a method for reducing nitrification, comprising treating a plant growing on soil or soil substituents and/or the locus or soil or soil substituents where the plant is growing or is intended to grow with at least one compound of formula I as defined above, with a composition as defined above, or with an agrochemical composition as defined above. In a preferred embodiment of the method, the plant and/or the locus or soil or soil substituents where the plant is growing or is intended to grow is additionally provided with a fertilizer. In a further preferred embodiment of the method, the application of the nitrification inhibitor, i.e. the compound of formula I, and of said fertilizer is carried out simultaneously or with a time lag. In a particularly preferred embodiment, said time lag is an interval of 1 day, 2 days, 3 days, 4 days, 5, days, 6 days, 1 week, 2 weeks or 3 weeks. In case of application with a time lag, the nitrification inhibitor may be applied first and then the fertilizer. In a further preferred embodiment of the method, in a first step the nitrification inhibitor as defined above is applied to seeds, to a plant and/or to the locus where the plant is growing or is intended to grow and in a second step the fertilizer is applied to a plant and/or to the locus where the plant is growing or is intended to grow, wherein the application of a said nitrification inhibitor in the first step and the fertilizer in the second step is carried out with a time lag of at least 1 day, 2 days, 3 days, 4 days, 5, days, 6 days, 1 week, 2 weeks or 3 weeks. In other embodiments of application with a time lag, a fertilizer may be applied first and then the nitrification inhibitor as defined above may be applied. In a further preferred embodiment of the method, in a first step a fertilizer is applied to a plant and/or to the locus where the plant is growing or is intended to grow and in a second step the nitrification inhibitor as defined above is applied to seeds, to a plant and/or to the locus where the plant is growing or is intended to grow, wherein the application of a said fetilizer in the first step and said nitrification inhibitor in the second step is carried out with a time lag of at least 1 day, 2 days, 3 days, 4 days, 5, days, 6 days, 1 week, 2 weeks or 3 weeks.

In a preferred embodiment of the use, agrochemical mixture or method of the invention, said fertilizer is a solid or liquid ammonium-containing inorganic fertilizer such as an NPK fertilizer, ammonium nitrate, calcium ammonium nitrate, ammonium sulfate nitrate, ammonium sulfate or ammonium phosphate; a solid or liquid organic fertilizer such as liquid manure, semi-liquid manure, stable manure, biogas manure and straw manure, worm castings, compost, seaweed or guano, or an urea-containing fertilizer such as urea, formaldehyde urea, urea ammonium nitrate (UAN) solution, urea sulphur, urea based NPK-fertilizers, or urea ammonium sulfate.

In a further preferred embodiment of the use or method of the invention, said plant is an agricultural plant such as wheat, barley, oat, rye, soybean, corn, potatoes, oilseed rape, canola, sunflower, cotton, sugar cane, sugar beet, rice or a vegetable such as spinach, lettuce, asparagus, or cabbages; or sorghum; a silvicultural plant; an ornamental plant; or a horticultural plant, each in its natural or in a genetically modified form.

The compounds of formula I can be prepared by standard processes of organic chemistry. If R$^1$ is, e.g., C$_3$-C$_6$-alkynyl, the R$^1$-substituent may be introduced by reacting a compound of formula II with a compound of formula III, wherein LG represents a leaving group, according to the following scheme.

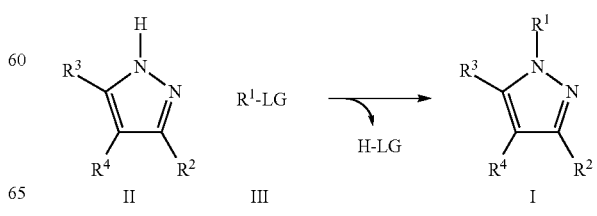

For example, unsubstituted pyrazole may be reacted with propargyl chloride or propargyl bromide in order to obtain 1-prop-2-ynylpyrazole.

The compounds of formula I, wherein $R^1$ is $C_3$-$C_6$-allenyl, are isomers of the compounds of formula I, wherein $R^1$ is $C_3$-$C_6$-alkynyl, and can be formed by methods known in the art (Diaz-Barrà et al., Synth. Comm. 1990, 20, pp. 2849-2853).

The synthesis of N-alkynyl- and N-allenylpyrazoles has further been described by M. I. Rodriguez-Franco et al. in Med. Chem. Ress. 2002, 11/6, pp. 333-344, by H. Reimlinger et al. in Chem. Ber. 1970, 103, pp. 1954-1959, and by M. I. Rodriguez-Franco et al. in Arch. Pharm. Pharm. Med. Chem. 2002, 7, pp. 339-346.

The substituents $R^2$, $R^3$, and $R^4$ may be introduced by standard reactions including aromatic substitution reactions.

A skilled person is aware that the substituents of the pyrazole compounds may also be introduced by using suitable precursors for the preparation of the pyrazoles.

Suitable methods for preparing pyrazole compounds are described in "Progress in Heterocyclic Chemistry", Vol. 27, G. W. Gribble, J. A. Joule, Elsevier, 2015, Chapter 5.4.2.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

The term "nitrification inhibitor" is to be understood in this context as a chemical substance which slows down or stops the nitrification process. Nitrification inhibitors accordingly retard the natural transformation of ammonium into nitrate, by inhibiting the activity of bacteria such as *Nitrosomonas* spp. The term "nitrification" as used herein is to be understood as the biological oxidation of ammonia ($NH_3$) or ammonium ($NH_4^+$) with oxygen into nitrite ($NO_2^-$) followed by the oxidation of these nitrites into nitrates ($NO_3^-$) by microorganisms. Besides nitrate ($NO_3^-$) nitrous oxide is also produced through nitrification. Nitrification is an important step in the nitrogen cycle in soil. The inhibition of nitrification may thus also reduce $N_2O$ losses. The term nitrification inhibitor is considered equivalent to the use of such a compound for inhibiting nitrification The term "compound(s) according to the invention", or "compounds of formula I" comprises the compound(s) as defined herein as well as a stereoisomer, salt, tautomer or N-oxide thereof. The term "compound(s) of the present invention" is to be understood as equivalent to the term "compound(s) according to the invention", therefore also comprising a stereoisomer, salt, tautomer or N-oxide thereof.

Depending on the substitution pattern, the compounds according to the invention may have one or more centers of chirality, in which case they are present as mixtures of enantiomers or diastereomers. The invention provides both the single pure enantiomers or pure diastereomers of the compounds according to the invention, and their mixtures and the use according to the invention of the pure enantiomers or pure diastereomers of the compounds according to the invention or their mixtures. Suitable compounds according to the invention also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula I, i.e. to single enantiomers or diastereomers, as well as to mixtures thereof.

The compounds of formula I may be amorphous or may exist in one or more different crystalline states (polymorphs) which may have different macroscopic properties such as stability or show different biological properties such as activities. The present invention relates to amorphous and crystalline compounds of formula I, mixtures of different crystalline states of the respective compound I, as well as amorphous or crystalline salts thereof.

Salts of the compounds of the formula I are preferably agriculturally acceptable salts. They can be formed in a customary manner, e.g. by reacting the compound with an acid of the anion in question if the compound of formula I has a basic functionality. Agriculturally useful salts of the compounds of formula I encompass especially the acid addition salts of those acids whose cations and anions, respectively, have no adverse effect on the mode of action of the compounds of formula I. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of formula I with an acid of the corresponding anion, preferably of hydrochloric acid, hydrobromic acid, sulfuric acid, phosphoric acid or nitric acid. Furthermore, salts of the compounds of formula I can be formed by alkylating the unsubstituted nitrogen atom of the pyrazole ring, so that a cation is formed, which may be present in the following two mesomeric forms $I^+_a$ and $I^+_b$. Typically, the anions then stem from the alkylating agents and may e.g. be chloride, bromide, iodide, sulfate, hydrogensulfate, methylsulfat, mesylate, triflate, or tosylate.

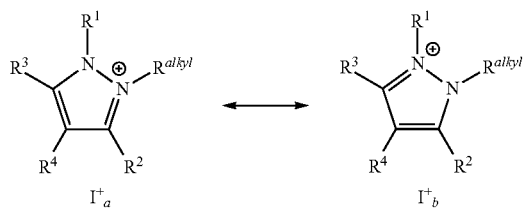

The term "N-oxide" includes any compound of formula I which has at least one tertiary nitrogen atom that is oxidized to an N-oxide moiety.

A skilled person is aware that the pyrazole moiety is an aromatic moiety, which may also be represented by a molecular formula as depicted below, wherein the circle represents the two double bonds and the lone pair at the N—$R^1$-nitrogen atom, which form the aromatic system.

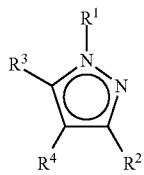

Similarly, also the cationic form of the pyrazole moiety may be represented by such a molecular formula, wherein the circle represents the two double bonds and the lone pair at the N—$R^1$-nitrogen atom, which form the aromatic system.

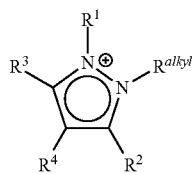

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein denotes in each case a straight-chain or branched alkyl group having usually from 1 to 8 carbon atoms, frequently from 1 to 6 carbon atoms, preferably 1 to 4 carbon atoms, more preferably from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein denotes in each case a straight-chain or branched alkyl group having usually from 1 to 8 carbon atoms, frequently from 1 to 6 carbon atoms, preferably from 1 to 4 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bonded via an oxygen atom and has usually from 1 to 8 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "haloalkoxy" as used herein denotes in each case a straight-chain or branched alkoxy group having from 1 to 10 carbon atoms, frequently from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2-dichloro-2-fluorethoxy, 2,2,2-trichloroethoxy, pentafluoroethoxy and the like.

The term "cycloalkyl" as used herein denotes in each case a monocyclic cycloaliphatic radical having usually from 3 to 8 or from 3 to 6 carbon atoms, such as cyclopropyl, cyclobutyl, cyclopentyl, cyclohexyl, cycloheptyl, and cyclooctyl.

The term "alkenyl" as used herein denotes in each case an at least singly unsaturated hydrocarbon radical, i.e. a hydrocarbon radical having at least one carbon-carbon double bond, having usually 2 to 8, frequently 2 to 6, preferably 2 to 4 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "alkynyl" as used herein denotes in each case a hydrocarbon radical having at least one carbon-carbon triple bond and having usually 2 to 8, e.g. 2 to 6, frequently 2 to 4, preferably 2 or 3 carbon atoms or 3 or 4 carbon atoms, e.g. ethynyl, propargyl (2-propyn-1-yl, also referred to as prop-2-yn-1-yl), 1-propyn-1-yl (also referred to as prop-1-yn-1-yl), 1-methylprop-2-yn-1-yl, 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like. As used herein, a "terminal alkynyl group" is an alkynyl group, wherein one of the two carbon atoms of the carbon-carbon triple bond is unsubstituted, i.e. bonded to one hydrogen atom. Examples for a terminal alkynyl group are propargyl (2-propyn-1-yl, also referred to as prop-2-yn-1-yl), i.e. a —CH₂—C≡CH group, 1-methylprop-2-yn-1-yl, i.e. a —CH(CH₃)—C≡CH group, and 3-butyn-1-yl (also referred to as but-3-yn-1-yl), i.e. a —CH₂—CH₂—C≡CH group.

The term "allenyl" as used herein denotes in each case a hydrocarbon radical having two cumulated double bonds, i.e. one carbon atom has double bonds with each of its two adjacent carbon centres (>C═C═C<moiety). Accordingly, an allenyl group has at least 3, preferably 3 to 6, more preferably 3 or 4 carbon atoms. As used herein, a "terminal allenyl group" is an allenyl group, wherein one carbon atom of the two carbon atoms, which are adjacent to the carbon atom with the two double bonds, is unsubstituted, i.e. bonded to two hydrogen atoms. Exemplary terminal allenyl groups according to the invention include, e.g., —CH═C═CH₂, —C(CH₃)═C═CH₂, and —CH₂—CH═C═CH₂. Preferred is C₃-allenyl, which is —CH═C═CH₂.

The term "carbocycle", "carbocyclic ring" or "carbocyclyl" includes, unless otherwise indicated, in general a 3- to 12-membered, preferably a 5- to 10-membered, more preferably a 6- or 10-membered monocyclic or bicyclic, preferably monocyclic ring comprising 3 to 12, preferably 5 to 10, more preferably 6 or 10 carbon atoms. Unless otherwise indicated, the carbocyclic ring may be saturated, partly or fully unsaturated, or aromatic. Preferred carbocyclic rings include benzene, cyclohexene, cyclohexane, and 1,2,3,4-tetrahydronaphthale.

The term "heterocycle", "heterocyclic ring" or "heterocyclyl" includes, unless otherwise indicated, in general 3- to 12-membered, preferably a 5- to 10-membered, more preferably 5- or 6-membered or a 10-membered monocyclic or bicyclic heterocyclic ring. Unless otherwise indicated, the heterocyclic ring may be saturated, partly or fully unsaturated, or aromatic. The heterocyclic rings usually comprise 1, 2, 3, 4 or 5, preferably 1, 2 or 3 heteroatoms selected from N, O and S as ring members, where S-atoms as ring members may be present as S, SO or SO₂. Examples of 5- or 6-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S.oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

The term "aryl" includes monocyclic or bicyclic, preferably monocyclic aromatic radicals comprising 6 to 10 carbon atoms, preferably 6 carbon atoms. Exemplary aryl radicals include naphthalenyl and phenyl. A preferred aryl radical is phenyl.

The term "hetaryl" includes monocyclic or bicyclic 5 to 10-membered, e.g. 5-, or 6-, or 9- or 10-membered heteroaromatic radicals, preferably monocyclic 5- or 6-membered heteroaromatic radicals comprising as ring members 1, 2, 3 or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl.

As has been set out above, the present invention concerns in one aspect the use of a compound of formula I

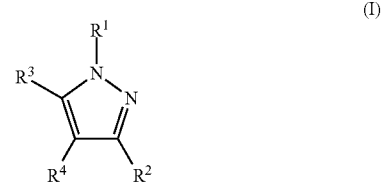

(I)

or a stereoisomer, salt, tautomer or N-oxide thereof as a nitrification inhibitor, wherein $R^1$ is $C_3$-$C_6$-alkynyl, with the proviso that if $R^1$ is $C_3$-alkynyl, it is propargyl, or $C_3$-$C_6$-allenyl, wherein the C-atoms of these groups may in each case be unsubstituted or may carry 1, 2, or 3 identical or different substituents selected from halogen, CN, $OR^a$, $NO_2$, $NR^cR^d$, $NR^b(C═O)R^a$, $C(═O)R^a$, $C(═O)OR^a$, $C(═O)NR^cR^d$, $S(O)_mR^a$, and $S(O)_mNR^cR^d$;

and wherein $R^2$, $R^3$ and $R^4$ are independently of each other selected from H, halogen, CN, $OR^a$, $NO_2$, $NR^cR^d$, $NR^b(C═O)R^a$, $C(═O)R^a$, $C(═O)OR^a$, $C(═O)NR^cR^d$, $S(O)_mR^a$, $S(O)_mNR^cR^d$;

$C_1$-$C_8$-alkyl, $C_3$-$C_8$-cycloalkyl, $C_2$-$C_8$-alkenyl, $C_2$-$C_8$-alkynyl, wherein the C-atoms of these groups may in each case be unsubstituted or may carry 1, 2, or 3 identical or different substituents selected from halogen, CN, $OR^a$, $NO_2$, $NR^cR^d$, $NR^b(C═O)R^a$, $C(═O)R^a$, $C(═O)OR^a$, $C(═O)NR^cR^d$, $S(O)_mR^a$, and $S(O)_mNR^cR^d$;

$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, $OR^a$, $C_1$-$C_4$-alkyl, $C_1$-$C_4$-haloalkyl, $C_2$-$C_4$-alkenyl, and $C_2$-$C_4$-alkynyl;

or $R^3$ and $R^4$ together form a bridge, which forms together with the atoms to which $R^3$ and $R^4$ are bonded an annulated partly or fully unsaturated, or aromatic 5 to 10-membered carbocyclic or heterocyclic ring, wherein the heterocyclic ring may carry 1, 2, or 3 heteroatoms being selected from O, S, and N, of which S and/or N may optionally be oxidized, and wherein the carbocyclic or heterocyclic ring may be unsubstituted or may carry 1, 2, 3, 4, or 5 identical or different substituents selected from ═O, halogen, CN, $OR^a$, $NO_2$, $NR^cR^d$, $NR^b(C═O)R^a$, $C(═O)R^a$, $C(═O)OR^a$, $C(═O)NR^cR^d$, $O(C═O)NR^cR^d$, $C_1$-$C_4$-alkyl, $C_1$-$C_4$-haloalkyl, $C_6$-$C_{10}$-aryl, $C_5$-$C_{10}$-hetaryl, $C_5$-$C_{10}$-carbocyclyl, and $C_5$-$C_{10}$-heterocyclyl, wherein the $C_6$-$C_{10}$-aryl, $C_5$-$C_{10}$-hetaryl, $C_5$-$C_{10}$-carbocyclyl, and $C_5$-$C_{10}$-heterocyclyl moieties may be unsubstituted or may carry 1, 2, 3, 4, or 5 identical or different substituents selected from =O, halogen, CN, $C_1$-$C_4$-alkyl, and $C_1$-$C_4$-haloalkyl;

or $R^2$ and $R^4$ together form a bridge, which forms together with the atoms to which $R^2$ and $R^4$ are bonded an annulated partly or fully unsaturated, or aromatic 5 to 10-membered carbocyclic or heterocyclic ring, wherein the heterocyclic ring may carry 1, 2, or 3 heteroatoms being selected from O, S, and N, of which S and/or N may optionally be oxidized, and wherein the carbocyclic or heterocyclic ring may be unsubstituted or may carry 1, 2, 3, 4, or 5 identical or different substituents selected from =O, halogen, CN, $OR^a$, $NO_2$, $NR^cR^d$, $NR^b(C=O)R^a$, $C(=O)R^a$, $C(=O)OR^a$, $C(=O)NR^cR^d$, $O(C=O)NR^cR^d$, $C_1$-$C_4$-alkyl, $C_1$-$C_4$-haloalkyl, $C_6$-$C_{10}$-aryl, $C_5$-$C_{10}$-hetaryl, $C_5$-$C_{10}$-carbocyclyl, and $C_5$-$C_{10}$-heterocyclyl, wherein the $C_6$-$C_{10}$-aryl, $C_5$-$C_{10}$-hetaryl, $C_5$-$C_{10}$-carbocyclyl, and $C_5$-$C_{10}$-heterocyclyl moieties may be unsubstituted or may carry 1, 2, 3, 4, or 5 identical or different substituents selected from =O, halogen, CN, $C_1$-$C_4$-alkyl, and $C_1$-$C_4$-haloalkyl;

and wherein $R^a$ is H, $C_1$-$C_8$-alkyl, $C_1$-$C_8$-haloalkyl, $C_2$-$C_8$-alkenyl, $C_2$-$C_8$-alkynyl;

$C_5$-$C_{10}$-hetaryl or $C_6$-$C_{10}$-aryl, wherein the $C_5$-$C_{10}$-hetaryl or $C_6$-$C_{10}$-aryl moieties may in each case be unsubstituted or may carry 1, 2, 3, 4, or 5 identical or different substituents selected from halogen, CN, OH, $C_1$-$C_4$-alkyl, $C_1$-$C_4$-alkoxy, $C_1$-$C_4$-haloalkyl, $C_2$-$C_4$-alkenyl, $C_2$-$C_4$-alkynyl, $C_5$-$C_6$-hetaryl and $C_6$-aryl, wherein said $C_5$-$C_6$-hetaryl and $C_6$-aryl moieties may be unsubstituted or may carry 1, 2, 3, 4, or 5 substituents selected from halogen, CN, OH, $C_1$-$C_4$-alkyl, $C_1$-$C_4$-alkoxy, $C_1$-$C_4$-haloalkyl, $C_2$-$C_4$-alkenyl, and $C_2$-$C_4$-alkynyl;

$R^b$ is H, $C_1$-$C_4$-alkyl, $C_3$-$C_8$-cycloalkyl, $C_2$-$C_4$-alkenyl, $C_2$-$C_8$-alkynyl, or $C_6$-$C_{10}$-aryl; and $R^c$ and $R^d$ are independently of each other selected from the group consisting of H, $C_1$-$C_4$-alkyl, $C_1$-$C_4$-haloalkyl, $C_3$-$C_8$-cycloalkyl, $C_6$-$C_{10}$-aryl, and $C_5$-$C_{10}$-hetaryl; or $R^c$ and $R^d$ together with the N-atom to which they are bonded form a 5- to 6-membered, saturated or unsaturated heterocycle, which may carry a further heteroatom being selected from O, S, and N as a ring member atom, of which S and/or N may optionally be oxidized, and wherein the heterocyclic ring may be unsubstituted or may carry 1, 2, 3, 4, or 5 substituents, which are independently selected from halogen, CN, OH, $NO_2$, $C_1$-$C_4$-alkyl, $C_1$-$C_4$-haloalkyl, $C_1$-$C_4$-alkoxy, and $C_1$-$C_4$-haloalkoxy;

and wherein m is 0, 1, or 2.

In one preferred embodiment of said use, in the compound of formula I as defined above, $R^1$ is a terminal $C_3$-$C_4$-alkynyl group, preferably propargyl. These compounds correspond to compounds of formula I.1a, wherein $R^1$-1a represents a terminal $C_3$-$C_4$-alkynyl group, preferably propargyl.

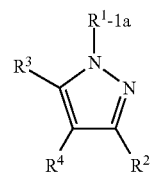

(I.1a)

Preferably, the compound of formula I is a compound of formula I.1a, wherein $R^1$-1a is propargyl.

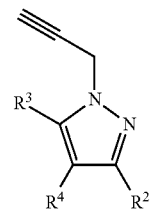

(I.1a with $R^1$-1a = propargyl)

In one preferred embodiment of said use, in the compound of formula I as defined above, $R^1$ is a terminal $C_3$-$C_4$-allenyl group, preferably $C_3$-allenyl. These compounds correspond to compounds of formula I.1b, wherein $R^1$-1b represents a terminal $C_3$-$C_4$-allenyl group, preferably $C_3$-allenyl.

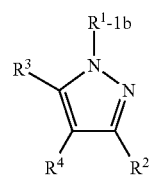

(I.1b)

Preferably, the compound of formula I is a compound of compound of formula I.1b, wherein $R^1$-1b is $C_3$-allenyl.

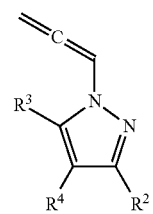

(I.1b with $R^1$-1b = $C_3$-allenyl)

In one preferred embodiment of said use, in the compound of formula I as defined above, $R^2$, $R^3$ and $R^4$ are independently of each other selected from H, halogen, CN, $OR^a$, $NO_2$, $NR^cR^d$, $NR^b(C=O)R^a$, $C(=O)R^a$, $C(=O)OR^a$, $C(=O)NR^cR^d$, $S(O)_mR^a$, $S(O)_mNR^cR^d$;

$C_1$-$C_8$-alkyl, $C_3$-$C_8$-cycloalkyl, $C_2$-$C_8$-alkenyl, $C_2$-$C_8$-alkynyl, wherein the C-atoms of these groups may in each case be unsubstituted or may carry 1, 2, or 3 identical or different substituents selected from halogen, CN, $OR^a$, $NO_2$, $NR^cR^d$, $NR^b(C=O)R^a$, $C(=O)R^a$, $C(=O)OR^a$, $C(=O)NR^cR^d$, $S(O)_mR^a$, and $S(O)_mNR^cR^d$;

$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, $OR^a$, $C_1$-$C_4$-alkyl, $C_1$-$C_4$-haloalkyl, $C_2$-$C_4$-alkenyl, and $C_2$-$C_4$-alkynyl;

wherein $R^a$, $R^b$, $R^c$, and $R^d$ are as defined above.

In a more preferred embodiment of said use, in the compound of formula I as defined above, $R^2$, $R^3$ and $R^4$ are independently of each other selected from H, halogen, $OR^a$, $C(=O)OR^a$, and $C_1$-$C_4$-alkyl, wherein $R^a$ is H, $C_1$-$C_8$-alkyl, or $C_1$-$C_8$-haloalkyl.

These compounds correspond to compounds of formula I.A, wherein $R^2$-A, $R^3$-A, and $R^4$-A represent the $R^2$, $R^3$, and $R^4$ substituents as defined above.

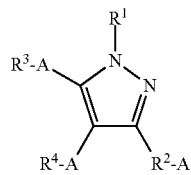

(I.A)

In one preferred embodiment of said use, in the compound of formula I as defined above, $R^2$ is selected from H, halogen, CN, $OR^a$, $NO_2$, $NR^cR^d$, $NR^b(C=O)R^a$, $C(=O)R^a$, $C(=O)OR^a$, $C(=O)NR^cR^d$, $S(O)_mR^a$, $S(O)_mNR^cR^d$;

$C_1$-$C_8$-alkyl, $C_3$-$C_8$-cycloalkyl, $C_2$-$C_8$-alkenyl, $C_2$-$C_8$-alkynyl, wherein the C-atoms of these groups may in each case be unsubstituted or may carry 1, 2, or 3 identical or different substituents selected from halogen, CN, $OR^a$, $NO_2$, $NR^cR^d$, $NR^b(C=O)R^a$, $C(=O)R^a$, $C(=O)OR^a$, $C(=O)NR^cR^d$, $S(O)_mR^a$, and $S(O)_mNR^cR^d$;

$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, $OR^a$, $C_1$-$C_4$-alkyl, $C_1$-$C_4$-haloalkyl, $C_2$-$C_4$-alkenyl, and $C_2$-$C_4$-alkynyl;

and $R^3$ and $R^4$ together form a bridge, which forms together with the atoms to which $R^3$ and $R^4$ are bonded an annulated partly or fully unsaturated, or aromatic 5 to 10-membered carbocyclic or heterocyclic ring, wherein the heterocyclic ring may carry 1, 2, or 3 heteroatoms being selected from O, S, and N, of which S and/or N may optionally be oxidized, and wherein the carbocyclic or heterocyclic ring may be unsubstituted or may carry 1, 2, 3, 4, or 5 identical or different substituents selected from =O, halogen, CN, $OR^a$, $NO_2$, $NR^cR^d$, $NR^b(C=O)R^a$, $C(=O)R^a$, $C(=O)OR^a$, $C(=O)NR^cR^d$, $O(C=O)NR^cR^d$, $C_1$-$C_4$-alkyl, $C_1$-$C_4$-haloalkyl, $C_6$-$C_{10}$-aryl, $C_5$-$C_{10}$-hetaryl, $C_5$-$C_{10}$-carbocyclyl, and $C_5$-$C_{10}$-heterocyclyl, wherein the $C_6$-$C_{10}$-aryl, $C_5$-$C_{10}$-hetaryl, $C_5$-$C_{10}$-carbocyclyl, and $C_5$-$C_{10}$-heterocyclyl moieties may be unsubstituted or may carry 1, 2, 3, 4, or 5 identical or different substituents selected from =O, halogen, CN, $C_1$-$C_4$-alkyl, and $C_1$-$C_4$-haloalkyl, wherein $R^a$, $R^b$, $R^c$, and $R^d$ are as defined above.

In a more preferred embodiment, $R^2$ is selected from H, halogen, $OR^a$, $C(=O)OR^a$, and $C_1$-$C_4$-alkyl;

and $R^3$ and $R^4$ together form a bridge, which forms together with the atoms to which $R^3$ and $R^4$ are bonded an annulated partly or fully unsaturated, or aromatic 5 to 10-membered carbocyclic ring, wherein the carbocyclic ring may be unsubstituted or may carry 1, 2, or 3 identical or different substituents selected from =O, halogen, CN, and $OR^a$, wherein $R^a$ is H, $C_1$-$C_8$-alkyl, or $C_1$-$C_8$-haloalkyl.

These compounds correspond to compounds of formula I.B, wherein $R^2$—B represents a $R^2$-substituent as defined above, and $R^3$—B and $R^4$—B together represent a $R^3$-$R^4$-bridge as defined above.

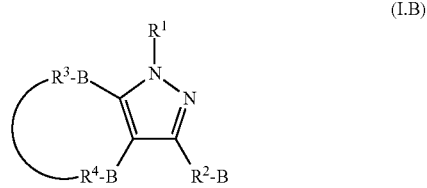

(I.B)

In one preferred embodiment of said use, in the compound of formula I as defined above, $R^3$ is selected from H, halogen, CN, $OR^a$, $NO_2$, $NR^cR^d$, $NR^b(C=O)R^a$, $C(=O)R^a$, $C(=O)OR^a$, $C(=O)NR^cR^d$, $S(O)_mR^a$, $S(O)_mNR^cR^d$;

$C_1$-$C_8$-alkyl, $C_3$-$C_8$-cycloalkyl, $C_2$-$C_8$-alkenyl, $C_2$-$C_8$-alkynyl, wherein the C-atoms of these groups may in each case be unsubstituted or may carry 1, 2, or 3 identical or different substituents selected from halogen, CN, $OR^a$, $NO_2$, $NR^cR^d$, $NR^b(C=O)R^a$, $C(=O)R^a$, $C(=O)OR^a$, $C(=O)NR^cR^d$, $S(O)_mR^a$, and $S(O)_mNR^cR^d$;

$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, $OR^a$, $C_1$-$C_4$-alkyl, $C_1$-$C_4$-haloalkyl, $C_2$-$C_4$-alkenyl, and $C_2$-$C_4$-alkynyl;

and $R^2$ and $R^4$ together form a bridge, which forms together with the atoms to which $R^2$ and $R^4$ are bonded an annulated partly or fully unsaturated, or aromatic 5 to 10-membered carbocyclic or heterocyclic ring, wherein the heterocyclic ring may carry 1, 2, or 3 heteroatoms being selected from O, S, and N, of which S and/or N may optionally be oxidized, and wherein the carbocyclic or heterocyclic ring may be unsubstituted or may carry 1, 2, 3, 4, or 5 identical or different substituents selected from =O, halogen, CN, $OR^a$, $NO_2$, $NR^cR^d$, $NR^b(C=O)R^a$, $C(=O)R^a$, $C(=O)OR^a$, $C(=O)NR^cR^d$, $O(C=O)NR^cR^d$, $C_1$-$C_4$-alkyl, $C_1$-$C_4$-haloalkyl, $C_6$-$C_{10}$-aryl, $C_5$-$C_{10}$-hetaryl, $C_5$-$C_{10}$-carbocyclyl, and $C_5$-$C_{10}$-heterocyclyl, wherein the $C_6$-$C_{10}$-aryl, $C_5$-$C_{10}$-hetaryl, $C_5$-$C_{10}$-carbocyclyl, and $C_5$-$C_{10}$-heterocyclyl moieties may be unsubstituted or may carry 1, 2, 3, 4, or 5 identical or different substituents selected from =O, halogen, CN, $C_1$-$C_4$-alkyl, and $C_1$-$C_4$-haloalkyl, wherein $R^a$, $R^b$, $R^c$, and $R^d$ are as defined above.

In a more preferred embodiment, $R^3$ is selected from H, halogen, $OR^a$, $C(=O)OR^a$, and $C_1$-$C_4$-alkyl;

and $R^2$ and $R^4$ together form a bridge, which forms together with the atoms to which $R^2$ and $R^4$ are bonded an annulated partly or fully unsaturated, or aromatic 5 to 10-membered carbocyclic ring, wherein the carbocyclic ring may be unsubstituted or may carry 1, 2, or 3 identical or different substituents selected from =O, halogen, CN, and $OR^a$, wherein $R^a$ is H, $C_1$-$C_8$-alkyl, or $C_1$-$C_8$-haloalkyl.

These compounds correspond to compounds of formula I.C, wherein $R^3$—C represents a $R^3$-substituent as defined above, and $R^2$—C and $R^4$—C together represent a $R^2$-$R^4$-bridge as defined above.

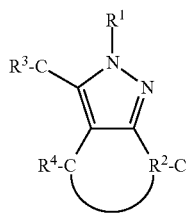

(I.C)

In one particularly preferred embodiment of said use, in the compound of formula I, $R^1$ is $R^1$-1a, and $R^2$, $R^3$ and $R^4$ correspond to $R^2$-A, $R^3$-A, and $R^4$-A. These compounds correspond to compounds of formula I.1a.A.

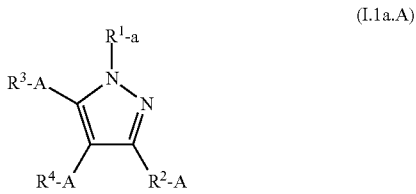

(I.1a.A)

Preferred compounds include compounds of formula I.1a.A with $R^1$-1a=propargyl.

In the compounds of formula I.1a.A, preferably in the compounds of formula I.1a.A with $R^1$-1a=propargyl, $R^2$-A, $R^3$-A, and $R^4$-A are most preferably independently selected from H, halogen, CN, $OR^a$, $C(=O)R^a$, $C(=O)OR^a$, $C(=O)NR^cR^d$;

$C_1$-$C_8$-alkyl, wherein the C-atoms may be unsubstituted or may carry 1, 2, or 3 identical or different substituents selected from halogen, CN, and $OR^a$;

$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, $OR^a$, $C_1$-$C_4$-alkyl, $C_1$-$C_4$-haloalkyl, and $C_2$-$C_4$-alkynyl;

and particularly preferably selected from

H, halogen, $OR^a$, $C(=O)OR^a$, and $C_1$-$C_4$-alkyl, wherein $R^a$ is H, $C_1$-$C_8$-alkyl, or $C_1$-$C_8$-haloalkyl.

In one particularly preferred embodiment of said use, in the compound of formula I, $R^1$ is $R^1$-1b, and $R^2$, $R^3$ and $R^4$ correspond to $R^2$-A, $R^3$-A, and $R^4$-A. These compounds correspond to compounds of formula I.1b.A.

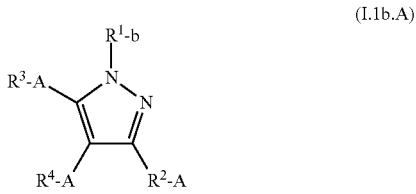

(I.1b.A)

Preferred compounds include compounds of formula I.1b.A with $R^1$-1b=$C_3$-allenyl.

In the compounds of formula I.1b.A, preferably in the compounds of formula I.1b.A with $R^1$-1b=$C_3$-allenyl, $R^2$-A, $R^3$-A, and $R^4$-A are most preferably independently selected from H, halogen, CN, $OR^a$, $C(=O)R^a$, $C(=O)OR^a$, $C(=O)NR^cR^d$;

$C_1$-$C_8$-alkyl, wherein the C-atoms may be unsubstituted or may carry 1, 2, or 3 identical or different substituents selected from halogen, CN, and $OR^a$;

$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, $OR^a$, $C_1$-$C_4$-alkyl, $C_1$-$C_4$-haloalkyl, and $C_2$-$C_4$-alkynyl;

and particularly preferably selected from

H, halogen, $OR^a$, $C(=O)OR^a$, and $C_1$-$C_4$-alkyl, wherein $R^a$ is H, $C_1$-$C_8$-alkyl, or $C_1$-$C_8$-haloalkyl.

In one particularly preferred embodiment of said use, in the compound of formula I, $R^1$ is $R^1$-1a, and $R^2$, $R^3$ and $R^4$ correspond to $R^2$—B, $R^3$—B, and $R^4$—B. These compounds correspond to compounds of formula I.1a.B.

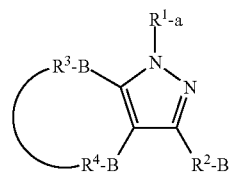

(I.1a.B)

Preferred compounds include compounds of formula I.1a.B with $R^1$-1a=propargyl.

In the compounds of formula I.1a.B, preferably in the compounds of formula I.1a.B with $R^1$-1a=propargyl, $R^2$—B is most preferably selected from H, halogen, CN, $OR^a$, $C(=O)R^a$, $C(=O)OR^a$, $C(=O)NR^cR^d$;

$C_1$-$C_8$-alkyl, wherein the C-atoms may be unsubstituted or may carry 1, 2, or 3 identical or different substituents selected from halogen, CN, and $OR^a$;

$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, $OR^a$, $C_1$-$C_4$-alkyl, $C_1$-$C_4$-haloalkyl, and $C_2$-$C_4$-alkynyl; and $R^3$—B and $R^4$—B most preferably together form a bridge, which forms together with the atoms to which $R^3$—B and $R^4$—B are bonded an annulated partly or fully unsaturated, or aromatic 5 to 10-membered carbocyclic ring, wherein the carbocyclic ring may be unsubstituted or may carry 1, 2, 3, 4, or 5 identical or different substituents selected from =O, halogen, CN, $OR^a$, $O(C=O)NR^cR^d$, $C_5$-$C_{10}$-hetaryl, and $C_5$-$C_{10}$-heterocyclyl, wherein the $C_5$-$C_{10}$-hetaryl, and $C_5$-$C_{10}$-heterocyclyl moieties may be unsubstituted or may carry 1, 2, 3, 4, or 5 identical or different substituents selected from =O, halogen, CN, and $C_1$-$C_4$-haloalkyl;

and particularly preferably $R^2$—B is selected from H, halogen, $OR^a$, $C(=O)OR^a$, and $C_1$-$C_4$-alkyl; and $R^3$—B and $R^4$—B together form a bridge, which forms together with the atoms to which $R^3$—B and $R^4$—B are bonded an annulated partly or fully unsaturated, or aromatic 5 to 10-membered carbocyclic ring, wherein the carbocyclic ring may be unsubstituted or may carry 1, 2, or 3 identical or different substituents selected from =O, halogen, CN, and $OR^a$; wherein $R^a$ is H, $C_1$-$C_8$-alkyl, or $C_1$-$C_8$-haloalkyl.

In one particularly preferred embodiment of said use, in the compound of formula I, $R^1$ is $R^1$-1b, and $R^2$, $R^3$ and $R^4$ correspond to $R^2$—B, $R^3$—B, and $R^4$—B. These compounds correspond to compounds of formula I.1b.B.

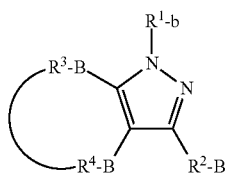
(I.1b.B)

Preferred compounds include compounds of formula I.1b.B with $R^1$-1b=$C_3$-allenyl.

In the compounds of formula I.1b.B, preferably in the compounds of formula I.1b.B with $R^1$-1b=$C_3$-allenyl, $R^2$—B is most preferably selected from H, halogen, CN, $OR^a$, $C(=O)R^a$, $C(=O)OR^a$, $C(=O)NR^cR^d$;

$C_1$-$C_8$-alkyl, wherein the C-atoms may be unsubstituted or may carry 1, 2, or 3 identical or different substituents selected from halogen, CN, and $OR^a$;

$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, $OR^a$, $C_1$-$C_4$-alkyl, $C_1$-$C_4$-haloalkyl, and $C_2$-$C_4$-alkynyl; and $R^3$—B and $R^4$—B most preferably together form a bridge, which forms together with the atoms to which $R^3$—B and $R^4$—B are bonded an annulated partly or fully unsaturated, or aromatic 5 to 10-membered carbocyclic ring, wherein the carbocyclic ring may be unsubstituted or may carry 1, 2, 3, 4, or 5 identical or different substituents selected from =O, halogen, CN, $OR^a$, $O(C=O)NR^cR^d$, $C_5$-$C_{10}$-hetaryl, and $C_5$-$C_{10}$-heterocyclyl, wherein the $C_5$-$C_{10}$-hetaryl, and $C_5$-$C_{10}$-heterocyclyl moieties may be unsubstituted or may carry 1, 2, 3, 4, or 5 identical or different substituents selected from =O, halogen, CN, and $C_1$-$C_4$-haloalkyl;

and particularly preferably $R^2$—B is selected from H, halogen, $OR^a$, $C(=O)OR^a$, and $C_1$-$C_4$-alkyl; and $R^3$—B and $R^4$—B together form a bridge, which forms together with the atoms to which $R^3$—B and $R^4$—B are bonded an annulated partly or fully unsaturated, or aromatic 5 to 10-membered carbocyclic ring, wherein the carbocyclic ring may be unsubstituted or may carry 1, 2, or 3 identical or different substituents selected from =O, halogen, CN, and $OR^a$; wherein $R^a$ is H, $C_1$-$C_8$-alkyl, or $C_1$-$C_8$-haloalkyl.

In one particularly preferred embodiment of said use, in the compound of formula I, $R^1$ is $R^1$-1a, and $R^2$, $R^3$ and $R^4$ correspond to $R^2$—C, $R^3$—C, and $R^4$—C. These compounds correspond to compounds of formula I.1a.C.

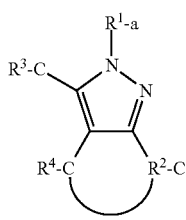
(I.1a.C)

Preferred compounds include compounds of formula I.1a.C with $R^1$-1a=propargyl.

In the compounds of formula I.1a.C, preferably in the compounds of formula I.1a.C with $R^1$-1a=propargyl, $R^3$—C is most preferably selected from H, halogen, CN, $OR^a$, $C(=O)R^a$, $C(=O)OR^a$, $C(=O)NR^cR^d$;

$C_1$-$C_8$-alkyl, wherein the C-atoms may be unsubstituted or may carry 1, 2, or 3 identical or different substituents selected from halogen, CN, and $OR^a$;

$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, $OR^a$, $C_1$-$C_4$-alkyl, $C_1$-$C_4$-haloalkyl, and $C_2$-$C_4$-alkynyl; and $R^2$—C and $R^4$—C most preferably together form a bridge, which forms together with the atoms to which $R^2$—C and $R^4$—C are bonded an annulated partly or fully unsaturated, or aromatic 5 to 10-membered carbocyclic ring, wherein the carbocyclic ring may be unsubstituted or may carry 1, 2, 3, 4, or 5 identical or different substituents selected from =O, halogen, CN, $OR^a$, $O(C=O)NR^cR^d$, $C_5$-$C_{10}$-hetaryl, and $C_5$-$C_{10}$-heterocyclyl, wherein the $C_5$-$C_{10}$-hetaryl, and $C_5$-$C_{10}$-heterocyclyl moieties may be unsubstituted or may carry 1, 2, 3, 4, or 5 identical or different substituents selected from =O, halogen, CN, and $C_1$-$C_4$-haloalkyl;

and particularly preferably $R^3$—C is selected from H, halogen, $OR^a$, $C(=O)OR^a$, and $C_1$-$C_4$-alkyl; and $R^2$—C and $R^4$—C together form a bridge, which forms together with the atoms to which $R^2$—C and $R^4$—C are bonded an annulated partly or fully unsaturated, or aromatic 5 to 10-membered carbocyclic ring, wherein the carbocyclic ring may be unsubstituted or may carry 1, 2, or 3 identical or different substituents selected from =O, halogen, CN, and $OR^a$; wherein $R^a$ is H, $C_1$-$C_8$-alkyl, or $C_1$-$C_8$-haloalkyl.

In one particularly preferred embodiment of said use, in the compound of formula I, $R^1$ is $R^1$-1b, and $R^2$, $R^3$ and $R^4$ correspond to $R^2$—C, $R^3$—C, and $R^4$—C. These compounds correspond to compounds of formula I.1b.C.

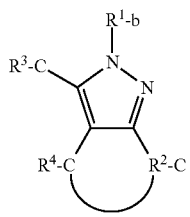
(I.1b.C)

Preferred compounds include compounds of formula I.1b.C with $R^1$-1b=$C_3$-allenyl.

In the compounds of formula I.1b.C, preferably in the compounds of formula I.1b.C with $R^1$-1b=$C_3$-allenyl, $R^3$—C is most preferably selected from H, halogen, CN, $OR^a$, $C(=O)R^a$, $C(=O)OR^a$, $C(=O)NR^cR^d$;

$C_1$-$C_8$-alkyl, wherein the C-atoms may be unsubstituted or may carry 1, 2, or 3 identical or different substituents selected from halogen, CN, and $OR^a$;

$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, $OR^a$, $C_1$-$C_4$-alkyl, $C_1$-$C_4$-haloalkyl, and $C_2$-$C_4$-alkynyl; and $R^2$—C and $R^4$—C most preferably together form a bridge, which forms together with the atoms to which $R^2$—C and $R^4$—C are bonded an annulated partly or fully unsaturated, or aromatic 5 to 10-membered carbocyclic ring, wherein the carbocyclic ring may be unsubstituted or may carry 1, 2, 3, 4, or 5 identical or different substituents selected from =O, halogen, CN, OR$^a$, O(C=O)NR$^c$R$^d$, $C_5$-$C_{10}$-hetaryl, and $C_5$-$C_{10}$-heterocyclyl, wherein the $C_5$-$C_{10}$-hetaryl, and $C_5$-$C_{10}$-heterocyclyl moieties may be unsubstituted or may carry 1, 2, 3, 4, or 5 identical or different substituents selected from =O, halogen, CN, and $C_1$-$C_4$-haloalkyl;

and particularly preferably R$^3$—C is selected from H, halogen, OR$^a$, C(=O)OR$^a$, and $C_1$-$C_4$-alkyl; and R$^2$—C and R$^4$—C together form a bridge, which forms together with the atoms to which R$^2$—C and R$^4$—C are bonded an annulated partly or fully unsaturated, or aromatic 5 to 10-membered carbocyclic ring, wherein the carbocyclic ring may be unsubstituted or may carry 1, 2, or 3 identical or different substituents selected from =O, halogen, CN, and OR$^a$; wherein R$^a$ is H, $C_1$-$C_8$-alkyl, or $C_1$-$C_8$-haloalkyl.

In one particularly preferred embodiment of said use, the compound of formula I is a compound of formula I.1a.A as defined above or a compounds of formula I.1b.A as defined above.

Thus, the present invention relates in a preferred embodiment to the use of a compound of formula I, preferably a compound of formula I.1a or I.1b, as a nitrification inhibitor, wherein R$^2$, R$^3$ and R$^4$ are independently of each other selected from
H, halogen, CN, OR$^a$, C(=O)R$^a$, C(=O)OR$^a$, C(=O)NR$^c$R$^d$;
$C_1$-$C_8$-alkyl, wherein the C-atoms may be unsubstituted or may carry 1, 2, or 3 identical or different substituents selected from halogen, CN, and OR$^a$;
$C_6$-$C_{10}$-aryl, and $C_5$-$C_{10}$-hetaryl, wherein the aromatic moieties may in each case be unsubstituted or may carry 1, 2, 3, 4, or 5 identical or different substituents selected from halogen, CN, OR$^a$, $C_1$-$C_4$-alkyl, $C_1$-$C_4$-haloalkyl, and $C_2$-$C_4$-alkynyl;
or R$^3$ and R$^4$ together form a bridge, which forms together with the atoms to which R$^3$ and R$^4$ are bonded an annulated partly or fully unsaturated, or aromatic 5 to 10-membered carbocyclic ring, wherein the carbocyclic ring may be unsubstituted or may carry 1, 2, 3, 4, or 5 identical or different substituents selected from =O, halogen, CN, OR$^a$, O(C=O)NR$^c$R$^d$, $C_5$-$C_{10}$-hetaryl, and $C_5$-$C_{10}$-heterocyclyl, wherein the $C_5$-$C_{10}$-hetaryl, and $C_5$-$C_{10}$-heterocyclyl moieties may be unsubstituted or may carry 1, 2, 3, 4, or 5 identical or different substituents selected from =O, halogen, CN, and $C_1$-$C_4$-haloalkyl;
or R$^2$ and R$^4$ together form a bridge, which forms together with the atoms to which R$^2$ and R$^4$ are bonded an annulated partly or fully unsaturated, or aromatic 5 to 10-membered carbocyclic ring, wherein the carbocyclic ring may be unsubstituted or may carry 1, 2, 3, 4, or 5 identical or different substituents selected from =O, halogen, CN, OR$^a$, O(C=O)NR$^c$R$^d$, $C_5$-$C_{10}$-hetaryl, and $C_5$-$C_{10}$-heterocyclyl, wherein the $C_5$-$C_{10}$-hetaryl, and $C_5$-$C_{10}$-heterocyclyl moieties may be unsubstituted or may carry 1, 2, 3, 4, or 5 identical or different substituents selected from =O, halogen, CN, and $C_1$-$C_4$-haloalkyl;
and wherein
R$^a$ is H, $C_1$-$C_8$-alkyl, $C_1$-$C_8$-haloalkyl, $C_2$-$C_8$-alkynyl;
$C_5$-$C_{10}$-hetaryl or $C_6$-$C_{10}$-aryl, wherein the $C_5$-$C_{10}$-hetaryl or $C_6$-$C_{10}$-aryl moieties may in each case be unsubstituted or may carry 1, 2, 3, 4, or 5 identical or different substituents selected from halogen, CN, $C_1$-$C_4$-alkyl, $C_1$-$C_4$-haloalkyl, $C_2$-$C_4$-alkynyl, $C_5$-$C_6$-hetaryl and $C_6$-aryl, wherein said $C_5$-$C_6$-hetaryl and $C_6$-aryl moieties may be unsubstituted or may carry 1, 2, 3, 4, or 5 substituents selected from halogen, CN, $C_1$-$C_4$-alkyl, $C_1$-$C_4$-haloalkyl, and $C_2$-$C_4$-alkynyl; and
R$^c$ and R$^d$ are independently of each other selected from the group consisting of H, $C_1$-$C_4$-alkyl, $C_3$-$C_8$-cycloalkyl, and $C_5$-$C_{10}$-hetaryl; or
R$^c$ and R$^d$ together with the N-atom to which they are bonded form a 5- to 6-membered, saturated or unsaturated heterocycle.

In a particularly preferred embodiment, the present invention relates to the use of a compound of formula I, preferably a compound of formula I.1a or I.1b, as a nitrification inhibitor, wherein R$^2$, R$^3$ and R$^4$ are independently of each other selected from H, halogen, OR$^a$, C(=O)OR$^a$, and $C_1$-$C_4$-alkyl;

or R$^3$ and R$^4$ together form a bridge, which forms together with the atoms to which R$^3$ and R$^4$ are bonded an annulated partly or fully unsaturated, or aromatic 5 to 10-membered carbocyclic ring, wherein the carbocyclic ring may be unsubstituted or may carry 1, 2, or 3 identical or different substituents selected from =O, halogen, CN, and OR$^a$, and wherein R$^a$ is H, $C_1$-$C_8$-alkyl, or $C_1$-$C_8$-haloalkyl.

In one particularly preferred embodiment, the present invention relates to the use of a compound of formula I.1a, wherein R$^1$-1a is propargyl, as a nitrification inhibitor, wherein R$^2$, R$^3$ and R$^4$ are independently of each other selected from H, OH, $C_1$-$C_2$-alkyl, $C_1$-$C_2$-alkoxy, OC(=O)$C_1$-$C_2$-alkyl, C(=O)OO$C_1$-$C_2$-alkyl, and C(=O)OOH, or R$^2$ and R$^4$, or R$^3$ and R$^4$ together form a bridge, which forms together with the atoms to which the substituents are bonded an annulated saturated, partly or fully unsaturated, or aromatic 5 to 10-membered monocyclic or bicyclic carbocyclic ring, wherein the carbocyclic ring may be unsubstituted or may carry 1, 2, or 3 identical or different substituents selected from =O, halogen, $C_1$-$C_2$-haloalkyl, $C_1$-$C_2$-alkyl and $C_1$-$C_2$-alkoxy.

Particularly preferred are compounds of formula I.1a, wherein R$^1$-1a is propargyl, and wherein R$^2$, R$^3$ and R$^4$ are independently of each other selected from H, $C_1$-$C_2$-alkyl, and OC(=O)$C_1$-$C_2$-alkyl.

In another particularly preferred embodiment, the present invention relates to the use of a compound of formula I.1b, wherein R$^1$-1b is $C_3$-allenyl, as a nitrification inhibitor, wherein R$^2$, R$^3$ and R$^4$ are independently of each other selected from H, OH, $C_1$-$C_2$-alkyl, $C_1$-$C_2$-alkoxy, OC(=O)$C_1$-$C_2$-alkyl, C(=O)OO$C_1$-$C_2$-alkyl, and C(=O)OOH, or R$^2$ and R$^4$, or R$^3$ and R$^4$ together form a bridge, which forms together with the atoms to which the substituents are bonded an annulated saturated, partly or fully unsaturated, or aromatic 5 to 10-membered monocyclic or bicyclic carbocyclic ring, wherein the carbocyclic ring may be unsubstituted or may carry 1, 2, or 3 identical or different substituents selected from =O, halogen, $C_1$-$C_2$-haloalkyl, $C_1$-$C_2$-alkyl and $C_1$-$C_2$-alkoxy.

Particularly preferred are compounds of formula I.1b, wherein R$^1$-1b is $C_3$-allenyl, and wherein R$^2$, R$^3$ and R$^4$ are independently of each other selected from H, or $C_1$-$C_2$-alkyl.

In particular with a view to their use, preference is given to the compounds of formula I, wherein R$^1$ is a terminal $C_3$-$C_4$-alkynyl group, i.e. compounds of formula I.1a, compiled in table A below.

TABLE A
| No. | Compound of formula I.1a |
|---|---|
| A-1 |  |
| A-2 | 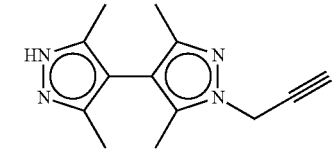 |
| A-3 | 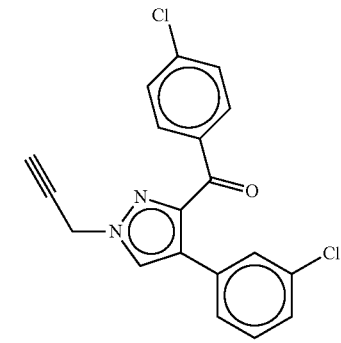 |
| A-4 | 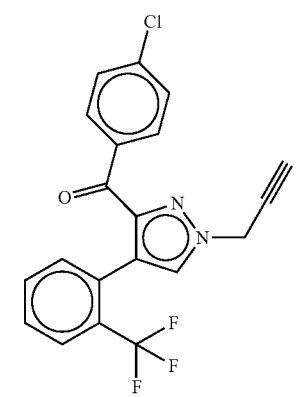 |
| A-5 | 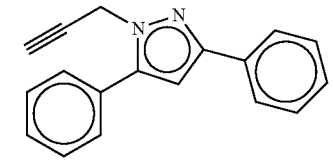 |
| A-6 | 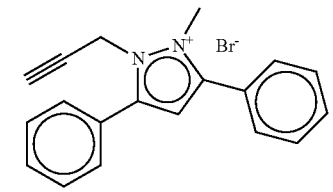 |
| A-7 | 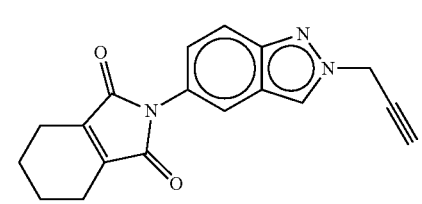 |
| A-8 | |
| A-9 | |
| A-10 | |
| A-11 | |
| A-12 | |
| A-13 | |
| A-14 | |

TABLE A-continued
| No. | Compound of formula I.1a |
|---|---|
| A-15 | 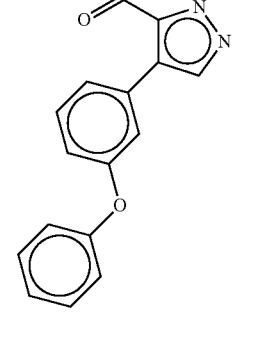 |
| A-16 | |
| A-17 | |
| A-18 | |
| A-19 | |
| A-20 | |
TABLE A-continued
| No. | Compound of formula I.1a |
|---|---|
| A-21 | 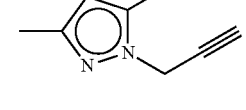 |
| A-22 | |
| A-23 | |
| A-24 | |
| A-25 | |
| A-26 | |

TABLE A-continued

| No. | Compound of formula I.1a |
|---|---|
| A-27 | |
| A-28 | |
| A-29 | |
| A-30 | |
| A-31 | |
| A-32 | |
| A-33 | |
| A-34 | |
| A-35 | |
| A-36 | |
| A-37 | |
| A-38 | |

TABLE A-continued

| No. | Compound of formula I.1a |
|---|---|
| A-39 | |
| A-40 | |
| A-41 | |
| A-42 | |
| A-43 | |
| A-44 | |

TABLE B

| No. | Compound of formula I.1b |
|---|---|
| B-1 | |
| B-2 | |
| B-3 | |
| B-4 | |
| B-5 | |
| B-6 | |

In particular with a view to their use, preference is given to the compounds of formula I, wherein $R^1$ is a terminal $C_3$-$C_4$-allenyl group, in particular a $C_3$-allenyl group, i.e. compounds of formula I.1b, compiled in table B below.

TABLE B-continued

| No. | Compound of formula I.1b |
|---|---|
| B-7 | |
| B-8 | |
| B-9 | |
| B-10 | |
| B-11 | |

In a central aspect the present invention thus relates to the use of a compound of formula I as defined herein as a nitrification inhibitor, or to the use of a composition comprising said compound of formula I as defined herein for reducing nitrification. The compound of formula I or derivatives or salts thereof as defined herein, in particular the compounds of formula I and/or salts or suitable derivatives thereof, as well as compositions comprising said compound of formula I, or agrochemical mixtures comprising said compound of formula I may be used for reducing nitrification.

In a central aspect the present invention thus relates to the use of a compound of formula I as defined herein, in particular any one of the compounds listed in Table A or B above, for reducing nitrification, or to the use of a composition comprising any one of the compounds listed in Table 1 and a carrier for reducing nitrification. Furthermore, the present invention releates to an agricultural mixture comprising any one of the compounds listed in Table A or B above and at least one fertilizer as defined herein. The compounds of formula I or derivatives or salts thereof as defined herein, in particular compounds of formula I and/or salts thereof, as well as compositions comprising said compound of formula I, or agrochemical mixtures comprising said compound of formula I may be used for reducing nitrification.

In one embodiment of the above mentioned aspects of the invention, the compound of formula I is a compound selected from A-14, A-19, A-33, A-42 and A-44.

In one embodiment of the above mentioned aspects of the invention, in particular of the use according to the invention, the compound of formula I is the compound A-14 as defined in table A.

In one embodiment of the above mentioned aspects of the invention, in particular of the use according to the invention, the compound of formula I is the compound A-19 as defined in table A.

In one embodiment of the above mentioned aspects of the invention, in particular of the use according to the invention, the compound of formula I is the compound A-33 as defined in table A.

In one embodiment of the above mentioned aspects of the invention, in particular of the use according to the invention, the compound of formula I is the compound A-42 as defined in table A.

In one embodiment of the above mentioned aspects of the invention, in particular of the use according to the invention, the compound of formula I is the compound A-44 as defined in table A.

In another embodiment of the above mentioned aspects of the invention, the compound of formula I is a compound selected from B-5 and B-6.

In one embodiment of the above mentioned aspects of the invention, in particular of the use according to the invention, the compound of formula I is the compound B-5 as defined in table B.

In one embodiment of the above mentioned aspects of the invention, in particular of the use according to the invention, the compound of formula I is the compound B-6 as defined in table B.

The use may be based on the application of the nitrification inhibitor, the composition or the agrochemical mixture as defined herein to a plant growing on soil and/or the locus where the plant is growing or is intended to grow, or the use may be based on the application of the nitrification inhibitor, the composition or the agrochemical mixture as defined herein to soil where a plant is growing or is intended to grow or to soil substituents. In specific embodiments, the nitrification inhibitor may be used for reducing nitrification in the absence of plants, e.g. as preparatory activity for subsequent agricultural activity, or for reducing nitrification in other technical areas, which are not related to agriculture, e.g. for environmental, water protection, energy production or similar purposes. In specific embodiments, the nitrification inhibitor, or a composition comprising said nitrification inhibitor according to the present invention may be used for the reduction of nitrification in sewage, slurry, manure or dung of animals, e.g. swine or bovine feces. For example, the nitrification inhibitor, or a composition comprising said nitrification inhibitor according to the present invention may be used for the reduction of nitrification in sewage plants, biogas plants, cowsheds, liquid manure tanks or containers etc. Furthermore, the nitrification inhibitor, or a composition comprising said nitrification inhibitor may be used in exhaust air systems, preferably in exhaust air systems of stables or cowsheds. The present invention therefore also relates to the use of compounds of formula I for treating exhaust air, preferably the exhaust air of stables and cowsheds. In further embodiments, the nitrification inhibitor, or a composition comprising said nitrification inhibitor according to the present invention may be used for the reduction of nitrification in situ in animals, e.g. in productive livestock. Accordingly, the nitrification inhibitor, or a composition comprising said nitrification inhibitor according to the present invention may be fed to an animal, e.g. a mammal, for instance together with suitable feed and thereby lead to a reduction of nitrification in the gastrointestinal tract of the animals, which in turn is resulting in reduction of emissions from the gastrointestinal tract. This activity, i.e. the feeding of nitrification inhibitor, or a composition comprising said nitrification inhibitor according to the present invention may be repeated one to several times, e.g. each $2^{nd}$, $3^{rd}$, $4^{th}$, $5^{th}$, $6^{th}$, $7^{th}$ day, or each week, 2 weeks, 3 weeks, or month, 2 months etc.

The use may further include the application of a nitrification inhibitor or derivatives or salts thereof as defined herein above, in particular compounds of formula I and/or salts or suitable derivatives thereof, as well as compositions comprising said nitrification inhibitor, or agrochemical mixtures comprising said nitrification inhibitor as defined herein above to environments, areas or zones, where nitrification takes place or is assumed or expected to take place. Such environments, areas or zones may not comprise plants or soil. For example, the inhibitors may be used for nitrification inhibition in laboratory environments, e.g. based on enzymatic reactions or the like. Also envisaged is the use in green houses or similar indoor facilities.

The term "reducing nitrification" or "reduction of nitrification" as used herein refers to a slowing down or stopping of nitrification processes, e.g. by retarding or eliminating the natural transformation of ammonium into nitrate. Such reduction may be a complete or partial elimination of nitrification at the plant or locus where the inhibitor or composition comprising said inhibitor is applied. For example, a partial elimination may result in a residual nitrification on or in the plant, or in or on the soil or soil substituents where a plant grows or is intended to grow of about 90% to 1%, e.g. 90%, 85%, 80%, 70%, 60%, 50%, 40%, 30%, 20%, 10% or less than 10%, e.g. 5% or less than 5% in comparison to a control situation where the nitrification inhibitor is not used. In certain embodiments, a partial elimination may result in a residual nitrification on or in the plant or in or on the soil or soil substituents where a plant grows or is intended to grow of below 1%, e.g. at 0.5%, 0.1% or less in comparison to a control situation where the nitrification inhibitor is not used.

The use of a nitrification inhibitor as defined herein above, or of a composition as defined herein for reducing nitrification may be a single use, or it may be a repeated use. As single use, the nitrification inhibitor or corresponding compositions may be provided to their target sites, e.g. soil or loci, or objects, e.g. plants, only once in a physiologically relevant time interval, e.g. once a year, or once every 2 to 5 years, or once during the lifetime of a plant.

In other embodiments, the use may be repeated at least once per time period, e.g. the nitrification inhibitor as defined herein above, or a composition as defined herein may be used for reducing nitrification at their target sites or objects two times within a time interval of days, weeks or months. The term "at least once" as used in the context of a use of the nitrification inhibitor means that the inhibitor may be used two times, or several times, i.e. that a repetition or multiple repetitions of an application or treatment with a nitrification inhibitor may be envisaged. Such a repetition may be a 2 times, 3 times, 4 times, 5 times, 6 times, 7 times, 8 times, 9 times, 10 times or more frequent repetition of the use.

The nitrification inhibitor according to the present invention may be used in any suitable form. For example, it may be used as coated or uncoated granule, in liquid or semi-liquid form, as sprayable entity, or in irrigation approaches etc. In specific embodiments, the nitrification inhibitor as defined herein may be applied or used as such, i.e. without formulations, fertilizer, additional water, coatings, or any further ingredient.

The term "irrigation" as used herein refers to the watering of plants or loci or soils or soil substituents where a plant grows or is intended to grow, wherein said watering includes the provision of the nitrification inhibitor according to the present invention together with water.

In a further aspect the invention relates to a composition for reducing nitrification comprising at least one nitrification inhibitor wherein said nitrification inhibitor is a compound of formula I or a derivative as defined herein above; and at least one carrier.

The term "composition for reducing nitrification" as used herein refers to a composition which is suitable, e.g. comprises effective concentrations and amounts of ingredients such as nitrification inhibitors, in particular compounds of formula I or derivatives as defined herein, for reducing nitrification in any context or environment in which nitrification may occur. In one embodiment, the nitrification may be reduced in or on or at the locus of a plant. Typically, the nitrification may be reduced in the root zone of a plant. However, the area in which such reduction of nitrification may occur is not limited to the plants and their environment, but may also include any other habitat of nitrifying bacteria or any site at which nitrifying enzymatic activities can be found or can function in a general manner, e.g. sewage plants, biogas plants, animal effluents from productive livestock, e.g. cows, pigs etc. "Effective amounts" or "effective concentrations" of nitrification inhibitors as defined herein may be determined according to suitable in vitro and in vivo testings known to the skilled person. These amounts and concentrations may be adjusted to the locus, plant, soil, climate conditions or any other suitable parameter which may have an influence on nitrification processes.

A "carrier" as used herein is a substance or composition which facilitates the delivery and/or release of the ingredients to the place or locus of destination. The term includes, for instance, agrochemical carriers which facilitate the delivery and/or release of agrochemicals in their field of use, in particular on or into plants.

Examples of suitable carriers include solid carriers such as phytogels, or hydrogels, or mineral earths e.g. silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g. an solid or liquid ammonium-containing inorganic fertilizer such as an NPK fertilizer, ammonium nitrate, calcium ammonium nitrate, ammonium sulfate nitrate, ammonium sulfate or ammonium phosphate; an solid or liquid organic fertilizer such as liquid manure, semi-liquid manure, stable manure, biogas manure and straw manure, worm castings, compost, seaweed or guano, or an urea-containing fertilizer such as urea, formaldehyde urea, anhydrous ammonium, urea ammonium nitrate (UAN) solution, urea sulphur, stabilized urea, urea based NPK-fertilizers, or urea ammonium sulfate, and products of vegetable origin, such as cereal meal, tree bark meal, wood meal and nutshell meal, cellulose powders and other solid carriers. Further suitable examples of carriers include fumed silica or precipitated silica, which may, for instance, be used in solid formulations as flow aid, anti-caking aid, milling aid and as carrier for liquid active ingredients. Additional examples of suitable carriers are microparticles, for instance microparticles which stick to plant leaves and release their content over a certain period of time. In specific embodiments, agrochemical carriers such as composite gel microparticles that can be used to deliver plant-protection active principles, e.g. as described in U.S. Pat. No. 6,180,141; or compositions comprising at least one phytoactive compound and an encapsulating adjuvant, wherein the adjuvant comprises a fungal cell or a fragment thereof, e.g. as described in WO 2005/102045; or carrier granules, coated with a lipophilic tackifier on the surface, wherein the carrier granule adheres to the surface of plants, grasses and weeds, e.g. as disclosed in US 2007/0280981 may be used. In further specific embodiments, such carriers may include specific, strongly binding molecule which assure that the carrier sticks to the plant, the seed, and/or loci where the plant is growing or is intended to grow, till its content is completely delivered. For instance, the carrier may be or comprise cellulose binding domains (CBDs) have been described as useful agents for attachment of molecular species to cellulose (see U.S. Pat. No. 6,124,117); or direct fusions between a CBD and an enzyme; or a multifunctional fusion protein which may be used for delivery of encapsulated agents, wherein the multifunctional fusion proteins may consist of a first binding domain which is a carbohydrate binding domain and a second binding domain, wherein either the first binding domain or the second binding domain can bind to a microparticle (see also WO 03/031477). Further suitable examples of carriers include bifunctional fusion proteins consisting of a CBD and an anti-RR6 antibody fragment binding to a microparticle, which complex may be deposited onto treads or cut grass (see also WO 03/031477). In another specific embodiment the carrier may be active ingredient carrier granules that adhere to e.g. the surface of plants, grasses, weeds, seeds, and/or loci where the plant is growing or is intended to grow etc. using a moisture-active coating, for instance including gum arabic, guar gum, gum karaya, gum tragacanth and locust bean gum. Upon application of the inventive granule onto a plant surface, water from precipitation, irrigation, dew, coapplication with the granules from special application equipment, or guttation water from the plant itself may provide sufficient moisture for adherence of the granule to the plant surface (see also US 2007/0280981).

In another specific embodiment the carrier, e.g. an agrochemical carrier, may be or comprise polyaminoacids. Polyaminoacids may be obtained according to any suitable process, e.g. by polymerization of single or multiple amino acids such as glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine, histidine and/or ornithine. Polyaminoacids may be combined with a nitrification inhibitor according to the present invention and, in certain embodiments, also with further carriers as mentioned herein above, or other nitrification inhibitors as mentioned herein in any suitable ratio. For example, Polyaminoacids may be combined with a nitrification inhibitor according to the present invention in a ratio of 1 to 10 (polyaminoacids) vs. 0.5 to 2 (nitrification inhibitor according to the present invention).

The composition for reducing nitrification comprising at least one nitrification inhibitor as defined herein may further comprise additional ingredients, for example at least one pesticidal compound. For example, the composition may additionally comprise at least one herbicidal compound and/or at least one fungicidal compound and/or at least one insecticidal compound and/or at least one nematicide.

In further embodiments, the composition may, in addition to the above indicated ingredients, in particular in addition to the nitrification inhibitor of the compound of formula I, further comprise one or more alternative or additional nitrification inhibitors. Examples of envisaged alternative or additional nitrification inhibitors are linoleic acid, alpha-linolenic acid, methyl p-coumarate, methyl ferulate, methyl 3-(4-hydroxyphenyl) propionate (MHPP), Karanjin, brachialacton, p-benzoquinone sorgoleone, 2-chloro-6-(trichloromethyl)-pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (MBT), 5-ethoxy-3-trichloromethyl-1,2,4-thiodiazole (terrazole, etridiazole), 2-sulfanilamidothiazole (ST), ammoniumthiosulfate (ATU), 3-methylpyrazol (3-MP), 3,5-dimethylpyrazole (DMP), 1,2,4-triazol thiourea (TU), N-(1H-pyrazolylmethyl)acetamides such as N-((3(5)-methyl-1H-pyrazole-1-yl)methyl)acetamide, and N-(1H-pyrazolylmethyl) formamides such as N-((3(5)-methyl-1H-pyrazole-1-yl) methyl formamide, N-(4-chloro-3(5)-methyl-pyrazole-1-ylmethyl)-formamide, N-(3(5),4-dimethyl-pyrazole-1-ylmethyl)-formamide, neem, products based on ingredients of neem, cyan amide, melamine, zeolite powder, catechol, benzoquinone, sodium terta board, zinc sulfate.

In a preferred embodiment, the composition according to the present invention may comprise a combination of the nitrification inhibitor of the compound of formula I and 2-chloro-6-(trichloromethyl)-pyridine (nitrapyrin or N-serve).

In a further preferred embodiment, the composition according to the present invention may comprise a combination of the nitrification inhibitor of the compound of formula I and 5-ethoxy-3-trichloromethyl-1,2,4-thiodiazole (terrazole, etridiazole).

In a further preferred embodiment, the composition according to the present invention may comprise a combination of the nitrification inhibitor of the compound of formula I and dicyandiamide (DCD, DIDIN).

In a further preferred embodiment, the composition according to the present invention may comprise a combination of the nitrification inhibitor of the compound of formula I and 3,4-dimethyl pyrazole phosphate (DMPP, ENTEC).

In a further preferred embodiment, the composition according to the present invention may comprise a combination of the nitrification inhibitor of the compound of formula I and 2-amino-4-chloro-6-methylpyrimidine (AM).

In a further preferred embodiment, the composition according to the present invention may comprise a combination of the nitrification inhibitor of the compound of formula I and 2-mercapto-benzothiazole (MBT).

In a further preferred embodiment, the composition according to the present invention may comprise a combination of the nitrification inhibitor of the compound of formula I and 2-sulfanilamidothiazole (ST).

In a further preferred embodiment, the composition according to the present invention may comprise a combination of the nitrification inhibitor of the compound of formula I and ammoniumthiosulfate (ATU).

In a further preferred embodiment, the composition according to the present invention may comprise a combination of the nitrification inhibitor of the compound of formula I and 3-methylpyrazol (3-MP).

In a further preferred embodiment, the composition according to the present invention may comprise a combination of the nitrification inhibitor of the compound of formula I and 3,5-dimethylpyrazole (DMP).

In a further preferred embodiment, the composition according to the present invention may comprise a combination of the nitrification inhibitor of the compound of formula I and 1,2,4-triazol.

In a further preferred embodiment, the composition according to the present invention may comprise a combination of the nitrification inhibitor of the compound of formula I and thiourea (TU).

In yet another preferred embodiment, the composition according to the present invention may comprise a combination of the nitrification inhibitor of the compound of formula I and linoleic acid.

In yet another preferred embodiment, the composition according to the present invention may comprise a combination of the nitrification inhibitor of the compound of formula I and alpha-linolenic acid.

In yet another preferred embodiment, the composition according to the present invention may comprise a combination of the nitrification inhibitor of the compound of formula I and methyl p-coumarate.

In yet another preferred embodiment, the composition according to the present invention may comprise a combination of the nitrification inhibitor of the compound of formula I and methyl 3-(4-hydroxyphenyl) propionate (MHPP).

In yet another preferred embodiment, the composition according to the present invention may comprise a combination of the nitrification inhibitor of the compound of formula I and methyl ferulate.

In yet another preferred embodiment, the composition according to the present invention may comprise a combination of the nitrification inhibitor of the compound of formula I and Karanjin.

In yet another preferred embodiment, the composition according to the present invention may comprise a combination of the nitrification inhibitor of the compound of formula I and brachialacton.

In yet another preferred embodiment, the composition according to the present invention may comprise a combination of the nitrification inhibitor of the compound of formula I and p-benzoquinone sorgoleone.

In yet another preferred embodiment, the composition according to the present invention may comprise a combination of the nitrification inhibitor of the compound of formula I and 4-amino-1,2,4-triazole hydrochloride (ATC).

In yet another preferred embodiment, the composition according to the present invention may comprise a combination of the nitrification inhibitor of the compound of formula I and 1-amido-2-thiourea (ASU).

In yet another preferred embodiment, the composition according to the present invention may comprise a combination of the nitrification inhibitor of the compound of formula I and N-((3(5)-methyl-1H-pyrazole-1-yl)methyl)acetamide.

In yet another preferred embodiment, the composition according to the present invention may comprise a combination of the nitrification inhibitor of the compound of formula I and N-((3(5)-methyl-1H-pyrazole-1-yl)methyl formamide.

In yet another preferred embodiment, the composition according to the present invention may comprise a combination of the nitrification inhibitor of the compound of formula I and N-(4-chloro-3(5)-methyl-pyrazole-1-ylmethyl)-formamide.

In yet another preferred embodiment, the composition according to the present invention may comprise a combination of the nitrification inhibitor of the compound of formula I and N-(3(5),4-dimethyl-pyrazole-1-ylmethyl)-formamide.

In yet another preferred embodiment, the composition according to the present invention may comprise a combination of the nitrification inhibitor of the compound of formula I and neem or products based on ingredients of neem.

In yet another preferred embodiment, the composition according to the present invention may comprise a combination of the nitrification inhibitor of the compound of formula I and cyanamide.

In yet another preferred embodiment, the composition according to the present invention may comprise a combination of the nitrification inhibitor of the compound of formula I and melamine.

In yet another preferred embodiment, the composition according to the present invention may comprise a combination of the nitrification inhibitor of the compound of formula I and zeolite powder.

In yet another preferred embodiment, the composition according to the present invention may comprise a combination of the nitrification inhibitor of the compound of formula I and batechol.

In yet another preferred embodiment, the composition according to the present invention may comprise a combination of the nitrification inhibitor of the compound of formula I and benzoquinone.

In yet another preferred embodiment, the composition according to the present invention may comprise a combination of the nitrification inhibitor of the compound of formula I and sodium terat borate.

In yet another preferred embodiment, the composition according to the present invention may comprise a combination of the nitrification inhibitor of the compound of formula I and zinc sulfate.

In further embodiments, the composition according to the present invention may comprise a combination of the nitrification inhibitor of the compound of formula I and two entities selected from the group comprising: linoleic acid, alpha-linolenic acid, methyl p-coumarate, methyl ferulate, methyl 3-(4-hydroxyphenyl) propionate (MHPP), Karanjin, brachialacton, p-benzoquinone sorgoleone, 2-chloro-6-(trichloromethyl)-pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (MBT), 5-ethoxy-3-trichloromethyl-1,2,4-thiodiazole (terrazole, etridiazole), 2-sulfanilamidothiazole (ST), ammoniumthiosulfate (ATU), 3-methylpyrazol (3-MP), 3,5-dimethylpyrazole (DMP), 1,2,4-triazol and thiourea (TU), N-(1H-pyrazolyl-methyl)acetamides such as N-((3(5)-methyl-1H-pyrazole-1-yl)methyl)acetamide, and N-(1H-pyrazolylmethyl)formamides such as N-((3(5)-methyl-1H-pyrazole-1-yl)methyl formamide, N-(4-chloro-3(5)-methyl-pyrazole-1-ylmethyl)-formamide, or N-(3(5),4-dimethyl-pyrazole-1-ylmethyl)-formamide neem, products based on ingredients of neem, cyan amide, melamine, zeolite powder, catechol, benzoquinone, sodium terta board, zinc sulfate.

In yet another group of embodiments, the composition according to the present invention may comprise a combination of the nitrification inhibitor of the compound of formula I and three, four or more entities selected from the group comprising: linoleic acid, alpha-linolenic acid, methyl p-coumarate, methyl ferulate, methyl 3-(4-hydroxyphenyl) propionate (MHPP), Karanjin, brachialacton, p-benzoquinone sorgoleone, 2-chloro-6-(trichloromethyl)-pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (MBT), 5-ethoxy-3-trichloromethyl-1,2,4-thiodiazole (terrazole, etridiazole), 2-sulfanilamidothiazole (ST) ammoniumthiosulfate (ATU), 3-methylpyrazol (3-MP), 3,5-dimethylpyrazole (DMP), 1,2,4-triazol and thiourea (TU), N-(1H-pyrazolyl-methyl) acetamides such as N-((3(5)-methyl-1H-pyrazole-1-yl) methyl)acetamide, and N-(1H-pyrazolyl-methyl) formamides such as N-((3(5)-methyl-1H-pyrazole-1-yl) methyl formamide, N-(4-chloro-3(5)-methyl-pyrazole-1-ylmethyl)-formamide, or N-(3(5),4-dimethyl-pyrazole-1-ylmethyl)-formamide neem, products based on ingredients of neem, cyan amide, melamine, zeolite powder, catechol, benzoquinone, sodium terta board, zinc sulfate.

In further embodiments, the composition may, in addition to the above indicated ingredients, in particular in addition to the nitrification inhibitor of the compound of formula I, further comprise one or more urease inhibitors. Examples of envisaged urease inhibitors include N-(n-butyl) thiophosphoric acid triamide (NBPT, Agrotain), N-(n-propyl) thiophosphoric acid triamide (NPPT), 2-nitrophenyl phosphoric triamide (2-NPT), further NXPTs known to the skilled person, phenylphosphorodiamidate (PPD/PPDA), hydroquinone, ammonium thiosulfate, and mixtures of NBPT and NPPT (see e.g. U.S. Pat. No. 8,075,659). Such mixtures of NBPT and NPPT may comprise NBPT in amounts of from 40 to 95% wt.-% and preferably of 60 to 80% wt.-% based on the total amount of active substances. Such mixtures are marketed as LIMUS, which is a composition comprising about 16.9 wt.-% NBPT and about 5.6 wt.-% NPPT and about 77.5 wt.-% of other ingredients including solvents and adjuvants.

In a preferred embodiment, the composition according to the present invention may comprise a combination of the nitrification inhibitor of the compound of formula I and N-(n-butyl) thiophosphoric acid triamide (NBPT, Agrotain).

In a further preferred embodiment, the composition according to the present invention may comprise a combination of the nitrification inhibitor of the compound of formula I and phenylphosphorodiamidate (PPD/PPDA).

In a further preferred embodiment, the composition according to the present invention may comprise a combination of the nitrification inhibitor of the compound of formula I and N-(n-propyl) thiophosphoric acid triamide (NPPT).

In a further preferred embodiment, the composition according to the present invention may comprise a combination of the nitrification inhibitor of the compound of formula I and 2-nitrophenyl phosphoric triamide (2-NPT).

In a further preferred embodiment, the composition according to the present invention may comprise a combination of the nitrification inhibitor of the compound of formula I and hydroquinone.

In a further preferred embodiment, the composition according to the present invention may comprise a combination of the nitrification inhibitor of the compound of formula I and ammonium thiosulfate.

In yet another preferred embodiment, the composition according to the present invention may comprise a combination of the nitrification inhibitor of the compound of formula I and neem.

In yet another preferred embodiment, the composition according to the present invention may comprise a combination of the nitrification inhibitor of the compound of formula I and cyanamide.

In yet another preferred embodiment, the composition according to the present invention may comprise a combination of the nitrification inhibitor of the compound of formula I and melamine.

In a further preferred embodiment, the composition according to the present invention may comprise a combination of the nitrification inhibitor of the compound of formula I and a mixture of NBPT and NPPT such as LIMUS.

In further embodiments, the composition according to the present invention may comprise a combination of the nitrification inhibitor of the compound of formula I and two or more entities selected from the group comprising: N-(n-butyl) thiophosphoric acid triamide (NBPT, Agrotain), N-(n-propyl) thiophosphoric acid triamide (NPPT), 2-nitrophenyl phosphoric triamide (2-NPT), further NXPTs known to the skilled person, phenylphosphorodiamidate (PPD/PPDA), hydroquinone, ammonium thiosulfate, and LIMUS.

In further embodiments, the composition may, in addition to one, more or all of the above indicated ingredients, in particular in addition to the nitrification inhibitor of the compound of formula I, further comprise one or more plant growth regulators. Examples of envisaged plant growth regulators are antiauxins, auxins, cytokinins, defoliants, ethylene modulators, ethylene releasers, gibberellins, growth inhibitors, morphactins, growth retardants, growth stimulators, and further unclassified plant growth regulators.

Suitable examples of antiauxins to be used in a composition according to the present invention are clofibric acid or 2,3,5-tri-iodobenzoic acid.

Suitable examples of auxins to be used in a composition according to the present invention are 4-CPA, 2,4-D, 2,4-DB, 2,4-DEP, dichlorprop, fenoprop, IAA (indole-3-acetic acid), IBA, naphthaleneacetamide, alpha-naphthaleneacetic acid, 1-naphthol, naphthoxyacetic acid, potassium naphthenate, sodium naphthenate or 2,4,5-T.

Suitable examples of cytokinins to be used in a composition according to the present invention are 2iP, 6-Benzylaminopurine (6-BA) (=N-6 Benzyladenine), 2,6-Dimethylpuridine (N-Oxide-2,6-Lultidine), 2,6-Dimethylpyridine, kinetin, or zeatin.

Suitable examples of defoliants to be used in a composition according to the present invention are calcium cyanamide, dimethipin, endothal, merphos, metoxuron, pentachlorophenol, thidiazuron, tribufos, or tributyl phosphorotrithioate.

Suitable examples of ethylene modulators to be used in a composition according to the present invention are aviglycine, 1-methylcyclopropene (1-MCP) Prohexadione (prohexadione calcium), or trinexapac (Trinexapac-ethyl).

Suitable examples of ethylene releasers to be used in a composition according to the present invention are ACC, etacelasil, ethephon, or glyoxime.

Suitable examples of gibberellins to be used in a composition according to the present invention are gibberelline or gibberellic acid.

Suitable examples of growth inhibitors to be used in a composition according to the present invention are abscisic acid, S-abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat (mepiquat chloride, mepiquat pentaborate), piproctanyl, prohydrojasmon, propham, or 2,3,5-tri-iodobenzoic acid.

Suitable examples of morphactins to be used in a composition according to the present invention are chlorfluren, chlorflurenol, dichlorflurenol, or flurenol Suitable examples of growth retardants to be used in a composition according to the present invention are chlormequat (chlormequat chloride), daminozide, flurprimidol, mefluidide, paclobutrazol, tetcyclacis, uniconazole, metconazol.

Suitable examples of growth stimulators to be used in a composition according to the present invention are brassinolide, forchlorfenuron, or hymexazol.

Suitable examples of further unclassified plant growth regulators to be used in a composition according to the present invention are amidochlor, benzofluor, buminafos, carvone, choline chloride, ciobutide, clofencet, cloxyfonac, cyanamide, cyclanilide, cycloheximide, cyprosulfamide, epocholeone, ethychlozate, ethylene, fenridazon, fluprimidol, fluthiacet, heptopargil, holosulf, inabenfide, karetazan, lead arsenate, methasulfocarb, pydanon, sintofen, diflufenzopyr or triapenthenol In a preferred embodiment, the composition according to the present invention may comprise a combination of the nitrification inhibitor of the compound of formula I and at least one compound selected from the group comprising: abscisic acid, amidochlor, ancymidol, 6-benzylaminopurine (=N-6 benzyladenine), brassinolide, butralin, chlormequat (chlormequat chloride), choline chloride, cyclanilide, daminozide, diflufenzopyr, dikegulac, dimethipin, 2,6-dimethylpyridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), 1-methylcyclopropene (1-MCP), naphthaleneacetic acid, N-6 benzyladenine, paclobutrazol, prohexadione (prohexadione calcium), prohydrojasmon, thidiazuron, triapenthenol, tributyl phosphorotrithioate, 2,3,5-tri-iodobenzoic acid, trinexapac-ethyl, and uniconazole.

In a preferred embodiment, the composition according to the present invention may comprise a combination of the nitrification inhibitor of the compound of formula I and clofibric acid.

In a further preferred embodiment, the composition according to the present invention may comprise a combination of the nitrification inhibitor of the compound of formula I and 2,3,5-tri-iodobenzoic acid.

In a further preferred embodiment, the composition according to the present invention may comprise a combination of the nitrification inhibitor of the compound of formula I and 4-CPA.

In a further preferred embodiment, the composition according to the present invention may comprise a combination of the nitrification inhibitor of the compound of formula I and 2,4-D.

In a further preferred embodiment, the composition according to the present invention may comprise a combination of the nitrification inhibitor of the compound of formula I and 2,4-DB.

In a further preferred embodiment, the composition according to the present invention may comprise a combination of the nitrification inhibitor of the compound of formula I and 2,4-DEP.

In a further preferred embodiment, the composition according to the present invention may comprise a combination of the nitrification inhibitor of the compound of formula I and dichlorprop.

In a further preferred embodiment, the composition according to the present invention may comprise a combination of the nitrification inhibitor of the compound of formula I and fenoprop.

In a further preferred embodiment, the composition according to the present invention may comprise a combination of the nitrification inhibitor of the compound of formula I and IAA (indole-3-acetic acid).

In a further preferred embodiment, the composition according to the present invention may comprise a combination of the nitrification inhibitor of the compound of formula I and IBA.

In a further preferred embodiment, the composition according to the present invention may comprise a combination of the nitrification inhibitor of the compound of formula I and naphthaleneacetamide.

In a further preferred embodiment, the composition according to the present invention may comprise a combination of the nitrification inhibitor of the compound of formula I and alpha-naphthaleneacetic acid.

In a further preferred embodiment, the composition according to the present invention may comprise a combination of the nitrification inhibitor of the compound of formula I and 1-naphthol.

In a further preferred embodiment, the composition according to the present invention may comprise a combination of the nitrification inhibitor of the compound of formula I and naphthoxyacetic acid.

In a further preferred embodiment, the composition according to the present invention may comprise a combination of the nitrification inhibitor of the compound of formula I and potassium naphthenate.

In a further preferred embodiment, the composition according to the present invention may comprise a combination of the nitrification inhibitor of the compound of formula I and sodium naphthenate.

In a further preferred embodiment, the composition according to the present invention may comprise a combination of the nitrification inhibitor of the compound of formula I and 2,4,5-T.

In a further preferred embodiment, the composition according to the present invention may comprise a combination of the nitrification inhibitor of the compound of formula I and 2iP.

In a further preferred embodiment, the composition according to the present invention may comprise a combination of the nitrification inhibitor of the compound of formula I and 6-Benzylaminopurine (6-BA) (=N-6 Benzyladenine).

In a further preferred embodiment, the composition according to the present invention may comprise a combination of the nitrification inhibitor of the compound of formula I and 2,6-Dimethylpuridine (N-Oxide-2,6-Lultidine).

In a further preferred embodiment, the composition according to the present invention may comprise a combination of the nitrification inhibitor of the compound of formula I and zeatin.

In a further preferred embodiment, the composition according to the present invention may comprise a combination of the nitrification inhibitor of the compound of formula I and kinetin.

In a further preferred embodiment, the composition according to the present invention may comprise a combination of the nitrification inhibitor of the compound of formula I and calcium cyanamide.

In a further preferred embodiment, the composition according to the present invention may comprise a combination of the nitrification inhibitor of the compound of formula I and dimethipin.

In a further preferred embodiment, the composition according to the present invention may comprise a combination of the nitrification inhibitor of the compound of formula I and endothal.

In a further preferred embodiment, the composition according to the present invention may comprise a combination of the nitrification inhibitor of the compound of formula I and merphos.

In a further preferred embodiment, the composition according to the present invention may comprise a combination of the nitrification inhibitor of the compound of formula I and metoxuron.

In a further preferred embodiment, the composition according to the present invention may comprise a combination of the nitrification inhibitor of the compound of formula I and pentachlorophenol.

In a further preferred embodiment, the composition according to the present invention may comprise a combination of the nitrification inhibitor of the compound of formula I and thidiazuron.

In a further preferred embodiment, the composition according to the present invention may comprise a combination of the nitrification inhibitor of the compound of formula I and tribufos.

In a further preferred embodiment, the composition according to the present invention may comprise a combination of the nitrification inhibitor of the compound of formula I and tributyl phosphorotrithioate.

In a further preferred embodiment, the composition according to the present invention may comprise a combination of the nitrification inhibitor of the compound of formula I and aviglycine.

In a further preferred embodiment, the composition according to the present invention may comprise a combination of the nitrification inhibitor of the compound of formula I and 1-methylcyclopropene.

A composition as defined herein, in particular a composition comprising a nitrification inhibitor as defined herein and a plant growth regulator as defined herein, may be used for the increase of plant health.

The term "plant health" as used herein is intended to mean a condition of the plant which is determined by several aspects alone or in combination with each other. One indicator (indicator 1) for the condition of the plant is the crop yield. "Crop" and "fruit" are to be understood as any plant product which is further utilized after harvesting, e.g. fruits in the proper sense, vegetables, nuts, grains, seeds, wood (e.g. in the case of silviculture plants), flowers (e.g. in the case of gardening plants, ornamentals) etc., that is anything of economic value that is produced by the plant. Another indicator (indicator 2) for the condition of the plant is the plant vigor. The plant vigor becomes manifest in several aspects, too, some of which are visual appearance, e.g. leaf color, fruit color and aspect, amount of dead basal leaves and/or extent of leaf blades, plant weight, plant height, extent of plant verse (lodging), number, strong ness and productivity of tillers, panicles' length, extent of root system, strongness of roots, extent of nodulation, in particular of rhizobial nodulation, point of time of germination, emergence, flowering, grain maturity and/or senescence, protein content, sugar content and the like. Another indicator (indicator 3) for an increase of a plant's health is the reduction of biotic or abiotic stress factors. The three above mentioned indicators for the health condition of a plant may be interdependent and may result from each other. For example, a reduction of biotic or abiotic stress may lead to a better plant vigor, e.g. to better and bigger crops, and thus to an increased yield. Biotic stress, especially over longer terms, can have harmful effects on plants. The term "biotic stress" as used in the context of the present invention refers in particular to stress caused by living organisms. As a result, the quantity and the quality of the stressed plants, their crops and fruits decrease. As far as quality is concerned, reproductive development is usually severely affected with consequences on the crops which are important for fruits or seeds. Growth may be slowed by the stresses; polysaccharide synthesis, both structural and storage, may be reduced or modified: these effects may lead to a decrease in biomass and to changes in the nutritional value of the product. Abiotic stress includes drought, cold, increased UV, increased heat, or other changes in the environment of the plant, that leads to sub-optimal growth conditions. The term "increased yield" of a plant as used herein means that the yield of a product of the respective plant is increased by a measurable amount over the yield of the same product of the plant produced under the same conditions, but without the application of the composition of the invention. According to the present invention, it is preferred that the yield be increased by at least 0,5%, more preferred at least 1%, even more preferred at least 2%, still more preferred at least 4%. An increased yield may, for example, be due to a reduction of nitrification and a corresponding improvement of uptake of nitrogen nutrients. The term "improved plant vigor" as used herein means that certain crop characteristics are increased or improved by a measurable or noticeable amount over the same factor of the plant produced under the same conditions, but without the application of the composition of the present invention. Improved plant vigor can be characterized, among others, by following improved properties of a plant:
  (a) improved vitality of the plant,
  (b) improved quality of the plant and/or of the plant products, e.g.
  (b) enhanced protein content,
  (c) improved visual appearance,
  (d) delay of senescence,
  (e) enhanced root growth and/or more developed root system (e.g. determined by the dry mass of the root),
  (f) enhanced nodulation, in particular rhizobial nodulation, (g) longer panicles,
(h) bigger leaf blade,
(i) less dead basal leaves,
(j) increased chlorophyll content
(k) prolonged photosynthetically active period
(l) improved nitrogen-supply within the plant The improvement of the plant vigor according to the present invention particularly means that the improvement of anyone or several or all of the above mentioned plant characteristics are improved. It further means that if not all of the above characteristics are improved, those which are not improved are not worsened as compared to plants which were not treated according to the invention or are at least not worsened to such an extent that the negative effect exceeds the positive effect of the improved characteristic (i.e. there is always an overall positive effect which preferably results in an improved crop yield). An improved plant vigor may, for example, be due to a reduction of nitrification and, e.g. a regulation of plant growth.

In further embodiments, the composition may, in addition to the above indicated ingredients, in particular in addition to the nitrification inhibitor of the compound of formula I, further comprise one or more pesticides.

A pesticide is an agent that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

According to one embodiment, individual components of the composition according to the invention such as parts of a kit or parts of a binary or ternary mixture may be mixed by the user himself in a spray tank or any other kind of vessel used for applications (e.g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

The following list of pesticides I (e.g. pesticidally-active substances), in conjunction with which the compounds I can be used, is intended to illustrate the possible combinations but does not limit them:

A) Respiration inhibitors

Inhibitors of complex III at $Q_o$ site (e.g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methylallylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A. 1.22), 1-[3-chloro-2-[[1-(4-chlorophenyl)-1H-pyrazol-3-yl]oxymethyl]-phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl]phenyl]-4-methyl-tetrazol-5-one (A.1.29), 1-[3-cyclopropyl-2-[[2-methyl-4-(1-methylpyrazol-3-yl)phenoxy]methyl]phenyl]-4-methyl-tetrazol-5-one (A. 1.30), 1-[3-(difluoromethoxy)-2-[[2-methyl-4-(1-methyl pyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl) phenyl]-ethylideneamino] oxymethyl]phenyl]tetrazol-5-one (A.1.33), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), (Z,2E)-5-[1-(4-chloro-2-fluorophenyl)pyrazol-3-yl] oxy-2-methoxyimino-N,3-dimethyl-pent-3-enamide (A.1.36), inhibitors of complex III at $Q_i$ site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate (A.2.3), [(3S,6S,7R,8R)-8-benzyl-3-[[3-(acetoxymethoxy)-4-methoxy-pyridine-2-carbonyl] amino]-6-methyl-4,9-dioxo-1,5-dioxonan-7-yl]2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7), (3S,6S,7R,8R)-8-benzyl-3-[3-[(isobutyryloxy) methoxy]-4-methoxypicolinamido]-6-methyl-4,9-dioxo-1,5-dioxonan-7-yl isobutyrate (A.2.8);

inhibitors of complex II (e.g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N-(1,1,3-trimethylindan-4-yl)pyrazole-4-carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methylethyl]-3-(difluoromethyl)-1-methyl-pyrazole-4-carboxamide (A.3.27);

other respiration inhibitors (e.g. complex I, uncouplers): diflumetorim (A.4.1), (5,8-difluoroquinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol biosynthesis inhibitors (SBI fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S;3R)-3-(2-chlorophenyl)-2-(2,4-difluorophenyl)-oxiranylmethyl]-5-thiocyanato-1H-[1,2,4]triazolo (B.1.31), 2-[rel-(2S;3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl) phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy) phenyl]-3-methyl-1-(1,2,4-triazol-1-yl)butan-2-ol (B.1.39), 2-[4-(4-chlorophenoxy)-2-(trifluoromethyl) phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenyl)isoxazol-4-yl]-(3-pyridyl)methanol (B.1.50);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic acid synthesis inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of cell division and cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of amino acid and protein synthesis methionine synthesis inhibitors (anilino-pyrimidines): cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal transduction inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and membrane synthesis inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenyl)ethanesulfonyl)-but-2-yl) carbamic acid-(4-fluorophenyl) ester (G.3.8);

compounds affecting cell membrane permeability and fatty acides: propamocarb (G.4.1);

fatty acid amide hydrolase inhibitors: oxathiapiprolin (G.5.1), 2-{3-[2-(1-{[3,5-bis(difluoromethyl-1 H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with Multi Site Action
- inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);
- thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);
- organochlorine compounds (e.g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methylbenzenesulfonamide (H.3.12);
- guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell wall synthesis inhibitors
- inhibitors of glucan synthesis: validamycin (I.1.1), polyoxin B (I.1.2);
- melanin synthesis inhibitors: pyroquilon (I.2.1), tricyclazole (I.2.2), carpropamid (I.2.3), dicyclomet (I.2.4), fenoxanil (I.2.5);

J) Plant defence inducers
- acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown mode of action
- bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquatmethylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothalisopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperid in-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K. 1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclopropylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethylphenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyl-tetrazol-5-yl)-phenylmethylene]amino]oxymethyl]-2-pyridyl]carbamate (K. 1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phenyl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxazepine (K.1.48);

M) Insecticides
- M.1) Acetylcholine esterase (AChE) inhibitors from the class of: M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;
- M.2) GABA-gated chloride channel antagonists such as: M.2A cyclodiene organochlorine compounds, as for example endosulfan or chlordane; or M.2B fiproles (phenylpyrazoles), as for example ethiprole, fipronil, flufiprole, pyrafluprole and pyriprole;
- M.3) Sodium channel modulators from the class of M.3A pyrethroids, for example acrinathrin, allethrin, d-cis-trans allethrin, d-trans allethrin, bifenthrin, bioallethrin, bioallethrin S-cyclopentenyl, bioresmethrin, cyprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4) Nicotinic acetylcholine receptor agonists (nAChR) from the class of M.4A neonicotinoids, for example acetamiprid, clothianidin, cycloxaprid, dinotefuran, imidacloprid, nitenpyram, thiacloprid and thiamethoxam; or the compounds M.4A.2: (2E-)-1-[(6-Chloropyridin-3-yl)methyl]-N'-nitro-2-pentylidenehydrazinecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or from the class M.4B nicotine;

M.5) Nicotinic acetylcholine receptor allosteric activators from the class of spinosyns, for example spinosad or spinetoram;

M.6) Chloride channel activators from the class of avermectins and milbemycins, for example abamectin, emamectin benzoate, ivermectin, lepimectin or milbemectin;

M.7) Juvenile hormone mimics, such as M.7A juvenile hormone analogues as hydroprene, kinoprene and methoprene; or others as M.7B fenoxycarb or M.7C pyriproxyfen;

M.8) miscellaneous non-specific (multi-site) inhibitors, for example M.8A alkyl halides as methyl bromide and other alkyl halides, or M.8B chloropicrin, or M.8C sulfuryl fluoride, or M.8D borax, or M.8E tartar emetic;

M.9) Selective homopteran feeding blockers, for example M.9B pymetrozine, or M.9C flonicamid;

M.10) Mite growth inhibitors, for example M.10A clofentezine, hexythiazox and diflovidazin, or M.10B etoxazole;

M.11) Microbial disruptors of insect midgut membranes, for example *Bacillus thuringiensis* or *Bacillus sphaericus* and the insecticdal proteins they produce such as *Bacillus thuringiensis* subsp. *israelensis, Bacillus sphaericus, Bacillus thuringiensis* subsp. *aizawai, Bacillus thuringiensis* subsp. *kurstaki* and *Bacillus thuringiensis* subsp. *tenebrionis*, or the Bt crop proteins: Cry1Ab, Cry1Ac, Cry1 Fa, Cry2Ab, mCry3A, Cry3Ab, Cry3Bb and Cry34/35Ab1;

M.12) Inhibitors of mitochondrial ATP synthase, for example M.12A diafenthiuron, or M.12B organotin miticides such as azocyclotin, cyhexatin or fenbutatin oxide, or M.12C propargite, or M.12D tetradifon;

M.13) Uncouplers of oxidative phosphorylation via disruption of the proton gradient, for example chlorfenapyr, DNOC or sulfluramid;

M.14) Nicotinic acetylcholine receptor (nAChR) channel blockers, for example nereistoxin analogues as bensultap, cartap hydrochloride, thiocyclam or thiosultap sodium;

M.15) Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16) Inhibitors of the chitin biosynthesis type 1, as for example buprofezin;

M.17) Moulting disruptors, Dipteran, as for example cyromazine;

M.18) Ecdyson receptor agonists such as diacylhydrazines, for example methoxyfenozide, tebufenozide, halofenozide, fufenozide or chromafenozide;

M.19) Octopamin receptor agonists, as for example amitraz;

M.20) Mitochondrial complex III electron transport inhibitors, for example M.20A hydramethylnon, or M.20B acequinocyl, or M.20C fluacrypyrim;

M.21) Mitochondrial complex I electron transport inhibitors, for example M.21A METI acaricides and insecticides such as fenazaquin, fenpyroximate, pyrimidifen, pyridaben, tebufenpyrad or tolfenpyrad, or M.21 B rotenone;

M.22) Voltage-dependent sodium channel blockers, for example M.22A indoxacarb, or M.22B metaflumizone, or M.22B.1: 2-[2-(4-Cyanophenyl)-1-[3-(trifluoromethyl) phenyl]ethylidene]-N-[4-(difluoromethoxy)phenyl]-hydrazinecarboxamide or M.22B.2: N-(3-Chloro-2-methylphenyl)-2-[(4-chlorophenyl)[4-[methyl (methylsulfonyl)amino]phenyl]methylene]-hydrazinecarboxamide;

M.23) Inhibitors of the of acetyl CoA carboxylase, such as Tetronic and Tetramic acid derivatives, for example spirodiclofen, spiromesifen or spirotetramat;

M.24) Mitochondrial complex IV electron transport inhibitors, for example M.24A phosphine such as aluminium phosphide, calcium phosphide, phosphine or zinc phosphide, or M.24B cyanide;

M.25) Mitochondrial complex II electron transport inhibitors, such as beta-ketonitrile derivatives, for example cyenopyrafen or cyflumetofen;

M.28) Ryanodine receptor-modulators from the class of diamides, as for example flubendiamide, chlorantraniliprole (rynaxypyr@), cyantraniliprole (cyazypyr@), tetraniliprole, or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl) phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-di bromo-2-({[3-bromo-1-(3-chlorpyridin-2-yl)-1H-pyrazol-5-yl]carbonyl}-amino)benzoyl]-1,2-dimethylhydrazinecarboxylate; or a compound selected from M.28.5a) to M.28.5d) and M.28.5h) to M.28.5l): M.28.5a) N-[4,6-dichloro-2-[(diethyl-lambda-4-sulfanyl idene)carbamoyl]-phenyl]-2-(3-chloro-2-pyridyl)-5-(trifluoromethyl)pyrazole-3-carboxamide; M.28.5b) N-[4-chloro-2-[(diethyl-lambda-4-sulfanyl idene)carbamoyl]-6-methyl-phenyl]-2-(3-chloro-2-pyridyl)-5-(trifluoromethyl)pyrazole-3-carboxamide; M.28.5c) N-[4-chloro-2-[(di-2-propyl-lambda-4-sulfanyl idene) carbamoyl]-6-methyl-phenyl]-2-(3-chloro-2-pyridyl)-5-(trifluoromethyl)pyrazole-3-carboxamide; M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; M.28.5h) N-[4,6-dibromo-2-[(diethyl-lambda-4-sulfanylidene) carbamoyl]-phenyl]-2-(3-chloro-2-pyridyl)-5-(trifluoromethyl)pyrazole-3-carboxamide; M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3- chloro-2-pyridinyl)-N-[2,4-dichloro-6-[[(1-cyano-1-methylethyl)amino]carbonyl]phenyl]-1 H-pyrazole-5-carboxamide; M.28.5k) 3-Bromo-N-[2,4-dichloro-6-(methylcarbamoyl)phenyl]-1-(3,5-dichloro-2-pyridyl)-1H-pyrazole-5-carboxamide; M.28.5l) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; or a compound selected from M.28.6: N-(2-cyanopropan-2-yl)-N-(2,4-dimethylphenyl)-3-iodobenzene-1,2-dicarboxamide; or M.28.7: 3-Chloro-N-(2-cyanopropan-2-yl)-N-(2,4-dimethylphenyl)-benzene-1,2-dicarboxamide;

M.29) insecticidal active compounds of unknown or uncertain mode of action, as for example afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds;

M.29.3: 11-(4-chloro-2,6-dimethylphenyl)-12-hydroxy-1,4-dioxa-9-azadispiro[4.2.4.2]-tetradec-11-en-10-one, or the compound M.29.4: 3-(4'-fluoro-2,4-dimethylbiphenyl-3-yl)-4-hydroxy-8-oxa-1-azaspiro[4.5]dec-3-en-2-one, or the compound M.29.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *Bacillus firmus* (Votivo, 1-1582);

or a compound selected from the group of M.29.6, wherein the compound is selected from M.29.6a) to M.29.6k): M.29.6a) (E/Z)—N-[1-[(6-chloro-3-pyridyl)methyl]-2-pyridylidene]-2,2,2-trifluoro-acetamide; M.29.6b) (E/Z)—N-[1-[(6-chloro-5-fluoro-3-pyridyl)methyl]-2-pyridylidene]-2,2,2-trifluoro-acetamide; M.29.6c) (E/Z)-2,2,2-trifluoro-N-[1-[(6-fluoro-3-pyridyl)methyl]-2-pyridylidene]acetamide; M.29.6d) (E/Z)—N-[1-[(6-bromo-3-pyridyl)methyl]-2-pyridylidene]-2,2,2-trifluoro-acetamide; M.29.6e) (E/Z)—N-[1-[1-(6-chloro-3-pyridyl)ethyl]-2-pyridylidene]-2,2,2-trifluoro-acetamide; M.29.6f) (E/Z)—N-[1-[(6-chloro-3-pyridyl)methyl]-2-pyridylidene]-2,2-difluoroacetamide; M.29.6g) (E/Z)-2-chloro-N-[1-[(6-chloro-3-pyridyl)methyl]-2-pyridylidene]-2,2-difluoro-acetamide; M.29.6h) (E/Z)—N-[1-[(2-chloropyrimidin-5-yl)methyl]-2-pyridylidene]-2,2,2-trifluoro-acetamide; M.29.6i) (E/Z)—N-[1-[(6-chloro-3-pyridyl)methyl]-2-pyridylidene]-2,2,3,3,3-pentafluoro-propanamide.); M.29.6j) N-[1-[(6-chloro-3-pyridyl)methyl]-2-pyridylidene]-2,2,2-trifluoro-thioacetamide; or M.29.6k) N-[1-[(6-chloro-3-pyridyl)methyl]-2-pyridylidene]-2,2,2-trifluoro-N'-isopropyl-acetamidine; or the compounds M.29.8: 8-chloro-N-[2-chloro-5-methoxyphenyl)sulfonyl]-6-trifluoromethyl-imidazo[1,2-a]pyridine-2-carboxamide;

or the compounds M.29.9.a): 4-[5-(3,5-dichlorophenyl)-5-(trifluoromethyl)-4H-isoxazol-3-yl]-2-methyl-N-(1-oxothietan-3-yl)benzamide; or M.29.9.b): 4-[5-(3,5-Dichlorophenyl)-5-trifluoromethyl-4,5-dihydroisoxazol-3-yl]-N-[(methoxyimino)methyl]-2-methylbenzamide;

or M.29.10: 5-[3-[2,6-dichloro-4-(3,3-dichloroallyloxy)phenoxy]propoxy]-1H-pyrazole; or a compound selected from the group of M.29.11, wherein the compound is selected from M.29.11 b) to M.29.11 p): M.29.11.b) 3-(benzoylmethylamino)-N-[2-bromo-4-[1,2,2,3,3,3-hexafluoro-1-(trifluoromethyl)propyl]-6-(trifluoromethyl) phenyl]-2-fluorobenzamide; M.29.11.c) 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide; M.29.11.d) N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.e) N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide; M.29.11.f) 4-fluoro-N-[2-fluoro-3-[[[2-iodo-4-[1,2,2,2-tetrafluoro-1-(trifluoromethyl)-ethyl]-6-(trifluoromethyl)phenyl]amino]carbonyl]phenyl]-N-methyl-benzamide; M.29.11.g) 3-fluoro-N-[2-fluoro-3-[[[2-iodo-4-[1,2,2,2-tetrafluoro-1-(trifluoromethyl)-ethyl]-6-(trifluoromethyl)phenyl]amino]carbonyl]phenyl]-N-methyl-benzamide; M.29.11.h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide; M.29.11.i) 4-cyano-N-[2-cyano-5-[[2,6-dibromo-4-[1,2,2,3,3,3-hexafluoro-1-(trifluoromethyl)-propyl]phenyl]carbamoyl]phenyl]-2-methyl-benzamide; M.29.11.j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide; M.29.11.k) N-[5-[[2-chloro-6-cyano-4-[1,2,2,3,3,3-hexafluoro-1-(trifluoromethyl)propyl]phenyl]carbamoyl]-2-cyanophenyl]-4-cyano-2-methyl-benzamide; M.29.11.l) N-[5-[[2-bromo-6-chloro-4-[2,2,2-trifluoro-1-hydroxy-1-(trifluoromethyl)ethyl]phenyl]carbamoyl]-2-cyanophenyl]-4-cyano-2-methyl-benzamide; M.29.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; M.29.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide; M.29.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide; M.29.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide;

or a compound selected from the group of M.29.12, wherein the compound is selected from M.29.12a) to M.29.12m): M.29.12.a) 2-(1,3-Dioxan-2-yl)-6-[2-(3-pyridinyl)-5-thiazolyl]-pyridine; M.29.12.b) 2-[6-[2-(5-Fluoro-3-pyridinyl)-5-thiazolyl]-2-pyridinyl]-pyrimidine; M.29.12.c) 2-[6-[2-(3-Pyridinyl)-5-thiazolyl]-2-pyridinyl]-pyrimidine; M.29.12.d) N-Methylsulfonyl-6-[2-(3-pyridyl)thiazol-5-yl]pyridine-2-carboxamide; M.29.12.e) N-Methylsulfonyl-6-[2-(3-pyridyl)thiazol-5-yl]pyridine-2-carboxamide; M.29.12.f) N-Ethyl-N-[4-methyl-2-(3-pyridyl)thiazol-5-yl]-3-methylthio-propanamide; M.29.12.g) N-Methyl-N-[4-methyl-2-(3-pyridyl)thiazol-5-yl]-3-methylthio-propanamide; M.29.12.h) N,2-Dimethyl- N-[4-methyl-2-(3-pyridyl)thiazol-5-yl]-3-methylthio-propanamide; M.29.12.i) N-Ethyl-2-methyl-N-[4-methyl-2-(3-pyridyl)thiazol-5-yl]-3-methylthio-propanamide; M.29.12.j) N-[4-Chloro-2-(3-pyridyl)thiazol-5-yl]-N-ethyl-2-methyl-3-methylthio-propanamide; M.29.12.k) N-[4-Chloro-2-(3-pyridyl)thiazol-5-yl]-N,2-dimethyl-3-methylthio-propanamide; M.29.12.l) N-[4-Chloro-2-(3-pyridyl)thiazol-5-yl]-N-methyl-3-methylthio-propanamide; M.29.12.m) N-[4-Chloro-2-(3-pyridyl)thiazol-5-yl]-N-ethyl-3-methylthio-propanamide;

or the compounds M.29.14a) 1-[(6-Chloro-3-pyridinyl)methyl]-1,2,3,5,6,7-hexahydro-5-methoxy-7-methyl-8-nitro-imidazo[1,2-a]pyridine; or M.29.14b) 1-[(6-Chloropyridin-3-yl)methyl]-7-methyl-8-nitro-1,2,3,5,6,7-hexahydroimidazo[1,2-a]pyridin-5-ol; or the compounds M.29.16a) 1-isopropyl-N,5-dimethyl-N-pyridazin-4-yl-pyrazole-4-carboxamide; or M.29.16b) 1-(1,2-dimethylpropyl)-N-ethyl-5-methyl-N-pyridazin-4-yl-pyrazole-4-carboxamide; M.29.16c) N,5-dimethyl-N-pyridazin-4-yl-1-(2,2,2-trifluoro-1-methyl-ethyl)pyrazole-4-carboxamide; M.29.16d) 1-[1-(1-cyanocyclopropyl)ethyl]-N-ethyl-5-methyl-N-pyridazin-4-yl-pyrazole-4-carboxamide; M.29.16e) N-ethyl-1-(2-fluoro-1-methyl-propyl)-5-methyl-N-pyridazin-4-yl-pyrazole-4-carboxamide; M.29.16f) 1-(1,2-dimethylpropyl)-N,5-dimethyl-N-pyridazin-4-yl-pyrazole-4-carboxamide; M.29.16g) 1-[1-(1-cyano-cyclopropyl)ethyl]-N,5-dimethyl-N-pyridazin-4-yl-pyrazole-4-carboxamide; M.29.16h) N-methyl-1-(2-fluoro-1-methyl-propyl]-5-methyl-N-pyridazin-4-yl-pyrazole-4-carboxamide; M.29.16i) 1-(4,4-difluorocyclohexyl)-N-ethyl-5-methyl-N-pyridazin-4-yl-pyrazole-4-carboxamide; or M.29.16j) 1-(4,4-difluorocyclohexyl)-N,5-dimethyl-N-pyridazin-4-yl-pyrazole-4-carboxamide;

N) Herbicides herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, or ureas.

The present invention furthermore relates to agrochemical compositions comprising a mixture of at least one compound of formula I, i.e. a nitrification inhibitor of the present invention (compound I or component I) and at least one further active substance useful for plant protection, e.g. selected from the groups A) to N) (component 2), in particular one further herbicide selected from the group N).

By applying compounds I together with at least one active substance from groups A) to N) a synergistic plant health effect can be obtained, i.e. more then simple addition of the individual effects is obtained (synergistic mixtures).

This can be obtained by applying the compounds I and at least one further active substance simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide I sequentially the time between both applications may vary e.g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In case of a mixture comprising a pesticide II selected from group L), it is preferred that the pesticide I is applied as last treatment.

In the binary mixtures and compositions according to the invention the weight ratio of the component 1) and the component 2) generally depends from the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to further embodiments of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

According to further embodiments of the mixtures and compositions, the weight ratio of the component 1) and the component 2) generally depends from the properties of the active components used, usually it is in the range of from 1:10,000 to 10,000:1, regularly in the range of from 1:100 to 10,000:1, preferably in the range of from 1:100 to 5,000:1, more preferably in the range of from 1:1 to 1,000:1, even more preferably in the range of from 1:1 to 500:1 and in particular in the range of from 10:1 to 300:1.

According to further embodiments of the mixtures and compositions, the weight ratio of the component 1) and the component 2) usually is in the range of from 20,000:1 to 1:10, often in the range of from 10,000:1 to 1:1, regularly in the range of from 5,000:1 to 5:1, preferably in the range of from 5,000:1 to 10:1, more preferably in the range of from 2,000:1 to 30:1, even more preferably in the range of from 2,000:1 to 100:1 and in particular in the range of from 1,000:1 to 100:1.

According to further embodiments of the mixtures and compositions, the weight ratio of the component 1) and the component 2) usually is in the range of from 1:20,000 to 10:1, often in the range of from 1:10,000 to 1:1, regularly in the range of from 1:5,000 to 1:5, preferably in the range of from 1:5,000 to 1:10, more preferably in the range of from 1:2,000 to 1:30, even more preferably in the range of from 1:2,000 to 1:100 and in particular in the range of from 1:1,000 to 1:100.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

The active substances listed under groups A) to K), their preparation and their activity e.g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296, 272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

The commercially available compounds of the group M listed above may be found in The Pesticide Manual, 16th Edition, C. MacBean, British Crop Protection Council (2013) among other publications. The online Pesticide Manual is updated regularly and is accessible through http://bcpcdata.com/pesticide-manual.html. Another online data base for pesticides providing the ISO common names is http://www.alanwood.net/pesticides. The M.4 neonicotinoid cycloxaprid is known from WO2010/069266 and WO2011/069456, the neonicotinoid M.4A.2, sometimes also to be named as guadipyr, is known from WO2013/003977, and the neonicotinoid M.4A.3 (approved as paichongding in China) is known from WO2007/101369. The metaflumizone analogue M.22B.1 is described in CN10171577 and the analogue M.22B.2 in CN102126994. The phthalamides M.28.1 and M.28.2 are both known from WO2007/101540. The anthranilamide M.28.3 is described in WO2005/077934. The hydrazide compound M.28.4 is described in WO2007/043677. The anthranilamides M.28.5a) to M.28.5d) and M.28.5h) are described in WO 2007/006670, WO2013/024009 and WO2013/024010, the anthranilamide M.28.5i) is described in WO2011/085575, M.28.5j) in WO2008/134969, M.28.5k) in US2011/046186 and M.28.5l) in WO2012/034403. The diamide compounds M.28.6 and M.28.7 can be found in CN102613183. The spiroketal-substituted cyclic ketoenol derivative M.29.3 is known from WO2006/089633 and the biphenyl-substituted spirocyclic ketoenol derivative M.29.4 from WO2008/067911. The triazoylphenylsulfide M.29.5 is described in WO2006/043635, and biological control agents on the basis of *Bacillus firmus* are described in WO2009/124707. The compounds M.29.6a) to M.29.6i) listed under M.29.6 are described in WO2012/029672, and M.29.6j) and M.29.6k) in WO2013/129688. The nematicide M.29.8 is known from WO2013/055584. The isoxazoline M.29.9.a) is described in WO2013/050317. The isoxazoline M.29.9.b) is described in WO2014/126208. The pyridalyl-type analogue M.29.10 is known from WO2010/060379. The carboxamides broflanilide and M.29.11.b) to M.29.11.h) are described in WO2010/018714, and the carboxamides M.29.11i) to M.29.11.p) in WO2010/127926. The pyridylthiazoles M.29.12.a) to M.29.12.c) are known from WO2010/006713, M.29.12.d) and M.29.12.e) are known from WO2012/000896, and M.29.12.f) to M.29.12.m) from WO2010/129497. The compounds M.29.14a) and M.29.14b) are known from WO2007/101369. The pyrazoles M.29.16.a) to M.29.16h) are described in WO2010/034737, WO2012/084670, and WO2012/143317, respectively, and the pyrazoles M.29.16i) and M.29.16j) are described in U.S. 61/891,437.

In a further aspect the present invention relates to an agrochemical mixture comprising at least one fertilizer; and at least one nitrification inhibitor as defined as defined herein above; or at least one fertilizer and a composition as mentioned above.

In the terms of the present invention "agrochemical mixture" means a combination of at least two compounds. The term is, however, not restricted to a physical mixture comprising at least two compounds, but refers to any preparation form of at least one compound and at least one further compound, the use of which many be time- and/or locus-related.

The agrochemical mixtures may, for example, be formulated separately but applied in a temporal relationship, i.e. simultaneously or subsequently, the subsequent application having a time interval which allows a combined action of the compounds.

Furthermore, the individual compounds of the agrochemical mixtures according to the invention such as parts of a kit or parts of the binary mixture may be mixed by the user himself in a suitable mixing device. In specific embodiments further auxiliaries may be added, if appropriate.

The term "fertilizers" is to be understood as chemical compounds applied to promote plant and fruit growth. Fertilizers are typically applied either through the soil (for uptake by plant roots), through soil substituents (also for uptake by plant roots), or by foliar feeding (for uptake through leaves). The term also includes mixtures of one or more different types of fertilizers as mentioned below.

The term "fertilizers" can be subdivided into several categories including: a) organic fertilizers (composed of decayed plant/animal matter), b) inorganic fertilizers (composed of chemicals and minerals) and c) urea-containing fertilizers.

Organic fertilizers include manure, e.g. liquid manure, semi-liquid manure, biogas manure, stable manure or straw manure, slurry, worm castings, peat, seaweed, compost, sewage, and guano. Green manure crops are also regularly grown to add nutrients (especially nitrogen) to the soil. Manufactured organic fertilizers include compost, blood meal, bone meal and seaweed extracts. Further examples are enzyme digested proteins, fish meal, and feather meal. The decomposing crop residue from prior years is another source of fertility. In addition, naturally occurring minerals such as mine rock phosphate, sulfate of potash and limestone are also considered inorganic fertilizers.

Inorganic fertilizers are usually manufactured through chemical processes (such as the Haber process), also using naturally occurring deposits, while chemically altering them (e.g. concentrated triple superphosphate). Naturally occurring inorganic fertilizers include Chilean sodium nitrate, mine rock phosphate, limestone, and raw potash fertilizers.

The inorganic fertilizer may, in a specific embodiment, be a NPK fertilizer. "NPK fertilizers" are inorganic fertilizers formulated in appropriate concentrations and combinations comprising the three main nutrients nitrogen (N), phosphorus (P) and potassium (K) as well as typically S, Mg, Ca, and trace elements.

Urea-containing fertilizer may, in specific embodiments, be urea, formaldehyde urea, anhydrous ammonium, urea ammonium nitrate (UAN) solution, urea sulfur, urea based NPK-fertilizers, or urea ammonium sulfate. Also envisaged is the use of urea as fertilizer. In case urea-containing fertilizers or urea are used or provided, it is particularly preferred that urease inhibitors as defined herein above may be added or additionally be present, or be used at the same time or in connection with the urea-containing fertilizers.

Fertilizers may be provided in any suitable form, e.g. as solid coated or uncoated granules, in liquid or semi-liquid form, as sprayable fertilizer, or via fertigation etc.

Coated fertilizers may be provided with a wide range of materials. Coatings may, for example, be applied to granular or prilled nitrogen (N) fertilizer or to multi-nutrient fertilizers. Typically, urea is used as base material for most coated fertilizers. Alternatively, ammonium or NPK fertilizers are used as base material for coated fertilizers. The present invention, however, also envisages the use of other base materials for coated fertilizers, any one of the fertilizer materials defined herein. In certain embodiments, elemental sulfur may be used as fertilizer coating. The coating may be performed by spraying molten S over urea granules, followed by an application of sealant wax to close fissures in the coating. In a further embodiment, the S layer may be covered with a layer of organic polymers, preferably a thin layer of organic polymers.

Further envisaged coated fertilizers may be provided by reacting resin-based polymers on the surface of the fertilizer granule. A further example of providing coated fertilizers includes the use of low permeability polyethylene polymers in combination with high permeability coatings.

In specific embodiments the composition and/or thickness of the fertilizer coating may be adjusted to control, for example, the nutrient release rate for specific applications. The duration of nutrient release from specific fertilizers may vary, e.g. from several weeks to many months. The presence of nitrification inhibitors in a mixture with coated fertilizers may accordingly be adapted. It is, in particular, envisaged that the nutrient release involves or is accompanied by the release of an nitrification inhibitor according to the present invention.

Coated fertilizers may be provided as controlled release fertilizers (CRFs). In specific embodiments these controlled release fertilizers are fully coated urea or N—P—K fertilizers, which are homogeneous and which typically show a pre-defined longevity of release. In further embodiments, the CRFs may be provided as blended controlled release fertilizer products which may contain coated, uncoated and/or slow release components. In certain embodiments, these coated fertilizers may additionally comprise micronutrients. In specific embodiments these fertilizers may show a pre-defined longevity, e.g. in case of N—P—K fertilizers.

Additionally envisaged examples of CRFs include patterned release fertilizers. These fertilizers typically show a pre-defined release patterns (e.g. hi/standard/lo) and a pre-defined longevity. In exemplary embodiments fully coated N—P—K, Mg and micronutrients may be delivered in a patterned release manner.

Also envisaged are double coating approaches or coated fertilizers based on a programmed release.

In further embodiments the fertilizer mixture may be provided as, or may comprise or contain a slow release fertilizer. The fertilizer may, for example, be released over any suitable period of time, e.g. over a period of 1 to 5 months, preferably up to 3 months. Typical examples of ingredients of slow release fertilizers are IBDU (isobutylidenediurea), e.g. containing about 31-32% nitrogen, of which 90% is water insoluble; or UF, i.e. an urea-formaldehyde product which contains about 38% nitrogen of which about 70% may be provided as water insoluble nitrogen; or CDU (crotonylidene diurea) containing about 32% nitrogen; or MU (methylene urea) containing about 38 to 40% nitrogen, of which 25-60% is typically cold water insoluble nitrogen; or MDU (methylene diurea) containing about 40% nitrogen, of which less than 25% is cold water insoluble nitrogen; or MO (methylol urea) containing about 30% nitrogen, which may typically be used in solutions; or DMTU (diimethylene triurea) containing about 40% nitrogen, of which less than 25% is cold water insoluble nitrogen; or TMTU (tri methylene tetraurea), which may be provided as component of UF products; or TMPU (tri methylene pentaurea), which may also be provided as component of UF products; or UT (urea triazone solution) which typically contains about 28% nitrogen. The fertilizer mixture may also be long-term nitrogen-bearing fertilizer containing a mixture of acetylene diurea and at least one other organic nitrogen-bearing fertilizer selected from methylene urea, isobutylidene diurea, crotonylidene diurea, substituted triazones, triuret or mixtures thereof.

Any of the above mentioned fertilizers or fertilizer forms may suitably be combined. For instance, slow release fertilizers may be provided as coated fertilizers. They may also be combined with other fertilizers or fertilizer types. The same applies to the presence of a nitrification inhibitor according to the present invention, which may be adapted to the form and chemical nature of the fertilizer and accordingly be provided such that its release accompanies the release of the fertilizer, e.g. is released at the same time or with the same frequency. The present invention further envisages fertilizer or fertilizer forms as defined herein above in combination with nitrification inhibitors as defined herein above and further in combination with urease inhibitors as defined herein above. Such combinations may be provided as coated or uncaoted forms and/or as slow or fast release forms. Preferred are combinations with slow release fertilizers including a coating. In further embodiments, also different release schemes are envisaged, e.g. a slower or a faster release.

The term "fertigation" as used herein refers to the application of fertilizers, optionally soil amendments, and optionally other water-soluble products together with water through an irrigation system to a plant or to the locus where a plant is growing or is intended to grow, or to a soil substituent as defined herein below. For example, liquid fertilizers or dissolved fertilizers may be provided via fertigation directly to a plant or a locus where a plant is growing or is intended to grow. Likewise, nitrification inhibitors according to the present invention, or in combination with additional nitrification inhibitors, may be provided via fertigation to plants or to a locus where a plant is growing or is intended to grow. Fertilizers and nitrification inhibitors according to the present invention, or in combination with additional nitrification inhibitors, may be provided together, e.g. dissolved in the same charge or load of material (typically water) to be irrigated. In further embodiments, fertilizers and nitrification inhibitors may be provided at different points in time. For example, the fertilizer may be fertigated first, followed by the nitrification inhibitor, or preferably, the nitrification inhibitor may be fertigated first, followed by the fertilizer. The time intervals for these activities follow the herein above outlined time intervals for the application of fertilizers and nitrification inhibitors. Also envisaged is a repeated fertigation of fertilizers and nitrification inhibitors according to the present invention, either together or intermittently, e.g. every 2 hours, 6 hours, 12 hours, 24 hours, 2 days, 3 days, 4 days, 5 days, 6 days or more.

In particularly preferred embodiments, the fertilizer is an ammonium-containing fertilizer.

The agrochemical mixture according to the present invention may comprise one fertilizer as defined herein above and one nitrification inhibitor of formula I as defined herein above. In further embodiments, the agrochemical mixture according to the present invention may comprise at least one or more than one fertilizer as defined herein above, e.g. 2, 3, 4, 5, 6, 6, 7, 8, 9, 10 or more different fertilizers (including inorganic, organic and urea-containing fertilizers) and at least one nitrification inhibitor of formula I as defined herein above, preferably one nitrification inhibitor of formula I selected from Table 1.

In another group of embodiments the agrochemical mixture according to the present invention may comprise at least one or more than one nitrification inhibitor of formula I as defined herein above, preferably more than one nitrification inhibitor of formula I selected from Table 1, e.g. 2, 3, 4, 5, 6, 6, 7, 8, 9, 10 or more different nitrification inhibitors as defined herein above or as provided in Table 1 and at least one fertilizer as defined herein above.

The term "at least one" is to be understood as 1, 2, 3 or more of the respective compound selected from the group consisting of fertilizers as defined herein above (also designated as compound A), and nitrification inhibitors of formula I as defined herein above (also designated as compound B).

In addition to at least one fertilizer and at least one nitrification inhibitor as defined herein above, an agrochemical mixture may comprise further ingredients, compounds, active compounds or compositions or the like. For example, the agrochemical mixture may additionally comprise or composed with or on the basis of a carrier, e.g. an agrochemical carrier, preferably as defined herein. In further embodiments, the agrochemical mixture may further comprise at least one pesticidal compound. For example, the agrochemical mixture may additionally comprise at least one herbicidal compound and/or at least one fungicidal compound and/or at least one insecticidal compound.

In further embodiments, the agrochemical mixture may, in addition to the above indicated ingredients, in particular in addition to the nitrification inhibitor of the compound of formula I and the fertilizer, further comprise alternative or additional nitrification inhibitors such as linoleic acid, alpha-linolenic acid, methyl p-coumarate, methyl ferulate, MHPP, Karanjin, brachialacton, p-benzoquinone sorgoleone, nitrapyrin, dicyandiamide (DCD), 3,4-dimethyl pyrazole phosphate (DMPP), 4-amino-1,2,4-triazole hydrochloride (ATC), 1-amido-2-thiourea (ASU), 2-amino-4-chloro-6-methylpyrimidine (AM), 5-ethoxy-3-trichloromethyl-1,2,4-thiodiazole (terrazole), ammoniumthiosulfate (ATU), 3-methylpyrazol (3-MP), 3,5-dimethylpyrazole (DMP), 1,2, 4-triazol and thiourea (TU) and/or sulfathiazole (ST), N-(1H-pyrazolyl-methyl)acetamides such as N-((3(5)-methyl-1H-pyrazole-1-yl)methyl)acetamide, and/or N-(1H-pyrazolyl-methyl)formamides such as N-((3(5)-methyl-1H-pyrazole-1-yl)methyl formamide, N-(4-chloro-3(5)-methyl-pyrazole-1-ylmethyl)-formamide, or N-(3(5),4-dimethyl-pyrazole-1-ylmethyl)-formamide.

Furthermore, the invention relates to a method for reducing nitrification, comprising treating a plant growing on soil and/or the locus where the plant is growing or is intended to grow with at least one nitrification inhibitor as defined herein above, i.e. with an nitrification inhibitor being a compound of formula I, or a derivative thereof, or a composition comprising said nitrification inhibitor.

The term "plant" is to be understood as a plant of economic importance and/or men-grown plant. In certain embodiments, the term may also be understood as plants which have no or no significant economic importance. The plant is preferably selected from agricultural, silvicultural and horticultural (including ornamental) plants. The term also relates to genetically modified plants.

The term "plant" as used herein further includes all parts of a plant such as germinating seeds, emerging seedlings, plant propagules, herbaceous vegetation as well as established woody plants including all belowground portions (such as the roots) and aboveground portions.

Within the context of the method for reducing nitrification it is assumed that the plant is growing on soil. In specific embodiments, the plant may also grow differently, e.g. in synthetic laboratory environments or on soil substituents, or be supplemented with nutrients, water etc. by artificial or technical means. In such scenarios, the invention envisages a treatment of the zone or area where the nutrients, water etc. are provided to the plant. Also envisaged is that the plant grows in green houses or similar indoor facilities.

The term "locus" is to be understood as any type of environment, soil, soil substituent, area or material where the plant is growing or intended to grow. Preferably, the term relates to soil or soil substituent on which a plant is growing.

In one embodiment, the plant to be treated according to the method of the invention is an agricultural plant. "Agricultural plants" are plants of which a part (e.g. seeds) or all is harvested or cultivated on a commercial scale or which serve as an important source of feed, food, fibers (e.g. cotton, linen), combustibles (e.g. wood, bioethanol, biodiesel, biomass) or other chemical compounds. Preferred agricultural plants are for example cereals, e.g. wheat, rye, barley, triticale, oats, corn, sorghum or rice, beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, oil-seed rape, canola, linseed, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, canola, sugar cane or oil palm; tobacco; nuts; coffee; tea; bananas; vines (table grapes and grape juice grape vines); hop; turf; natural rubber plants.

In a further embodiment, the plant to be treated according to the method of the invention is a horticultural plant. The term "horticultural plants" are to be understood as plants which are commonly used in horticulture, e.g. the cultivation of ornamentals, vegetables and/or fruits. Examples for ornamentals are turf, geranium, pelargonia, *petunia, begonia* and fuchsia. Examples for vegetables are potatoes, tomatoes, peppers, cucurbits, cucumbers, melons, watermelons, garlic, onions, carrots, cabbage, beans, peas and lettuce and more preferably from tomatoes, onions, peas and lettuce. Examples for fruits are apples, pears, cherries, strawberry, citrus, peaches, apricots and blueberries.

In a further embodiment, the plant to be treated according to the method of the invention is an ornamental plant. "Ornamental plants" are plants which are commonly used in gardening, e.g. in parks, gardens and on balconies. Examples are turf, geranium, pelargonia, *petunia, begonia* and fuchsia.

In another embodiment of the present invention, the plant to be treated according to the method of the invention is a silvicultural plant. The term "silvicultural plant" is to be understood as trees, more specifically trees used in reforestation or industrial plantations. Industrial plantations generally serve for the commercial production of forest products, such as wood, pulp, paper, rubber tree, Christmas trees, or young trees for gardening purposes. Examples for silvicultural plants are conifers, like pines, in particular *Pinus* spec., fir and spruce, *eucalyptus*, tropical trees like teak, rubber tree, oil palm, willow (Salix), in particular Salix spec., poplar (cottonwood), in particular *Populus* spec., beech, in particular *Fagus* spec., birch, oil palm, and oak.

The term "plant propagation material" is to be understood to denote all the generative parts of the plant such as seeds and vegetative plant material such as cuttings and tubers (e.g. potatoes), which can be used for the multiplication of the plant. This includes seeds, grains, roots, fruits, tubers, bulbs, rhizomes, cuttings, spores, offshoots, shoots, sprouts and other parts of plants, including seedlings and young plants, which are to be transplanted after germination or after emergence from soil, meristem tissues, single and multiple plant cells and any other plant tissue from which a complete plant can be obtained.

The term "genetically modified plants" is to be understood as plants, which genetic material has been modified by the use of recombinant DNA techniques in a way that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; aceto-lactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073.

The methods for producing such genetically modified plants are generally known to the person skilled in the art and are described, e.g. in the publications mentioned above.

These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the Mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The term "soil substituent" as used herein refers to a substrate which is able to allow the growth of a plant and does not comprise usual soil ingredients. This substrate is typically an anorganic substrate which may have the function of an inert medium. It may, in certain embodiments, also comprise organic elements or portions. Soil substituents may, for example, be used in hydroculture or hydroponic approaches, i.e. wherein plants are grown in soilless medium and/or aquatic based environments. Examples of suitable soil substituents, which may be used in the context of the present invention, are perlite, gravel, biochar, mineral wool, coconut husk, phyllosilicates, i.e. sheet silicate minerals, typically formed by parallel sheets of silicate tetrahedra with $Si_2O_5$ or a 2:5 ratio, or clay aggregates, in particular expanded clay aggregates with a diameter of about 10 to 40 mm. Particularly preferred is the employment of vermiculite, i.e. a phyllosilicate with 2 tetrahedral sheets for every one octahedral sheet present.

The use of soil substituents may, in specific embodiments, be combined with fertigation or irrigation as defined herein.

In specific embodiments, the treatment may be carried out during all suitable growth stages of a plant as defined herein. For example, the treatment may be carried out during the BBCH principle growth stages.

The term "BBCH principal growth stage" refers to the extended BBCH-scale which is a system for a uniform coding of phenologically similar growth stages of all mono- and dicotyledonous plant species in which the entire developmental cycle of the plants is subdivided into clearly recognizable and distinguishable longer-lasting developmental phases. The BBCH-scale uses a decimal code system, which is divided into principal and secondary growth stages. The abbreviation BBCH derives from the Federal Biological Research Centre for Agriculture and Forestry (Germany), the Bundessortenamt (Germany) and the chemical industry.

In one embodiment the invention relates to a method for reducing nitrification comprising treating a plant growing on soil or soil substituents and/or the locus where the plant is growing or is intended to grow with at least one nitrification inhibitor as defined herein above, i.e. with a nitrification inhibitor being a compound of formula I, or a derivative thereof at a growth stage (GS) between GS 00 and GS>BBCH 99 of the pant (e.g. when fertilizing in fall after harvesting apples) and preferably between GS 00 and GS 65 BBCH of the plant.

In one embodiment the invention relates to a method for reducing nitrification comprising treating a plant growing on soil or soil substituents and/or the locus where the plant is growing or is intended to grow with at least one nitrification inhibitor as defined herein above, i.e. with a nitrification inhibitor being a compound of formula I, or a derivative thereof at a growth stage (GS) between GS 00 to GS 45, preferably between GS 00 and GS 40 BBCH of the plant.

In a preferred embodiment the invention relates to a method for reducing nitrification comprising treating a plant growing on soil or soil substituents and/or the locus where the plant is growing or is intended to grow with at least one nitrification inhibitor as defined herein above, i.e. with a nitrification inhibitor being a compound of formula I, or a derivative thereof at an early growth stage (GS), in particular a GS 00 to GS 05, or GS 00 to GS 10, or GS 00 to GS 15, or GS 00 to GS 20, or GS 00 to GS 25 or GS 00 to GS 33 BBCH of the plant. In particularly preferred embodiments, the method for reducing nitrification comprises treating a plant growing on soil or soil substituents and/or the locus where the plant is growing or is intended to grow with at least one nitrification inhibitor as defined herein above during growth stages including GS 00.

In a further, specific embodiment of the invention, at least one nitrification inhibitor as defined herein above, i.e. a nitrification inhibitor being a compound of formula I, or a derivative thereof is applied to a plant growing on soil or soil substituents and/or the locus where the plant is growing or is intended to grow at a growth stage between GS 00 and GS 55 BBCH, or of the plant.

In a further embodiment of the invention, at least one nitrification inhibitor as defined herein above, i.e. a nitrification inhibitor being a compound of formula I, or a derivative thereof is applied to a plant growing on soil or soil substituents and/or the locus where the plant is growing or is intended to grow at the growth stage between GS 00 and GS 47 BBCH of the plant.

In one embodiment of the invention, at least one nitrification inhibitor as defined herein above, i.e. a nitrification inhibitor being a compound of formula I, or a derivative thereof is applied to a plant growing on soil or soil substituents and/or the locus where the plant is growing or is intended to grow before and at sowing, before emergence, and until harvest (GS 00 to GS 89 BBCH), or at a growth stage (GS) between GS 00 and GS 65 BBCH of the plant.

In a preferred embodiment the invention relates to a method for reducing nitrification comprising treating a plant growing on soil or soil substituents and/or the locus where the plant is growing with at least one nitrification inhibitor as defined herein above, i.e. with a nitrification inhibitor being a compound of formula I, or a derivative thereof wherein the plant and/or the locus where plant is growing or is intended to grow is additionally provided with at least one fertilizer. The fertilizer may be any suitable fertilizer, preferably a fertilizer as defined herein above. Also envisaged is the application of more than one fertilizer, e.g. 2, 3, 4, 5, 6, 7, 8, 9, 10 fertilizers, or of different fertilizer classes or categories.

In specific embodiments of the invention, at least one nitrification inhibitor as defined herein above, i.e. a nitrification inhibitor being a compound of formula I, or a derivative thereof and at least one fertilizer is applied to a plant growing on soil or soil substituents and/or the locus where the plant is growing or is intended to grow at a growth stage between GS 00 and GS 33 BBCH of the plant.

In specific embodiments of the invention, at least one nitrification inhibitor as defined herein above, i.e. a nitrification inhibitor being a compound of formula I, or a derivative thereof and at least one fertilizer is applied to a plant growing on soil or soil substituents and/or the locus where the plant is growing or is intended to grow at a growth stage between GS 00 and GS 55 BBCH of the plant.

In further specific embodiments of the invention, at least one nitrification inhibitor as defined herein above, i.e. a nitrification inhibitor being a compound of formula I, or a derivative thereof and at least one fertilizer is applied to a plant growing on soil or soil substituents and/or the locus where the plant is growing or is intended to grow at sowing, before emergence, or at a growth stage (GS) between GS 00 and GS>BBCH 99 of the pant (e.g. when fertilizing in fall after harvesting apples) and preferably between GS 00 and GS 65 BBCH of the plant.

According to a preferred embodiment of the present invention the application of said nitrification inhibitor and of said fertilizer as defined herein above is carried out simultaneously or with a time lag. The term "time lag" as used herein means that either the nitrification inhibitor is applied before the fertilizer to the plant growing on soil or soil substituents and/or the locus where the plant is growing or is intended to grow; or the fertilizer is applied before the nitrification inhibitor to the plant growing on soil or soil substituents and/or the locus where the plant is growing or is intended to grow. Such time lag may be any suitable period of time which still allows to provide a nitrification inhibiting effect in the context of fertilizer usage. For example, the time lag may be a time period of 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months or more or any time period in between the mentioned time periods. Preferably, the time lag is an interval of 1 day, 2 days, 3 days, 1 week, 2 weeks or 3 weeks. The time lag preferably refers to situations in which the nitrification inhibitor as defined above is provided 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months or more or any time period in between the mentioned time periods before the application of a fertilizer as defined herein above.

In another specific embodiment of the invention at least one nitrification inhibitor as defined herein above, i.e. a nitrification inhibitor being a compound of formula I, or a derivative thereof is applied between GS 00 to GS 33 BBCH of the plant, or between GS 00 and GS 65 BBCH of the plant, provided that the application of at least one fertilizer as defined herein above is carried out with a time lag of at least 1 day, e.g. a time lag of 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, or more or any time period in between the mentioned time periods. It is preferred that the nitrification inhibitors, which is applied between GS 00 to GS 33 BBCH of the plant, is provided 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, or 12 weeks before the application of a fertilizer as defined herein above.

In another specific embodiment of the invention, at least one fertilizer as defined herein above is applied between GS 00 to GS 33 BBCH of the plant or between GS 00 and GS 65 BBCH of the plant, provided that the application of at least one nitrification inhibitor as defined herein above, i.e. of a nitrification inhibitor being a compound of formula I, or a derivative thereof, is carried out with a time lag of at least 1 day, e.g. a time lag of 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks or more or any time period in between the mentioned time periods.

According to a specific embodiment of the present invention a plant growing on soil or soil substituents and/or the locus where the plant is growing or is intended to grow is treated at least once with a nitrification inhibitor as defined herein above, i.e. with a nitrification inhibitor being a compound of formula I, or a derivative thereof. In a further specific embodiment of the present invention a plant growing on soil or soil substituents and/or the locus where the plant is growing or is intended to grow is treated at least once with a nitrification inhibitor as defined herein above, i.e.

with a nitrification inhibitor being a compound of formula I, or a derivative thereof, and at least once with a fertilizer as defined herein above.

The term "at least once" means that the application may be performed one time, or several times, i.e. that a repetition of the treatment with a nitrification inhibitor and/or a fertilizer may be envisaged. Such a repetition may a 2 times, 3 times, 4 times, 5 times, 6 times, 7 times, 8 times, 9 times, 10 times or more frequent repetition of the treatment with a nitrification inhibitor and/or a fertilizer. The repetition of treatment with a nitrification inhibitor and a fertilizer may further be different. For example, while the fertilizer may be applied only once, the nitrification inhibitor may be applied 2 times, 3 times, 4 times etc. Alternatively, while the nitrification inhibitor may be applied only once, the fertilizer may be applied 2 times, 3 times, 4 times etc. Further envisaged are all combination of numerical different numbers of repetitions for the application of a nitrification inhibitor and a fertilizer as defined herein above.

Such a repeated treatment may further be combined with a time lag between the treatment of the nitrification inhibitor and the fertilizer as described above.

The time interval between a first application and second or subsequent application of a nitrification inhibitor and/or a fertilizer may be any suitable interval. This interval may range from a few seconds up to 3 months, e.g. from a few seconds up to 1 month, or from a few seconds up to 2 weeks. In further embodiments, the time interval may range from a few seconds up to 3 days or from 1 second up to 24 hours.

In further specific embodiments, a method for reducing nitrification as described above is carried out by treating a plant growing on soil or soil substituents and/or the locus where the plant is growing or is intended to grow with at least one agrochemical mixture as defined herein above, or with a composition for reducing nitrification as defined herein above.

In another embodiment of the invention, an agrochemical mixture comprising an ammonium- or urea-containing fertilizer and at least one nitrification inhibitor as defined herein above is applied before and at sowing, before emergence, and until GS>BBCH 99 of the pant (e.g. when fertilizing in fall after harvesting apples In case the agrochemical mixture is provided as kit of parts or as non-physical mixture, it may be applied with a time lag between the application of the nitrification inhibitor and the fertilizer or between the application of the nitrification inhibitor a secondary or further ingredient, e.g. a pesticidal compound as mentioned herein above.

In a further embodiment plant propagules are preferably treated simultaneously (together or separately) or subsequently.

The term "propagules" or "plant propagules" is to be understood to denote any structure with the capacity to give rise to a new plant, e.g. a seed, a spore, or a part of the vegetative body capable of independent growth if detached from the parent. In a preferred embodiment, the term "propagules" or "plant propagules" denotes for seed.

For a method as described above, or for a use according to the invention, in particular for seed treatment and in furrow application, the application rates of nitrification inhibitors, i.e. of the compound of formula I are between 0.01 g and 5 kg of active ingredient per hectare, preferably between 1 g and 1 kg of active ingredient per hectare, especially preferred between 50 g and 300 g of active ingredient per hectare depending on different parameters such as the specific active ingredient applied and the plant species treated. In the treatment of seed, amounts of from 0.001 g to 20 g per kg of seed, preferably from 0.01 g to 10 g per kg of seed, more preferably from 0.05 to 2 g per kg of seed of nitrification inhibitors may be generally required.

As a matter of course, if nitrification inhibitors and fertilizers (or other ingredients), or if mixtures thereof are employed, the compounds may be used in an effective and non-phytotoxic amount. This means that they are used in a quantity which allows to obtain the desired effect but which does not give rise to any phytotoxic symptoms on the treated plant or on the plant raised from the treated propagule or treated soil or soil substituents. For the use according to the invention, the application rates of fertilizers may be selected such that the amount of applied N is between 10 kg and 1000 kg per hectare, preferably between 50 kg and 700 kg per hectare.

The nitrification inhibitor compounds according to the invention, e.g. compound I as defined herein above, or derivative thereof as defined herein above can be present in different structural or chemical modifications whose biological activity may differ. They are likewise subject matter of the present invention.

The nitrification inhibitor compounds according to the invention, their N-oxides and/or salts etc. may be converted into customary types of compositions, e.g. agrochemical or agricultural compositions such as solutions, emulsions, suspensions, dusts, powders, pastes and granules.

The composition type depends on the particular intended purpose; in each case, it should ensure a fine and uniform distribution of the compound according to the invention. Examples for composition types are suspensions (SC, 00, FS), emulsifiable concentrates (EC), emulsions (EW, EO, ES), microemulsions (ME), pastes, pastilles, wettable powders or dusts (WP, SP, SS, WS, OP, OS) or granules (GR, FG, GG, MG), which can be watersoluble or wettable, as well as gel formulations for the treatment of plant propagation materials such as seeds (GF). Usually the composition types (e.g. SC, 00, FS, EC, WG, SG, WP, SP, SS, WS, GF) are employed diluted. Composition types such as OP, OS, GR, FG, GG and MG are usually used undiluted.

The compositions are prepared in a known manner (see, for example, U.S. Pat. No. 3,060,084, EP 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 und ff. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001). Compositions or mixtures may also comprise auxiliaries which are customary, for example, in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations). Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Suitable surfactants (adjuvants, wetters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, GermanY), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof. Examples of suitable thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

In specific embodiments, bactericides may be added for preservation and stabilization of the composition. Examples for suitable bactericides are those based on dichlorophene and benzyl alcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin. Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes, e.g. rhodamin B, C. I. pigment red 112, C. I. solvent red 1, pigment blue 15:4, pigment blue 15:3, pigment blue 15:2, pigment blue 15: 1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Furthermore odorous substances may be present in the compositions as defined above. Such odorous substances comprise citronellynitril, citral, zertrahydrolinalool, tetrahydrogeraniol, geranonitril, beta-lonon R, rootanol, linalylacetat, morillol, and p-cresometylether.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding compound of formula I and, if appropriate, further active substances, with at least one solid carrier. Granules, e.g. coated granules, impregnated granules and homogeneous granules, can be prepared by binding the active substances to solid carriers. Examples of such suitable solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g. ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types are:

i) Water-soluble concentrates (SL, LS) 10 parts by weight of a nitrification inhibitor such as a compound of formula I according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.

ii) Dispersible concentrates (DC) 20 parts by weight of a nitrification inhibitor such as a compound of formula I according to the invention are dissolved in 70 parts by weight of cyclohexanone with addition of 10 parts by weight of a dispersant, e.g. polyvinylpyrrolidone. Dilution with water gives a dispersion. The active substance content is 20% by weight.

iii) Emulsifiable concentrates (EC) 15 parts by weight of a nitrification inhibitor such as a compound of formula I according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES) 25 parts by weight of a nitrification inhibitor such as a compound of formula I according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, 00, FS) In an agitated ball mill, 20 parts by weight of a nitrification inhibitor such as a compound of formula I according to the invention are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-dispersible granules and water-soluble granules (WG, SG) 50 parts by weight of a nitrification inhibitor such as a compound of formula I according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-dispersible powders and water-soluble powders (WP, SP, SS, WS) 75 parts by weight of a nitrification inhibitor such as a compound of formula I according to the invention are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF) In an agitated ball mill, 20 parts by weight of a nitrification inhibitor such as a compound of formula I according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained. 2. Composition types to be applied undiluted ix) Oustable powders (OP, OS) 5 parts by weight of a nitrification inhibitor such as a compound of formula I according to the invention are ground finely and mixed intimately with 95 parts by weight of finely divided kaolin. This gives a dustable composition having an active substance content of 5% by weight.

x) Granules (GR, FG, GG, MG) 0.5 parts by weight of a nitrification inhibitor such as a compound of formula I according to the invention is ground finely and associated with 99.5 parts by weight of carriers. Current methods are extrusion, spray-drying or the fluidized bed. This gives granules to be applied undiluted having an active substance content of 0.5-10% by weight, preferably an active substance content of 0.5-2% by weight.

xi) ULV solutions (UL) 10 parts by weight of a nitrification inhibitor such as a compound of formula I according to the invention are dissolved in 90 parts by weight of an organic solvent, e.g. xylene. This gives a composition to be applied undiluted having an active substance content of 10% by weight.

The compositions, e.g. agrochemical or agriculatural compositons, generally comprise between 0.01 and 95%, preferably between 0.1 and 90%, most preferably between 0.5 and 90%, by weight of active substance. The active substances are employed in a purity offrom 90% to 100%, preferably from 95% to 100% (according to NMR spectrum).

Water-soluble concentrates (LS), flowable concentrates (FS), powders for dry treatment (OS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds.

These compositions can be applied to plant propagation materials, particularly seeds, diluted or undiluted.

The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying or treating agrochemical or agricultural compounds or mixtures, or compositions as defined herein, respectively, on to plant propagation material, especially seeds, the plant and/or the locus where the plant is growing or intended to grow are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting.

In a preferred embodiment, a suspension-type (FS) composition may be used. Typically, a FS composition may comprise 1-800 g/l of active substance, 1 200 g/l surfactant, o to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring.

The application forms depend entirely on the intended purposes; it is intended to ensure in each case the finest possible distribution of the active substances according to the invention. Aqueous application forms can be prepared from emulsion concentrates, pastes or wettable powders (sprayable powders, oil dispersions) by adding water.

To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 90%, such as from 30 to 80%, e.g. from 35 to 45% or from 65 to 75% by weight of active substance. The active substances may also be used successfully in the ultra-low-volume process (ULV), it being possible to apply compositions comprising over 95% by weight of active substance, or even to apply the active substance without additives.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

In a further aspect the invention relates to a method for treating a fertilizer or a composition. This treatment includes the application of a nitrification inhibitor which is a compound of formula I as defined herein above to a fertilizer or a composition. The treatment may accordingly result in the presence of said nitrification inhibitor in a preparation of fertilizers or other compositions. Such treatment may, for example, result in a homogenous distribution of nitrification inhibitors on or in fertilizer preparations. Treatment processes are known to the skilled person and may include, for instance, dressing, coating, pelleting, dusting or soaking. In a specific embodiment, the treatment may be a coating of nitrification inhibitors with fertilizer preparations, or a coating of fertilizers with nitrification inhibitors. The treatment may be based on the use of granulation methods as known to the skilled person, e.g. fluidized bed granulation. The treatment may, in certain embodiments, be performed with a composition comprising the nitrification inhibitor as defined herein above, e.g. comprising besides the inhibitor a carrier or a pesticide or any other suitable additional compound as mentioned above.

In a further specific embodiment, the present invention relates to a method for treating seed or plant propagation material. The term "seed treatment" as used herein refers to or involves steps towards the control of biotic stresses on or in seed and the improvement of shooting and development of plants from seeds. For seed treatment it is evident that a plant suffering from biotic stresses such as fungal or insecticidal attack or which has difficulties obtaining sufficient suitable nitrogen-sources shows reduced germination and emergence leading to poorer plant or crop establishment and vigor, and consequently, to a reduced yield as compared to a plant propagation material which has been subjected to curative or preventive treatment against the relevant pest and which can grow without the damage caused by the biotic stress factor. Methods for treating seed or plant progation material according to the invention thus lead, among other advantages, to an enhanced plant health, a better protection against biotic stresses and an increased plant yield.

Seed treatment methods for applying or treating inventive mixtures and compositions thereof, e.g. compositions or agrochemical compositions as defined herein above, and in particular combinations of nitrification inhibitors as defined herein above and secondary effectors such as pesticides, in particular fungicides, insecticides, and/or nematicides, to plant propagation material, especially seeds, are known in the art, and include dressing, coating, filmcoating, pelleting and soaking application methods of the propagation material. Such methods are also applicable to the combinations or compositions according to the invention.

In further embodiments, the treatment of seeds is performed with compositions comprising, besides a nitrification inhibitor according to the present invention, e.g. compositions as defined herein above, a fungicide and an insecticide, or a fungicide and a nematicide, or an insecticide and a nematicide, or a combination of a fungicide, insecticide and nematicide etc.

In a preferred embodiment, the agricultural compositon or combination comprising a nitrification inhibitor according to the present invention, e.g. as defined herein above, is applied or treated on to the plant propagation material by a method such that the germination is not negatively impacted. Accordingly, examples of suitable methods for applying (or treating) a plant propagation material, such as a seed, is seed dressing, seed coating or seed pelleting and alike. It is preferred that the plant propagation material is a seed, seed piece (i.e. stalk) or seed bulb.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the ingredients in compositions or mixtures as defined herein and adherence thereof to the seeds is desired during propagation material treatment. Treatment could vary from a thin film (dressing) of the formulation containing the combination, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colorants) where the original shape and/or size of the seed is no longer recognizable.

An aspect of the present invention includes application of the composition, e.g. agricultural composition or combination comprising a nitrification inhibitor according to the present invention, e.g. as defined herein above, onto the plant propagation material in a targeted fashion, including positioning the ingredients in the combination onto the entire plant propagation material or on only parts thereof, including on only a single side or a portion of a single side. One of ordinary skill in the art would understand these application methods from the description provided in EP954213B1 and WO06/112700.

The composition, e.g. agricultural composition or combination comprising a nitrification inhibitor according to the present invention, e.g. as defined herein above, can also be used in form of a "pill" or "pellet" or a suitable substrate and placing, or sowing, the treated pill, or substrate, next to a plant propagation material. Such techniques are known in the art, particularly in EP1124414, WO07/67042, and WO07/67044. Application of the composition, e.g. agricultural composition, or combination comprising a nitrification inhibitor according to the present invention, e.g. as defined herein above, onto plant propagation material also includes protecting the plant propagation material treated with the combination of the present invention by placing one or more pesticide- and nitrification inhibitor (NI)-containing particles next to a pesticide- and NI-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide. Such techniques are known in the art, particularly in WO2005/120226.

Application of the combinations onto the seed also includes controlled release coatings on the seeds, wherein the ingredients of the combinations are incorporated into materials that release the ingredients over time. Examples of controlled release seed treatment technologies are generally known in the art and include polymer films, waxes, or other seed coatings, wherein the ingredients may be incorporated into the controlled release material or applied between layers of materials, or both.

Seed can be treated by applying thereto the compound s present in the inventive mixtures in any desired sequence or simultaneously.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil or soil substituents but would include any application practice that would target the seed during the planting process.

Preferably, the treatment occurs before sowing of the seed so that the sown seed has been pre-treated with the combination. In particular, seed coating or seed pelleting are preferred in the treatment of the combinations according to the invention. As a result of the treatment, the ingredients in each combination are adhered on to the seed and therefore available for pest control.

The treated seeds can be stored, handled, sowed and tilled in the same manner as any other active ingredient treated seed.

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. Preferred examples of seed treatment formulation types or soil application for pre-mix compositions are of WS, LS, ES, FS, WG or CS-type.

The compositions in question give, after two-to-tenfold dilution, active components concentrations of from 0.01 to 60% by weight, preferably from 0.1 to 40%, in the ready-to-use preparations. Application can be carried out before or during sowing. Methods for applying or treating compositions or combinations comprising a nitrification inhibitor according to the present invention, e.g. as defined herein above on to plant propagation material, especially seeds include dressing, coating, pelleting, dusting, soaking and in-furrow application methods of the propagation material. Preferably, compositions or combinations comprising a nitrification inhibitor according to the present invention, e.g. as defined herein above are applied on to the plant propagation material by a method such that germination is not induced, e.g. by seed dressing, pelleting, coating and dusting.

Typically, a pre-mix formulation for seed treatment application comprises 0.5 to 99.9 percent, especially 1 to 95 percent, of the desired ingredients, and 99.5 to 0.1 percent, especially 99 to 5 percent, of a solid or liquid adjuvant (including, for example, a solvent such as water), where the auxiliaries can be a surfactant in an amount of 0 to 50 percent, especially 0.5 to 40 percent, based on the pre-mix formulation. Whereas commercial products will preferably be formulated as concentrates (e.g., pre-mix composition (formulation), the end user will normally employ dilute formulations (e.g. tank mix composition).

When employed in plant protection, the total amounts of active components applied are, depending on the kind of effect desired, from 0.001 to 10 kg per ha, preferably from 0.005 to 2 kg per ha, more preferably from 0.05 to 0.9 kg per ha, in particular from 0.1 to 0.75 kg per ha. The application rates may range from about $1 \times 10^6$ to $5 \times 10^{15}$ (or more) CFU/ha. Preferably, the spore concentration is about $1 \times 10^7$ to about $1 \times 10^{11}$ CFU/ha. In the case of (entomopathogenic) nematodes as microbial pesticides (e.g. Steinernema feltiae), the application rates preferably range inform about $1 \times 10^5$ to $1 \times 10^{12}$ (or more), more preferably from $1 \times 10^8$ to $1 \times 10^{11}$, even more preferably from $5 \times 10^8$ to $1 \times 10^{10}$ individuals (e.g. in the form of eggs, juvenile or any other live stages, preferably in an infetive juvenile stage) per ha.

When employed in plant protection by seed treatment, the amount of compositions or combinations comprising a nitrification inhibitor according to the present invention, e.g. as defined herein above (based on total weight of active components) is in the range from 0.01-10 kg, preferably from 0.1-1000 g, more preferably from 1-100 g per 100 kilogram of plant propagation material (preferably seeds). The application rates with respect to plant propagation material preferably may range from about $1 \times 10^6$ to $1 \times 10^{12}$ (or more) CFU/seed. Preferably, the concentration is about $1 \times 10^6$ to about $1 \times 10^{11}$ CFU/seed. Alternatively, the application rates with respect to plant propagation material may range from about $1 \times 10^7$ to $1 \times 10^{14}$ (or more) CFU per 100 kg of seed, preferably from $1 \times 10^9$ to about $1 \times 10^{11}$ CFU per 100 kg of seed.

The following example is provided for illustrative purposes. It is thus understood that the example is not to be construed as limiting. The skilled person in the art will clearly be able to envisage further modifications of the principles laid out herein.

EXAMPLES

Example 1

The compounds of the invention have been tested as follows in terms of the inhibition of nitrification:

Soil was sampled fresh from a field (e.g. Limburgerhof), dried and sieved through a 500 µm sieve. Approximately 200 mg of soil were placed into each well of a 48 well plate. Compounds, or DMSO alone, were added at a concentration of 10 ppm, dissolved in 1% DMSO. 6 µmol ammonium sulfate was added per well as well as 4.8 mg NaClO$_3$.

Subsequently, the samples were incubated at room temperature for up to 72 hrs. After the incubation period 64 mg KCl were added and mixed. 25 µl of the supernatant were placed into a fresh plate and 260 µl of a color reaction solution (from Merck Nr 1.11799.0100) were added.

Measurements were taken with a Tecan plate Reader at 540 nm wavelength.

The results of the measurements (with a dose of 10 ppm) were that the compounds A-14, A-19, A-33, A-42 and A-44 as shown in Table A, and the compounds B-5 and B-6 as shown in Table B supra demonstrated an inhibition of ≥10% compared to a control (DMSO only).

Inhibition is calculated as x=% activity compared to control, and converted to 100-x to give the value of inhibition, rather than activity.

Example 1.1

The results for the compounds tested with a dose of 10 ppm are provided in the following Table 1.1. In each case, the best inhibition value (IN) obtained for a compound is provided.

TABLE 1.1

| No | Compound | IN |
|---|---|---|
| A-14 | 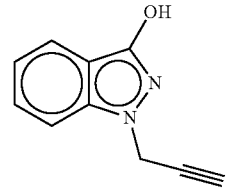 | 59 |

TABLE 1.1-continued

| No | Compound | IN |
|---|---|---|
| A-19 | | 45 |
| A-33 | | 44 |
| A-42 | | 17 |
| B-5 | | >10 |
| B-6 | | >10 |

Example 1.2

The results for the compounds tested with a dose of 5±1 ppm are provided in the following Table 1.2. In each case, the best inhibition value (IN) obtained for a compound is provided

TABLE 1.2

| No | Compound | IN |
|---|---|---|
| A-44 | | 59 |

Comparative Example 1.3

As a reference compound for a known nitrification inhibitor with a terminal alkynyl group, phenylacetylene (U.S. Pat. No. 4,552,581 A) was tested under the same conditions as outlined above with a dose of 10 ppm. The following inhibition value was obtained.

TABLE 1.3

| Name | Structure | IN |
|---|---|---|
| Phenylacetylene | 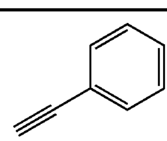 | 7 |

The invention claimed is:

1. A method for reducing nitrification, the method comprising:
applying a composition comprising a compound of Formula I, or a stereoisomer, a salt, a tautomer, or N-oxide thereof, to a locus where nitrification occurs, wherein

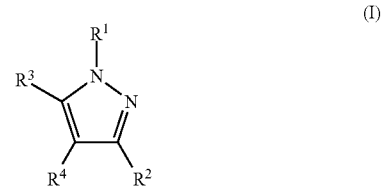

(I)

$R^1$ is $C_4$-$C_6$-alkynyl, propargyl, or $C_3$-$C_6$-allenyl, wherein the C-atoms of these groups optionally carry 1, 2, or 3 identical or different substituents selected from the group consisting of halogen, CN, $OR^a$, $NO_2$, $NR^cR^d$, $NR^b(C=O)R^a$, $O(C=O)R^a$, $C(=O)R^a$, $C(=O)OR^a$, $C(=O)NR^cR^d$, $S(O)_mR^a$, and $S(O)_mNR^cR^d$;

$R^2$, $R^3$ and $R^4$ are independently selected from the group consisting of H, halogen, CN, $OR^a$, $NO_2$, $NR^cR^d$, $NR^b(C=O)R^a$, $C(=O)R^a$, $C(=O)OR^a$, $C(=O)NR^cR^d$, $S(O)_mR^a$, $S(O)_mNR^cR^d$; $C_1$-$C_8$-alkyl, $C_3$-$C_8$-cycloalkyl, $C_2$-$C_8$-alkenyl, $C_2$-$C_8$-alkynyl, wherein the C-atoms of these groups optionally carry 1, 2, or 3 identical or different substituents selected from the group consisting of halogen, CN, $OR^a$, $NO_2$, $NR^cR^d$, $NR^b(C=O)R^a$, $C(=O)R^a$, $C(=O)OR^a$, $C(=O)NR^cR^d$, $S(O)_mR^a$, and $S(O)_mNR^cR^d$; $C_6$-$C_{10}$-aryl, and $C_5$-$C_{10}$-hetaryl, wherein the aromatic moieties optionally carry 1, 2, 3, 4, or 5 identical or different substituents selected from the group consisting of halogen, CN, $OR^a$, $C_1$-$C_4$-alkyl, $C_1$-$C_4$-haloalkyl, $C_2$-$C_4$-alkenyl, and $C_2$-$C_4$-alkynyl;

or $R^3$ and $R^4$ together form a bridge, which forms together with the atoms to which $R^3$ and $R^4$ are bonded an annulated partly or fully unsaturated, or aromatic 5 to 10-membered carbocyclic or heterocyclic ring, wherein the heterocyclic ring may carry 1, 2, or 3 heteroatoms being selected from O, S, and N, of which at least one of S and N may optionally be oxidized, and wherein the carbocyclic or heterocyclic ring optionally carries carries 1, 2, 3, 4, or 5 identical or different substituents selected from the group consisting of =O, halogen, CN, $OR^a$, $NO_2$, $NR^cR^d$, $NR^b(C=O)R^a$, $C(=O)R^a$, $C(=O)OR^a$, $C(=O)NR^cR^d$, $O(C=O)NR^cR^d$, $C_1$-$C_4$-alkyl, $C_1$-$C_4$-haloalkyl, $C_6$-$C_{10}$-aryl, $C_5$-$C_{10}$-hetaryl, $C_5$-$C_{10}$-carbocyclyl, and $C_5$-$C_{10}$-heterocyclyl, wherein the $C_6$-$C_{10}$-aryl, $C_5$-$C_{10}$-hetaryl, $C_5$-$C_{10}$-carbocyclyl, and $C_5$-$C_{10}$-heterocyclyl moieties optionally carry 1, 2, 3, 4, or 5 identical or different substituents selected from the group consisting of =O, halogen, CN, $C_1$-$C_4$-alkyl, and $C_1$-$C_4$-haloalkyl;

or $R^2$ and $R^4$ together form a bridge, which forms together with the atoms to which $R^2$ and $R^4$ are bonded an annulated partly or fully unsaturated, or aromatic 5 to 10-membered carbocyclic or heterocyclic ring, wherein the heterocyclic ring may carry 1, 2, or 3 heteroatoms being selected from O, S, and N, of which at least one of S and N may optionally be oxidized, and wherein the carbocyclic or heterocyclic ring optionally carries carries 1, 2, 3, 4, or 5 identical or different substituents selected from the group consisting of =O, halogen, CN, $OR^a$, $NO_2$, $NR^cR^d$, $NR^b(C=O)R^a$, $C(=O)R^a$, $C(=O)OR^a$, $C(=O)NR^cR^d$, $O(C=O)NR^cR^d$, $C_1$-$C_4$-alkyl, $C_1$-$C_4$-haloalkyl, $C_6$-$C_{10}$-aryl, $C_5$-$C_{10}$-hetaryl, $C_5$-$C_{10}$-carbocyclyl, and $C_5$-$C_{10}$-heterocyclyl, wherein the $C_6$-$C_{10}$-aryl, $C_5$-$C_{10}$-hetaryl, $C_5$-$C_{10}$-carbocyclyl, and $C_5$-$C_{10}$-heterocyclyl moieties optionally carry 1, 2, 3, 4, or 5 identical or different substituents selected from the group consisting of =O, halogen, CN, $C_1$-$C_4$-alkyl, and $C_1$-$C_4$-haloalkyl;

$R^a$ is selected from the group consisting of H, $C_1$-$C_8$-haloalkyl, $C_2$-$C_8$-alkenyl, $C_2$-$C_8$-alkynyl; $C_5$-$C_{10}$-hetaryl and $C_6$-$C_{10}$-aryl, wherein the $C_5$-$C_{10}$-hetaryl or $C_6$-$C_{10}$-aryl moieties optionally carry 1, 2, 3, 4, or 5 identical or different substituents selected from the group consisting of halogen, CN, OH, $C_1$-$C_4$-alkyl, $C_1$-$C_4$-alkoxy, $C_1$-$C_4$-haloalkyl, $C_2$-$C_4$-alkenyl, $C_2$-$C_4$-alkynyl, $C_5$-$C_6$-hetaryl and $C_6$-aryl, wherein said $C_5$-$C_6$-hetaryl and $C_6$-aryl moieties optionally carry 1, 2, 3, 4, or 5 substituents selected from the group consisting of halogen, CN, OH, $C_1$-$C_4$-alkyl, $C_1$-$C_4$-alkoxy, $C_1$-$C_4$-haloalkyl, $C_2$-$C_4$-alkenyl, and $C_2$-$C_4$-alkynyl;

$R^b$ is selected from the group consisting of H, $C_1$-$C_4$-alkyl, $C_3$-$C_8$-cycloalkyl, $C_2$-$C_4$-alkenyl, $C_2$-$C_8$-alkynyl, and $C_6$-$C_{10}$-aryl;

$R^c$ and $R^d$ are independently selected from the group consisting of H, $C_1$-$C_4$-alkyl, $C_1$-$C_4$-haloalkyl, $C_3$-$C_8$-cycloalkyl, $C_6$-$C_{10}$-aryl, and $C_5$-$C_{10}$-hetaryl;

or $R^c$ and $R^d$ together with the N-atom to which they are bonded form a 5- to 6-membered, saturated or unsaturated heterocycle, which may carry a further heteroatom being selected from O, S, and N as a ring member atom, of which at least one S and N may optionally be oxidized, and wherein the heterocyclic ring optionally carries 1, 2, 3, 4, or 5 substituents, which are independently selected from the group consisting of halogen, CN, OH, $NO_2$, $C_1$-$C_4$-alkyl, $C_1$-$C_4$-haloalkyl, $C_1$-$C_4$-alkoxy, and $C_1$-$C_4$-haloalkoxy; and m is 0, 1, or 2.

2. The method according to claim 1, wherein:
$R^1$ is a terminal $C_4$-alkynyl group or propargyl.

3. The method according to claim 1, wherein:
$R^1$ is a terminal $C_3$-$C_4$-allenyl group.

4. The method according to claim 1, wherein:
$R^2$, $R^3$ and $R^4$ are independently selected from the group consisting of H, halogen, CN, $OR^a$, $C(=O)R^a$, $C(=O)OR^a$, $C(=O)NR^cR^d$; $C_1$-$C_8$-alkyl, wherein the C-atoms optionally carry 1, 2, 3 identical or different substituents selected from the group consisting of halogen, CN, $OR^a$; $C_6$-$C_{10}$-aryl, and $C_5$-$C_{10}$-hetaryl, wherein the aromatic moieties optionally carry 1, 2, 3, 4, or 5 identical or different substituents selected from the group consisting of halogen, CN, $OR^a$, $C_1$-$C_4$-alkyl, $C_1$-$C_4$-haloalkyl, and $C_2$-$C_4$-alkynyl;

or $R^3$ and $R^4$ together form a bridge, which forms together with the atoms to which $R^3$ and $R^4$ are bonded an annulated partly or fully unsaturated, or aromatic 5 to 10-membered carbocyclic ring, wherein the carbocyclic ring optionally carries 1, 2, 3, 4, or 5 identical or different substituents selected from the group consisting of =O, halogen, CN, $OR^a$, $O(C=O)NR^cR^d$, $C_5$-$C_{10}$-hetaryl, and $C_5$-$C_{10}$-heterocyclyl, wherein the $C_5$-$C_{10}$-hetaryl, and $C_5$-$C_{10}$-heterocyclyl moieties optionally carry 1, 2, 3, 4, or 5 identical or different substituents selected from the group consisting of =O, halogen, CN, and $C_1$-$C_4$-haloalkyl;

or $R^2$ and $R^4$ together form a bridge, which forms together with the atoms to which $R^2$ and $R^4$ are bonded an annulated partly or fully unsaturated, or aromatic 5 to 10-membered carbocyclic ring, wherein the carbocyclic ring optionally carries 1, 2, 3, 4, or 5 identical or different substituents selected from the group consisting of =O, halogen, CN, $OR^a$, $O(C=O)NR^cR^d$, $C_5$-$C_{10}$-hetaryl, and $C_5$-$C_{10}$-heterocyclyl, wherein the $C_5$-$C_{10}$-hetaryl, and $C_5$-$C_{10}$-heterocyclyl moieties optionally carry 1, 2, 3, 4, or 5 identical or different substituents selected from the group consisting of =O, halogen, CN, and $C_1$-$C_4$-haloalkyl;

$R^a$ is selected from the group consisting of H, $C_1$-$C_8$-alkyl, $C_1$-$C_8$-haloalkyl, $C_2$-$C_8$-alkynyl; $C_5$-$C_{10}$-hetaryl or $C_6$-$C_{10}$-aryl, wherein the $C_5$-$C_{10}$-hetaryl or $C_6$-$C_{10}$-aryl moieties optionally carry 1, 2, 3, 4, or 5 identical or different substituents selected from the group consisting of halogen, CN, $C_1$-$C_4$-alkyl, $C_1$-$C_4$-haloalkyl, $C_2$-$C_4$-alkynyl, $C_5$-$C_6$-hetaryl and $C_6$-aryl, wherein said $C_5$-$C_6$-hetaryl and $C_6$-aryl moieties optionally carry 1, 2, 3, 4, or 5 substituents selected from the group consisting of halogen, CN, $C_1$-$C_4$-alkyl, $C_1$-$C_4$-haloalkyl, and $C_2$-$C_4$-alkynyl;

$R^c$ and $R^d$ are independently of each other selected from the group consisting of the group consisting of H, $C_1$-$C_4$-alkyl, $C_3$-$C_8$-cycloalkyl, and $C_5$-$C_{10}$-hetaryl;

or $R^c$ and $R^d$ together with the N-atom to which they are bonded form a 5- to 6-membered, saturated or unsaturated heterocycle.

5. The method according to claim 1, wherein:
$R^1$ is propargyl, and
$R^2$, $R^3$ and $R^4$ are independently selected from the group consisting of H, OH, $C_1$-$C_2$-alkyl, $C_1$-$C_2$-alkoxy, $OC(=O)C_1$-$C_2$-alkyl, $C(=O)OOC_1$-$C_2$-alkyl, and $C(=O)OOH$, or $R^2$ and $R^4$, or $R^3$ and $R^4$ together form a bridge, which forms together with the atoms to which the substituents are bonded an annulated saturated, partly or fully unsaturated, or aromatic 5 to 10-membered monocyclic or bicyclic carbocyclic ring, wherein the carbocyclic ring optionally carries 1, 2, or 3 identical or different substituents selected from the group consisting of =O, halogen, $C_1$-$C_2$-haloalkyl, $C_1$-$C_2$-alkyl and $C_1$-$C_2$-alkoxy.

6. The method according to claim 1, wherein:
$R^1$ is $C_3$-allenyl, and
$R^2$, $R^3$ and $R^4$ are independently selected from the group consisting of H, OH, $C_1$-$C_2$-alkyl, $C_1$-$C_2$-alkoxy, $OC(=O)C_1$-$C_2$-alkyl, $C(=O)OOC_1$-$C_2$-alkyl, and $C(=O)OOH$, or $R^2$ and $R^4$, or $R^3$ and $R^4$ together form a bridge, which forms together with the atoms to which the substituents are bonded an annulated saturated, partly or fully unsaturated, or aromatic 5 to 10-membered monocyclic or bicyclic carbocyclic ring, wherein the carbocyclic ring optionally carries 1, 2, or 3 identical or different substituents selected from the group consisting of =O, halogen, $C_1$-$C_2$-haloalkyl, $C_1$-$C_2$-alkyl and $C_1$-$C_2$-alkoxy.

7. The method according to claim 1, wherein:
$R^2$, $R^3$ and $R^4$ are independently selected from the group consisting of H, halogen, $OR^a$, $C(=O)OR^a$, and $C_1$-$C_4$-alkyl; and
$R^a$ is H, $C_1$-$C_8$-alkyl, or $C_1$-$C_8$-haloalkyl.

8. The method according to claim 1, wherein:
$R^3$ and $R^4$ together form a bridge, which forms together with the atoms to which $R^3$ and $R^4$ are bonded an annulated partly or fully unsaturated, or aromatic 5 to 10-membered carbocyclic ring, wherein the carbocyclic ring optionally carries 1, 2, or 3 identical or different substituents selected from the group consisting of =O, halogen, CN, and $OR^a$; and $R^a$ is H, $C_1$-$C_8$-alkyl, or $C_1$-$C_8$-haloalkyl.

9. The method according to claim 1, wherein the composition comprising the compound of Formula I, or the stereoisomer, the salt, the tautomer, or N-oxide thereof:

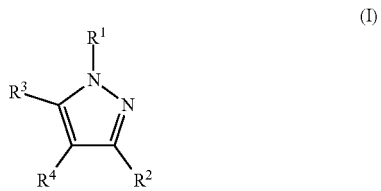

(I)

wherein:

$R^1$ is propargyl, or $R^1$ is a terminal $C_3$-$C_4$-allenyl group, preferably $C_3$-allenyl;

$R^2$, $R^3$ and $R^4$ are independently of each other selected from H, OH, $C_1$-$C_2$-alkyl, $C_1$-$C_2$-alkoxy, OC(=O)$C_1$-$C_2$-alkyl, C(=O)OO$C_1$-$C_2$-alkyl, and C(=O)OOH, or $R^2$ and $R^4$, or $R^3$ and $R^4$ together form a bridge, which forms together with the atoms to which the substituents are bonded an annulated saturated, partly or fully unsaturated, or aromatic 5 to 10-membered monocyclic or bicyclic carbocyclic ring, wherein the carbocyclic ring optionally carries 1, 2, or 3 identical or different substituents selected from =O, halogen, $C_1$-$C_2$-haloalkyl, $C_1$-$C_2$-alkyl and $C_1$-$C_2$-alkoxy;

and the composition further comprises a carrier.

10. The method according to claim 1, wherein the composition comprising the compound of Formula I, or the stereoisomer, the salt, the tautomer, or N-oxide thereof:

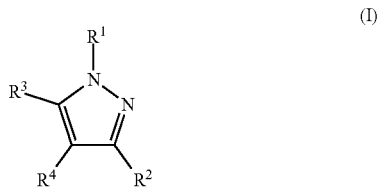

(I)

wherein:

$R^1$ is propargyl, or $R^1$ is a terminal $C_3$-$C_4$-allenyl group, preferably $C_3$-allenyl;

$R^2$, $R^3$ and $R^4$ are independently of each other selected from H, OH, $C_1$-$C_2$-alkyl, $C_1$-$C_2$-alkoxy, OC(=O)$C_1$-$C_2$-alkyl, C(=O)OO$C_1$-$C_2$-alkyl, and C(=O)OOH, or $R^2$ and $R^4$, or $R^3$ and $R^4$ together form a bridge, which forms together with the atoms to which the substituents are bonded an annulated saturated, partly or fully unsaturated, or aromatic 5 to 10-membered monocyclic or bicyclic carbocyclic ring, wherein the carbocyclic ring optionally carries 1, 2, or 3 identical or different substituents selected from =O, halogen, $C_1$-$C_2$-haloalkyl, $C_1$-$C_2$-alkyl and $C_1$-$C_2$-alkoxy;

and the composition further comprises a fertilizer.

11. The method according to claim 10, wherein the fertilizer is selected from the group consisting of an ammonium-containing fertilizer; an organic fertilizer; a urea-containing fertilizer, an inorganic fertilizer, a coated fertilizer, a slow-release fertilizer, and combinations thereof, and the fertilizer may be solid or liquid.

12. The method according to claim 1, further comprising applying a fertilizer to the locus where nitrification occurs.

13. The method according to claim 12, wherein the fertilizer is selected from the group consisting of an ammonium-containing fertilizer; an organic fertilizer; a urea-containing fertilizer, an inorganic fertilizer, a coated fertilizer, a slow-release fertilizer, and combinations thereof, and the fertilizer may be solid or liquid.

14. The method according to claim 1, wherein the locus where nitrification occurs is an agricultural location.

15. The method according to claim 1, wherein the locus where nitrification occurs is a field where crops are currently being grown or a field where crops will be grown.

16. The method according to claim 15, wherein the crop is selected from the group consisting of wheat, barley, oat, rye, soybean, corn, potatoes, oilseed rape, canola, sunflower, cotton, sugar cane, sugar beet, rice, spinach, lettuce, asparagus, cabbages, sorghum, and combinations thereof.

17. The method according to claim 1, further comprising applying a fertilizer to the locus where nitrification occurs, wherein the compound of Formula (I) and the fertilizer are applied sequentially or simultaneously, and when the application is sequential, a time lag between applying the fertilizer and the compound of Formula (I) is up to three weeks, and the compound of Formula (I) may be applied before or after the fertilizer.

18. The method according to claim 17, wherein the fertilizer is selected from the group consisting of an ammonium-containing fertilizer; an organic fertilizer; a urea-containing fertilizer, an inorganic fertilizer, a coated fertilizer, a slow-release fertilizer, and combinations thereof, and the fertilizer may be solid or liquid.

19. The method according to claim 1, wherein the locus where nitrification occurs is a plant growing on soil, and the plant is selected from the group consisting of (i) an agricultural plant; (ii) a vegetable; (iii) sorghum; (iv) a silvicultural plant; (v) an ornamental plant; and (vi) a horticultural plant;

wherein said plant is in its natural form or in a genetically modified form.

20. The method according to claim 1, wherein the compound of Formula (I) is:

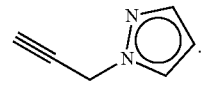.

21. A method for treating a fertilizer, the method comprising applying a compound of Formula (I), or a stereoisomer, salt, tautomer or N-oxide thereof, to the fertilizer, wherein

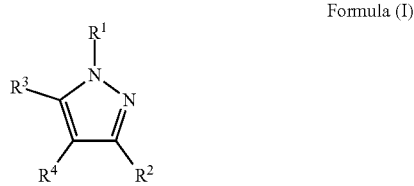

Formula (I)

R¹ is C₄-C₆-alkynyl, propargyl, or C₃-C₆-allenyl, wherein the C-atoms of these groups optionally carry 1, 2, or 3 identical or different substituents selected from the group consisting of halogen, CN, OR$^a$, NO₂, NR$^c$R$^d$, NR$^b$(C=O)R$^a$, O(C=O)R$^a$, C(=O)R$^a$, C(=O)OR$^a$, C(=O)NR$^c$R$^d$, S(O)$_m$R$^a$, and S(O)$_m$NR$^c$R$^d$;

R², R³ and R⁴ are independently selected from the group consisting of H, halogen, CN, OR$^a$, NO₂, NR$^c$R$^d$, NR$^b$(C=O)R$^a$, C(=O)R$^a$, C(=O)OR$^a$, C(=O)NR$^c$R$^d$, S(O)$_m$R$^a$, S(O)$_m$NR$^c$R$^d$; C₁-C₈-alkyl, C₃-C₈-cycloalkyl, C₂-C₈-alkenyl, C₂-C₈-alkynyl, wherein the C-atoms of these groups optionally carry 1, 2, or 3 identical or different substituents selected from the group consisting of halogen, CN, OR$^a$, NO₂, NR$^c$R$^d$, NR$^b$(C=O)R$^a$, C(=O)R$^a$, C(=O)OR$^a$, C(=O)NR$^c$R$^d$, S(O)$_m$R$^a$, and S(O)$_m$NR$^c$R$^d$; C₆-C₁₀-aryl, and C₅-C₁₀-hetaryl, wherein the aromatic moieties optionally carry 1, 2, 3, 4, or 5 identical or different substituents selected from the group consisting of halogen, CN, OR$^a$, C₁-C₄-alkyl, C₁-C₄-haloalkyl, C₂-C₄-alkenyl, and C₂-C₄-alkynyl;

or R³ and R⁴ together form a bridge, which forms together with the atoms to which R³ and R⁴ are bonded an annulated partly or fully unsaturated, or aromatic 5 to 10-membered carbocyclic or heterocyclic ring, wherein the heterocyclic ring may carry 1, 2, or 3 heteroatoms being selected from O, S, and N, of which at least one of S and N may optionally be oxidized, and wherein the carbocyclic or heterocyclic ring optionally carries 1, 2, 3, 4, or 5 identical or different substituents selected from the group consisting of =O, halogen, CN, OR$^a$, NO₂, NR$^c$R$^d$, NR$^b$(C=O)R$^a$, C(=O)R$^a$, C(=O)OR$^a$, C(=O)NR$^c$R$^d$, O(C=O)NR$^c$R$^d$, C₁-C₄-alkyl, C₁-C₄-haloalkyl, C₆-C₁₀-aryl, C₅-C₁₀-hetaryl, C₅-C₁₀-carbocyclyl, and C₅-C₁₀-heterocyclyl, wherein the C₆-C₁₀-aryl, C₅-C₁₀-hetaryl, C₅-C₁₀-carbocyclyl, and C₅-C₁₀-heterocyclyl moieties optionally carry 1, 2, 3, 4, or 5 identical or different substituents selected from the group consisting of =O, halogen, CN, C₁-C₄-alkyl, and C₁-C₄-haloalkyl;

or R² and R⁴ together form a bridge, which forms together with the atoms to which R² and R⁴ are bonded an annulated partly or fully unsaturated, or aromatic 5 to 10-membered carbocyclic or heterocyclic ring, wherein the heterocyclic ring may carry 1, 2, or 3 heteroatoms being selected from O, S, and N, of which at least one of S and N may optionally be oxidized, and wherein the carbocyclic or heterocyclic ring optionally carries 1, 2, 3, 4, or 5 identical or different substituents selected from the group consisting of =O, halogen, CN, OR$^a$, NO₂, NR$^c$R$^d$, NR$^b$(C=O)R$^a$, C(=O)R$^a$, C(=O)OR$^a$, C(=O)NR$^c$R$^d$, O(C=O)NR$^c$R$^d$, C₁-C₄-alkyl, C₁-C₄-haloalkyl, C₆-C₁₀-aryl, C₅-C₁₀-hetaryl, C₅-C₁₀-carbocyclyl, and C₅-C₁₀-heterocyclyl, wherein the C₆-C₁₀-aryl, C₅-C₁₀-hetaryl, C₅-C₁₀-carbocyclyl, and C₅-C₁₀-heterocyclyl moieties optionally carry 1, 2, 3, 4, or 5 identical or different substituents selected from the group consisting of =O, halogen, CN, C₁-C₄-alkyl, and C₁-C₄-haloalkyl;

R$^a$ is selected from the group consisting of H, C₁-C₈-haloalkyl, C₂-C₈-alkenyl, C₂-C₈-alkynyl; C₅-C₁₀-hetaryl and C₆-C₁₀-aryl, wherein the C₅-C₁₀-hetaryl or C₆-C₁₀-aryl moieties optionally carry 1, 2, 3, 4, or 5 identical or different substituents selected from the group consisting of halogen, CN, OH, C₁-C₄-alkyl, C₁-C₄-alkoxy, C₂-C₄-alkenyl, C₂-C₄-alkynyl, C₅-C₆-hetaryl and C₆-aryl, wherein said C₅-C₆-hetaryl and C₆-aryl moieties optionally carry 1, 2, 3, 4, or 5 substituents selected from the group consisting of halogen, CN, OH, C₁-C₄-alkyl, C₁-C₄-alkoxy, C₂-C₄-alkenyl, and C₂-C₄-alkynyl;

R$^b$ is selected from the group consisting of H, C₃-C₈-cycloalkyl, C₂-C₄-alkenyl, C₂-C₈-alkynyl, and C₆-C₁₀-aryl;

R$^c$ and R$^d$ are independently selected from the group consisting of H, C₁-C₄-haloalkyl, C₃-C₈-cycloalkyl, C₆-C₁₀-aryl, and C₅-C₁₀-hetaryl;

or R$^c$ and R$^d$ together with the N-atom to which they are bonded form a 5- to 6-membered, saturated or unsaturated heterocycle, which may carry a further heteroatom being selected from O, S, and N as a ring member atom, of which at least one S and N may optionally be oxidized, and wherein the heterocyclic ring optionally carries 1, 2, 3, 4, or 5 substituents, which are independently selected from the group consisting of halogen, CN, OH, NO₂, C₁-C₄-alkoxy, C₁-C₄-haloalkyl, C₁-C₄-alkoxy, and C₁-C₄-haloalkoxy; and m is 0, 1, or 2.

22. The method according to claim 21, wherein the fertilizer is selected from the group consisting of an ammonium-containing fertilizer; an organic fertilizer; a urea-containing fertilizer, an inorganic fertilizer, a coated fertilizer, a slow-release fertilizer, and combinations thereof, and the fertilizer may be solid or liquid.

23. The method according to claim 21, wherein
R¹ is a terminal C₄-alkynyl group, propargyl, or a terminal C₃-C₄-allenyl group.

24. The method according to claim 21, wherein
R², R³ and R⁴ are independently selected from the group consisting of H, halogen, OR$^a$, C(=O)OR$^a$, and C₁-C₄-alkyl; and
R$^a$ is H, C₁-C₈-alkyl, or C₁-C₈-haloalkyl.

25. The method according to claim 21, wherein at least one of the compound of Formula (I) and the fertilizer further comprises a carrier.

26. The method according to claim 21, wherein the compound is:

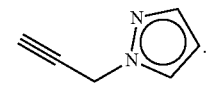

27. A composition comprising:
(i) a compound of Formula I, or a stereoisomer, a salt, a tautomer, or N-oxide thereof:

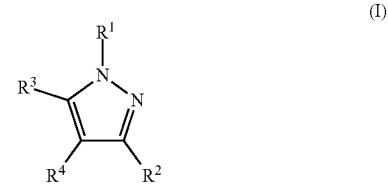

wherein:
R¹ is propargyl, or
R¹ is a terminal C₃-C₄-allenyl group;
R², R³ and R⁴ are independently of each other selected from H, OH, C₁-C₂-alkyl, C₁-C₂-alkoxy, OC(=O)C₁-C₂-alkyl, C(=O)OOC₁-C₂-alkyl, and C(=O)OOH,
or R² and R⁴, or R³ and R⁴ together form a bridge, which forms together with the atoms to which the substituents are bonded an annulated saturated, partly or fully unsaturated, or aromatic 5 to 10-membered monocyclic or bicyclic carbocyclic ring, wherein the carbocyclic ring optionally carries 1, 2, or 3 identical or different substituents selected from =O, halogen, $C_1$-$C_2$-haloalkyl, $C_1$-$C_2$-alkyl and $C_1$-$C_2$-alkoxy; and
(ii) at least one carrier.

28. The composition of claim 27 wherein the compound of Formula (I) is

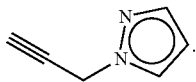

29. An agrochemical mixture comprising:
(i) a fertilizer; and
(ii) a compound of Formula I, or a stereoisomer, a salt, a tautomer, or N-oxide thereof:

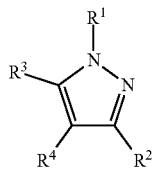

wherein:

$R^1$ is propargyl, or $R^1$ is a terminal $C_3$-$C_4$-allenyl group;

$R^2$, $R^3$ and $R^4$ are independently of each other selected from H, OH, $C_1$-$C_2$-alkyl, $C_1$-$C_2$-alkoxy, OC(=O)$C_1$-$C_2$-alkyl, C(=O)OO$C_1$-$C_2$-alkyl, and C(=O)OOH, or $R^2$ and $R^4$, or $R^3$ and $R^4$ together form a bridge, which forms together with the atoms to which the substituents are bonded an annulated saturated, partly or fully unsaturated, or aromatic 5 to 10-membered monocyclic or bicyclic carbocyclic ring, wherein the carbocyclic ring optionally carries 1, 2, or 3 identical or different substituents selected from =O, halogen, $C_1$-$C_2$-haloalkyl, $C_1$-$C_2$-alkyl and $C_1$-$C_2$-alkoxy.

30. The agrochemical mixture of claim 29 wherein the compound of Formula (I) is

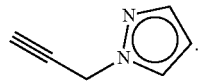

* * * * *